(12) United States Patent
Jiao et al.

(10) Patent No.: US 12,054,710 B2
(45) Date of Patent: Aug. 6, 2024

(54) METHOD OF ctDNA LIBRARY CONSTRUCTION AND SEQUENCING DATA ANALYSIS FOR SIMULTANEOUSLY DETECTING MULTIPLE COMMON MUTATIONS IN LIVER CANCER

(71) Applicants: CANCER HOSPITAL CHINESE ACADEMY OF MEDICAL SCIENCES, Beijing (CN); GENETRON HEALTH (BEIJING) CO, LTD., Beijing (CN)

(72) Inventors: Yuchen Jiao, Beijing (CN); Chunfeng Qu, Beijing (CN); Pei Wang, Beijing (CN); Kun Chen, Beijing (CN); Yuting Wang, Beijing (CN); Qianqian Song, Beijing (CN); Sizhen Wang, Beijing (CN); Hai Yan, Beijing (CN)

(73) Assignees: CANCER HOSPITAL CHINESE ACADEMY OF MEDICAL SCIENCES, Beijing (CN); GENETRON HEALTH (BEIJING) CO, LTD., Beijing (CN)

( * ) Notice: Subject to any disclaimer, the term of this patent is extended or adjusted under 35 U.S.C. 154(b) by 606 days.

(21) Appl. No.: 17/257,611

(22) PCT Filed: Apr. 11, 2019

(86) PCT No.: PCT/CN2019/082233
§ 371 (c)(1),
(2) Date: Jan. 4, 2021

(87) PCT Pub. No.: WO2020/007089
PCT Pub. Date: Jan. 9, 2020

(65) Prior Publication Data
US 2022/0119806 A1    Apr. 21, 2022

(30) Foreign Application Priority Data
Jul. 3, 2018   (CN) .......................... 201810712104.3

(51) Int. Cl.
*C12Q 1/6806*   (2018.01)
*C12N 15/10*   (2006.01)
*C12Q 1/6855*   (2018.01)
*C12Q 1/6886*   (2018.01)

(52) U.S. Cl.
CPC ....... *C12N 15/1096* (2013.01); *C12Q 1/6806* (2013.01); *C12Q 1/6855* (2013.01); *C12Q 1/6886* (2013.01); *C12Q 2600/156* (2013.01)

(58) Field of Classification Search
CPC ............... C12Q 1/6806; C12Q 1/6855; C12Q 2525/191; C12Q 2531/113; C12Q 2525/155; C12Q 2535/122; C12Q 2600/156; C12Q 2563/179; C12N 15/1093
See application file for complete search history.

(56) References Cited

U.S. PATENT DOCUMENTS

2016/0319345 A1* 11/2016 Gnerre .................. G16B 30/10

FOREIGN PATENT DOCUMENTS

| CN | 106192018 A | 12/2016 | |
|---|---|---|---|
| CN | 106834275 A | 6/2017 | |
| CN | 107385042 A | 11/2017 | |
| CN | 107723352 A | 2/2018 | |
| CN | 108192955 A | 6/2018 | |
| JP | 2015-517307 A | 6/2015 | |
| JP | 2015-519909 A | 7/2015 | |
| JP | 2018-514207 A | 6/2018 | |
| KR | 10-2003-0080002 A | 10/2003 | |
| WO | WO-2013138510 A1 * | 9/2013 | ........... C12Q 1/6806 |
| WO | WO-2013169339 A1 * | 11/2013 | .............. A61P 35/00 |
| WO | 2018/041062 A | 3/2018 | |

OTHER PUBLICATIONS

Schmitt et al. PNAS. 2012. 109(36): 14508-14513. (Year: 2012).*
International Search Report issued in corresponding International Application No. PCT/CN2019/082233; mailed Jul. 24, 2019; State Intellectual Property Office of the P.R. China, Beijing, China, 8 pgs.
First Office Action issued in corresponding Chinese Application No. 201810712104.3; mailed Dec. 21, 2020; State Intellectual Property Office of the P.R. China, Beijing, China, 35 pgs.
Qiaoling Li, "Establishment of Method for Detection of Low-Frequency Mutation by Double Sequencing Combined with Chip Capture", Chinese Master's Dissertations Full-text Database, Medical Technology Section, vol. 4, E072-4, Apr. 15, 2016; 13 pgs. (Reference cited in First Chinese Office Action dated Dec. 21, 2020).
Second Office Action issued in corresponding Chinese Application No. 201810712104.3; mailed Aug. 23, 2021; State Intellectual Property Office of the P.R. China, Beijing, China, 13 pgs.

(Continued)

*Primary Examiner* — Joseph G. Dauner
(74) *Attorney, Agent, or Firm* — HAUPTMAN HAM, LLP

(57) ABSTRACT

A method of ctDNA library construction and sequencing data analysis for simultaneously detecting multiple common mutations in liver cancer. The library construction method and sequencing data analysis process have the following advantages: 1. Simultaneous detection of multiple mutation forms in liver cancer without capturing; 2. Suitable for efficient capture of ultra-small target regions; 3. The library may support 10-20 tests; 4. Ligate the DNA barcode to the starting ctDNA molecule during the library construction process, and cooperate with the biological information analysis process to achieve high specific detection of low-frequency mutations in ctDNA; 5. The library is usable for PCR hot spots detection and sequencing by a capture method at the same time, the added DNA barcode may effectively filter out false positive mutations and achieve high-specificity sequencing based on duplex. The disclosure helps with early screening, disease tracking, efficacy evaluation, prognosis prediction and the like of liver cancer.

11 Claims, 1 Drawing Sheet
Specification includes a Sequence Listing.

(56) References Cited

OTHER PUBLICATIONS

Office Action issued in corresponding Korean Patent Application No. 1020217001494; mailed Oct. 14, 2022; 44 pgs.
Lv, Xiaoxing et al.; "Detection of Rare Mutations in CtDNA Using Next Generation Sequencing"; Journal of Visualized Experiments; vol. 126, pp. 1-8; Aug. 24, 2017.
Office Action issued in corresponding Japanese Patent Application No. 2020562138; mailed Apr. 11, 2023; 4 pgs.
Exended Search Report issued in European Patent Application No. 2019831550; mailed Mar. 29, 2022; 5 pgs.

* cited by examiner

METHOD OF ctDNA LIBRARY CONSTRUCTION AND SEQUENCING DATA ANALYSIS FOR SIMULTANEOUSLY DETECTING MULTIPLE COMMON MUTATIONS IN LIVER CANCER

RELATED APPLICATIONS

The present application is a National Phase of International Application Number PCT/CN2019/082233 filed Apr. 11, 2019 and claims priority to Chinese Application Number 201810712104.3 filed Jul. 3, 2018.

INCORPORATION BY REFERENCE

The sequence listing provided in the file entitled 2020-12-29_Sequence_Listing_Mod_2, which is an ASCII text file that was created on Jul. 7, 2021, and which comprises 64,557 bytes, is hereby incorporated by reference in its entirety.

TECHNICAL FIELD

The invention relates to a method of ctDNA library construction and sequencing data analysis for simultaneously detecting multiple common mutations in liver cancer.

BACKGROUND OF THE INVENTION ctDNA (circulating tumor DNA), that is, circulating tumor DNA, refers to tumor DNA that exists in blood, cerebrospinal fluid and other body fluids, and is free outside of cells. ctDNA usually mixes with free DNA derived from normal cells in the blood and is called cfDNA (cell free DNA). By detecting mutations in ctDNA, it may guide targeted medication, treatment monitoring, early cancer screening and the like. Detection methods based on ctDNA comprise 1) PCR-based Hotspot Mutation Detection Method, which usually detects one or more hotspot mutations or known mutations, but cannot detect either complex mutations such as gene fusion, or unknown mutations; 2) Capture/Next Generation Sequencing Method, which may detect position mutations of more genes, including complex mutations, but capture kits are generally expensive, complicated to operate, and time-consuming. In the context of the above two methods, the current ctDNA detection has the following difficulties: 1) the amount of ctDNA specimens obtained from a blood draw is limited, which is usually only enough to support one detection. This results that ctDNA detection is generally performed in a single platform and is one-time in clinical practice. When one mutation is detected using the low-cost hotspot mutation method, other mutations cannot be detected further. In clinical detection, it is often necessary to determine the target and plan of subsequent detection based on the results of the first detection, which requires re-drawing blood in subsequent detection. In addition, ctDNA-related clinical detection or research often needs to compare the advantages and disadvantages of multiple technologies, which requires samples that are several times the normal blood volume, which is usually unacceptable to patients. 2) Whether it is the PCR method or the capture method, the noise mutations generated during the amplification process will seriously interfere with the detection of ctDNA low-frequency mutations, causing false positive results and misleading the diagnosis and treatment of patients. 3) The content of ctDNA mutations is low, which is prone to contamination during operation, causing false positive results.

Liver cancer is the fifth most common tumor and the second most lethal tumor in the world. More than half of the world's liver cancers occur in China, and hepatitis B-related liver cancer is the main one. Hepatitis B-related liver cancer has almost no hot-spot mutations such as KRAS and BRAF. The mutations are mainly mutations in the coding region of several genes such as TP53 and CTNNB1, mutations in promoter region of TERT rich in GC, and also comprise complex mutations such as HBV integration and copy number variation of TERT. As a result, there is currently no simple, low-cost, and reliable system for detecting ctDNA mutations in liver cancer. Early screening, disease tracking, efficacy evaluation, and prognosis prediction for liver cancer through ctDNA detection have important clinical significance.

SUMMARY OF THE INVENTION

The object of the present invention is to provide a method of ctDNA library construction and sequencing data analysis for simultaneously detecting multiple common mutations in liver cancer.

The present invention provides a method for constructing a sequencing library, which may comprise the following steps sequentially:
(1) DNA samples are treated with terminal repair and are added a base A at 3' end sequentially;
(2) Ligate the DNA sample treated in step (1) to an adapter mixture, and obtain a library after PCR amplification;

The adapter mixture may consist of N adapters;

Each adapter is obtained by forming a partially double-stranded structure from an upstream primer A and a downstream primer A; the upstream primer A has a sequencing adapter A, a random tag, an anchor sequence A and a base T at the 3' end; the downstream primer A has an anchor sequence B and a sequencing adapter B; the partially double-stranded structure is formed by the reverse complementation of the anchor sequence A in the upstream primer A and the anchor sequence B in the downstream primer A;

The sequencing adapter A and sequencing adapter B are corresponding sequencing adapters selected according to different sequencing platforms;

The random tag may be random bases of 8-14 bp;

The length of the anchor sequence A may be 14-20 bp, and the number of consecutive repeated bases is less than or equal to 3;

N adapters use N different anchor sequences, the bases at the same position are balanced, and the number of mismatched bases is greater than 3;

N may be any natural number greater than or equal to 8.

The anchor sequence does not interact with other parts of the primer such as forming a hairpin structure, dimer, and the like.

The upstream primer A may comprise a sequencing adapter A, a random tag, an anchor sequence A and a base T from the 5' end sequentially.

The downstream primer A may comprise an anchor sequence B and a sequencing adapter B from the 5' end sequentially.

In the above, the adapter usually used for library construction is formed by annealing of two sequences, and has a "Y"-like structure. The complementary pairing part between the two sequences (i.e., the anchor sequence A and the anchor sequence B) is called an anchor sequence. The anchor sequence may be used as a built-in tag for sequence fixation to label the original template molecule.

The "bases at the same position are balanced" may mean that among the N anchor sequence As in the adapter mixture bases at each position from the start base to the end base are balanced, that is, A, T, C and G are distributed evenly.

The "number of mismatched bases is greater than 3" may mean that the adapter mixture contains N anchor sequence As, and there are at least 3 different bases between each anchor sequence A. The difference may be a difference in a position or a difference in an order.

The DNA sample may be a genomic DNA, cDNA, ct DNA or cf DNA sample.

Specifically, N may be 12.

The random tag may specifically be random bases of 8 bp.

The length of the anchor sequence A may specifically be 12 bp.

When N=12, the nucleotide sequence of the anchor sequence A may be specifically as shown in positions 30-41 of SEQ ID NO: 1 from the 5' end in the sequence listing, positions 30-41 of SEQ ID NO: 3 from the 5' end in the sequence listing, positions 30-41 of SEQ ID NO: 5 from the 5' end in the sequence listing, positions 30-41 of SEQ ID NO: 7 from the 5' end in the sequence listing, positions 30-41 of SEQ ID NO: 9 from the 5' end in the sequence listing, positions 30-41 of SEQ ID NO: 11 from the 5' end in the sequence listing, positions 30-41 of SEQ ID NO: 13 from the 5' end in the sequence listing, positions 30-41 of SEQ ID NO: 15 from the 5' end in the sequence listing, positions 30-41 of SEQ ID NO: 17 from the 5' end in the sequence listing, positions 30-41 of SEQ ID NO: 19 from the 5' end in the sequence listing, positions 30-41 of SEQ ID NO: 21 from the 5' end in the sequence listing, positions 30-41 of SEQ ID NO: 23 from the 5' end, respectively.

The sequencing adapter A may be specifically a sequencing adapter of the TRUSEQ® sequencing kit from Illumina, Inc., of San Diego, California, for ligating adapters to each end of an RNA molecule, and then reverse transcribing and amplifying to generate a cDNA library. The sequencing adapter A may be specifically as shown in positions 1-29 of SEQ ID NO: 1 from the 5' end in the sequence listing.

The sequencing adapter B may be specifically a sequencing adapter of the NEXTERA™ sequencing kit from Illumina, Inc., for using a bead-transposome complex to tag-ment genomic DNA by fragmenting and adding adapter tag sequences in a single reaction step. After saturation with input DNA, the bead-based transposome complex fragments a set number of DNA molecules. The sequencing adapter B may be specifically shown as positions 13-41 of the SEQ ID NO: 2 from the 5' end in the sequence listing.

When N=12, the 12 adapter are as follows:

The adapter 1 may be obtained from a partially double-stranded structure formed by the single-stranded DNA molecule shown as SEQ ID NO: 1 and the single-stranded DNA molecule shown as SEQ ID NO: 2 in the sequence listing; the adapter 2 may be obtained from a partially double-stranded structure formed by the single-stranded DNA molecule shown as SEQ ID NO: 3 and the single-stranded DNA molecule shown as SEQ ID NO: 4 in the sequence listing; the adapter 3 may be obtained from a partially double-stranded structure formed by the single-stranded DNA molecule shown as SEQ ID NO: 5 and the single-stranded DNA molecule shown as SEQ ID NO: 6 in the sequence listing; the adapter 4 may be obtained from a partially double-stranded structure formed by the single-stranded DNA molecule shown as SEQ ID NO: 7 and the single-stranded DNA molecule shown as SEQ ID NO: 8 in the sequence listing; the adapter 5 may be obtained from a partially double-stranded structure formed by the single-stranded DNA molecule shown as SEQ ID NO: 9 and the single-stranded DNA molecule shown as SEQ ID NO: 10 in the sequence listing; the adapter 6 may be obtained from a partially double-stranded structure formed by the single-stranded DNA molecule shown as SEQ ID NO: 11 and the single-stranded DNA molecule shown as SEQ ID NO: 12 in the sequence listing; the adapter 7 may be obtained from a partially double-stranded structure formed by the single-stranded DNA molecule shown as SEQ ID NO: 13 and the single-stranded DNA molecule shown as SEQ ID NO: 14 in the sequence listing; the adapter 8 may be obtained from a partially double-stranded structure formed by the single-stranded DNA molecule shown in SEQ ID NO: 15 and the single-stranded DNA molecule shown as SEQ ID NO: 16 in the sequence listing; the adapter 9 may be obtained from a partially double-stranded structure formed by the single-stranded DNA molecule shown as SEQ ID NO: 17 and the single-stranded DNA molecule shown as SEQ ID NO: 18 in the sequence listing; the adapter 10 may be obtained from a partially double-stranded structure formed by the single-stranded DNA molecule shown as SEQ ID NO: 19 and the single-stranded DNA molecule shown as SEQ ID NO: 20 in the sequence listing; the adapter 11 may be obtained from a partially double-stranded structure formed by the single-stranded DNA molecule shown as SEQ ID NO: 21 and the single-stranded DNA molecule shown as SEQ ID NO: 22 in the sequence listing; the adapter 12 may be obtained from a partially double-stranded structure formed by the single-stranded DNA molecule shown as SEQ ID NO: 23 and the single-stranded DNA molecule shown as SEQ ID NO: 24 in the sequence listing.

The adapter may be obtained by annealing the upstream primer A and the downstream primer A.

In the adapter mixture, each adapter may be mixed in equimolar.

The method may also comprise the step of amplifying the library obtained in step (2). The amplified primers are designed according to the adapters. Specifically, at least one sequence of the amplified primer must match a certain sequence of a adapter. The primer pair used in the amplification may specifically be composed of two single-stranded DNA molecules as shown in SEQ ID NO: 25 and SEQ ID NO: 26 in the sequence listing.

The present invention also protects a DNA library constructed by the method described above.

The present invention also protects a kit for constructing a sequencing library, which comprises any of the adapter mixtures described above.

The kit may also comprise reagents for DNA extraction, reagents for DNA library construction, reagents for library purification, reagents for library capture, and other materials for library construction.

The present invention also protects a kit for detecting mutations in liver cancer from a DNA sample, comprising any of the adapter mixtures and primer combinations described above; the primer combination comprise a primer set I, a primer set II, a primer set III and a primer set IV;

Each primer in the primer set I and the primer set II is a specific primer designed according to a region related to liver cancer, and its role is to locate at a specific position in the genome to achieve an enrichment of the target region by PCR;

The nucleotide sequence of each primer in the primer set III and the primer set IV consists of "an adapter sequence+a specific sequence", wherein the specific sequence is used for further enrichment of the target region, and the adapter sequence is used to form a complete library molecule by PCR the complete library molecule may be sequenced;

The primer set III and the primer set I may be in a "nested" relationship; and the primer set IV and the primer set II may be in a "nested" relationship.

The regions related to liver cancer may be specifically regions related to high-frequency mutation genes (TP53, CTNNB1, AXIN1, TERT) and hot spots for HBV integration.

The primer set I may specifically be composed of single-stranded DNA as shown in SEQ ID NO: 28 to SEQ ID NO: 105 in the sequence listing.

The primer set II may specifically be composed of single-stranded DNA as shown in SEQ ID NO: 106 to SEQ ID NO: 187 in the sequence listing.

The primer set III may specifically be composed of single-stranded DNA as shown in SEQ ID NO: 191 to SEQ ID NO: 265 in the sequence listing.

The primer set IV may specifically be composed of single-stranded DNA as shown in SEQ ID NO: 266 to SEQ ID NO: 344 in the sequence listing.

The primer combination may specifically consist of the primer set I, the primer set II, the primer set III and the primer set IV.

The kit may also comprise reagents for DNA extraction, reagents for DNA library construction, reagents for library purification, reagents for library capture, and other materials for library construction.

The present invention also protects any of primer combinations described above. The use of the primer combination may be to prepare a kit for detecting mutations in liver cancer from a DNA sample.

The present invention also protects use of any of primer combinations described above in preparing a kit for detecting mutations in liver cancer from a DNA sample.

The present invention also protects a method for detecting target mutations in a DNA sample, which comprises the following steps:
(1) Construct a library according to any of the method described above;
(2) Perform two cycles of nested PCR amplification on the library obtained in step (1), sequence the products, and analyze the occurrence of target mutations in the DNA sample according to the sequencing results;

In the step (2), the first cycle of PCR amplification is performed using a primer combination A;

The primer combination A consists of an upstream primer A and a downstream primer combination A;

The upstream primer A is a library amplification primer used for library amplification in step (1);

The downstream primer combination A is a combination of N primers designed according to N target points;

Using the product of the first cycle of PCR as a template, the second cycle of PCR amplification is performed with a primer combination B;

The primer combination B consists of an upstream primer B, a downstream primer combination B and index primer;

The partial sequence of the upstream primer B is a library amplification primer used for amplifying the product of the first cycle of PCR;

The primers in the downstream primer combination B and the primers in the downstream primer combination A for detecting the same target form a nested relationship, and each primer has a segment that binds to the index primer;

The index primer contains a segment that binds to each primer in the downstream primer combination B, and an index sequence.

A part of sequence of the upstream primer A is exactly the same as the sequence of the "sequencing adapter A of the upstream primer A of each adapter".

The upstream primer B is used to complement the adapter sequence of the library molecule, so that the amplified product may be sequenced directly. The upstream primer B and a part of nucleotide sequences of the upstream primer A (primers used in the first cycle of PCR amplification) are completely identical.

The nucleotide sequence of the upstream primer A may be specifically as shown in SEQ ID NO: 27 in the sequence listing.

The nucleotide sequence of the upstream primer B may be specifically as shown in SEQ ID NO: 188 in the sequence listing.

The index primer may comprise a segment A, an index sequence and a segment B from the 5' end. The index primer may specifically consist of the segment A, the index sequence and the segment B. The nucleotide sequence of the segment A may be as shown in SEQ ID NO: 189 in the sequence listing. The nucleotide sequence of the segment B may be as shown in SEQ ID NO: 190 in the sequence listing.

When the target mutation is a mutation in liver cancer, the primer combination A consists of any one of the primer set I and the primer set II described above; the primer combination B consists of any one of the primer set III and the primer set IV described above. The primer set I and the primer set II are used to perform the first cycle of PCR amplification on the template respectively, and the amplified product by the primer set I is used as a template for the second cycle of amplification by the primer set III, the amplified product by the primer set II is used as a template for the second cycle of amplification by the primer set IV, and then the amplified products are mixed in equal volumes.

The analysis process of the sequencing result may be: backtrack the sequencing data of DNA molecules with the same random tag sequence, the same length of the DNA insert, and the same breakpoints at both ends of the DNA insert (i.e., the sequence of the DNA fragment is the same (except for the comprised mutations)) to a molecular cluster. If the number of molecules in the cluster is greater than 5 and the consistency rate of molecular mutations in the cluster is greater than 80% and the number of clusters is greater than or equal to 5, the mutation is a true mutation from the original DNA sample.

The present invention also protects a method for detecting multiple target mutations in a DNA sample, which may comprise the following steps:
(1) Construct a library according to any of the methods described above;
(2) Perform an enrichment of a target region on the library of step (1) and sequencing, and analyze the occurrence of target mutations in the DNA sample according to the sequencing results.

The enrichment of a target region may be performed by using an existing commercially available targeted capture kit (for example, Agilent sureselect XT targeted capture kit, Agilent 5190-8646), and the primer pair in the last step of PCR amplification is replaced by a primer pair consisting of a primer A and a primer B. The nucleotide sequence of the primer A may be as shown in SEQ ID NO: 345 in the sequence listing. The primer B may comprise a segment A, an index sequence and a segment B. The primer B may specifically consist of the segment A, the index sequence and the segment B. The nucleotide sequence of the segment A may be as shown in SEQ ID NO: 346 in the sequence listing. The nucleotide sequence of the segment B may be as shown in SEQ ID NO: 347 in the sequence listing.

The analysis process of the sequencing result may be: backtrack the sequencing data of the starting single-stranded DNA with the same length of the DNA insert, the same breakpoints at both ends of the DNA insert, and the same anchor sequence at both ends to a molecular cluster; a starting double-stranded DNA molecular cluster, which has the same length of the DNA insert, the same sequence except for the mutation point, the same anchor sequence at both ends of the molecular cluster except for the opposite position, is labeled as a pair of duplex molecular clusters; for a certain mutation, if there is at least one pair of duplex molecular cluster supported, it may be judged as true. If there is no duplex molecular cluster and at least 4 molecular clusters supported, it may be judged as true.

In the above, usually multiple libraries of different samples are mixed together for sequencing, and the index sequence is used to label different samples. After the sequencing is completed, the total sequencing data is split according to different index sequences. The design principle of the index sequence is basically similar to the design principle of the anchor sequence described earlier.

The present invention has the following advantages due to the above technical solutions:
1. Simultaneously detect point mutations, insert or indel mutations, HBV integration and other mutation forms in liver cancer ctDNA without capturing. Compared with the capture method, this technology requires only a few DNA primers, does not require expensive capture probes and hybridization reagents, and the cost is greatly reduced; the operation process is simple, and the time required may be shortened from 36 hours as required in capture method to 8 hours.
2. It is suitable for the efficient capture of ultra-small target regions, which may be as small as 10% of the smallest target region of the capture method, greatly improving the sequencing efficiency. For example, the combination of common mutations TP53, CTNNB1, AXIN1, TERT, and HBV integration in liver cancer is an ultra-small target region suitable for this technology. The target rate of enriching this target region using the capture method is less than 10%, while in this technology it may reach greater than 80%, which greatly improves the sequencing efficiency and reduces sequencing costs.
3. After one detection, the amplified library may support 10-20 follow-up detections, and the result of each test may represent the mutation status of all original ctDNA specimens, without reducing sensitivity and specificity.
4. In the library construction process, the DNA barcode is ligated to the starting ctDNA molecule, and the biological information analysis process is used to achieve high specific detection of low-frequency mutations in ctDNA.
5. The library constructed by this technology may be used for PCR hot spot detection and capture method sequencing simultaneously, and the library constructed from one specimen may support multiple detections at the same time. The added DNA barcode may effectively filter out false positive mutations, and realize a highly specific sequencing based on duplex.

The invention has important clinical significance for early screening, disease tracking, efficacy evaluation, prognosis prediction and the like of liver cancer.

BEST MODE OF IMPLEMENTING THE INVENTION

Figure 1:
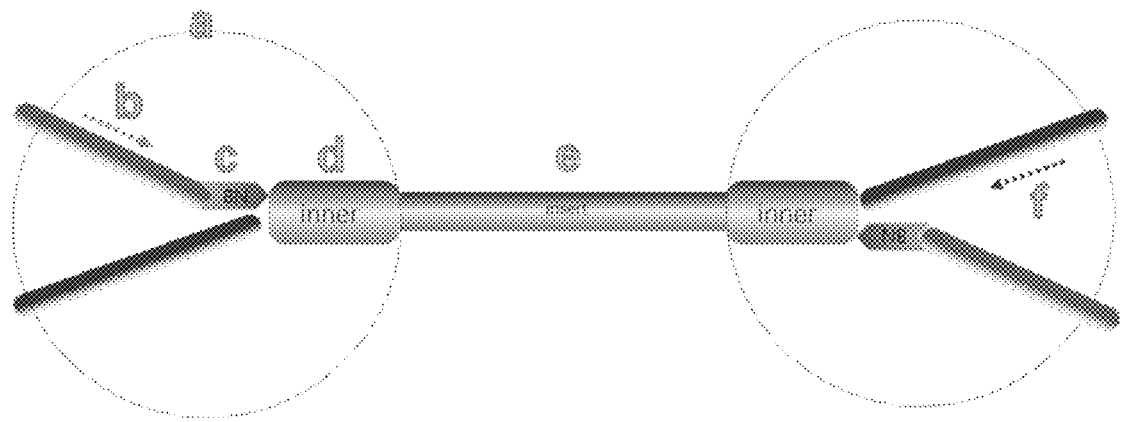
FIG. 1 is a schematic diagram of the adapter and the primer architecture.

The following examples facilitate a better understanding of the present invention, but do not limit the present invention. The experimental methods in the following examples are conventional methods unless otherwise specified. The experimental materials used in the following examples, unless otherwise specified, are all purchased from conventional biochemical reagent stores. The quantitative tests in the following examples are all set to three repeated experiments, and the results are averaged.

Example 1. Construction of MC Library

I. The Blunt End Repairing and Treatment of Adding a A in cfDNA Molecules

Take 10-45 ng cfDNA, configure the reaction system as shown in Table 1, and then perform the end repairing and addition of A at the 3' end on the PCR machine according to the procedures in Table 2 to obtain the reaction product (stored at 4° C.).

TABLE 1

| Reaction system | |
| --- | --- |
| Ingredients | Volume |
| cfDNA | 50 µl |
| End Repair & A-Tailing Buffer (KAPA KK8505) | 7 µl |
| End Repair & A-Tailing Enzyme Mix (KAPA KK8505) | 3 µl |
| Total volume | 60 µl |

TABLE 2

| Reaction procedures | |
| --- | --- |
| Temperature | Time |
| 20° C. | 30 min |
| 65° C. | 30 min |

II. Ligation of cfDNA and Adapter

Configure the reaction system according to Table 3 and react at 20° C. for 15 minutes to obtain the ligation product (stored at 4° C.).

TABLE 3

| Reaction system | |
| --- | --- |
| Ingredients | Volume |
| Reaction product obtained in Step I | 60 µl |
| Adapter Mix (50 µpM) | 1.5 µl |
| DNase/RNase-Free Water | 8.5 µl |
| Ligation Buffer (KAPA KK8505) | 30 µl |
| DNA Ligase (KAPA KK8505) | 10 µl |
| Total volume | 110 µl |

Sequence information of Adapter Mix is shown in Table 4.

The single-stranded DNA in Table 4 was dissolved and diluted with TE to a final concentration of 100 µM. Mix the two single-stranded DNA in the same group in equal volumes (50 μl each), and perform annealing (annealing procedure: 95° C., 15 min; 25° C., 2 h) to obtain 12 groups of DNA solutions. Mix the 12 groups of DNA solutions in equal volumes to obtain Adapter Mix.

TABLE 4

Adapter Mix sequence information

| Group | No. | Name | Sequence (5'-3') |
|---|---|---|---|
| 1 | 1 | R21_F | GACACGACGCTCTTCCGATCTNNNNNNNN<u>CCACTAGTAGCCT</u> (SEQ ID NO: 1) |
|  | 2 | R21_R | <u>GGCTACTAGTGGC</u>TGTCTCTTATACACATCTCCGAGCCCAC (SEQ ID NO: 2) |
| 2 | 3 | R22_F | GACACGACGCTCTTCCGATCTNNNNNNNN<u>GGACTGTGTCGGT</u> (SEQ ID NO: 3) |
|  | 4 | R22_R | <u>CCGACACAGTCCC</u>TGTCTCTTATACACATCTCCGAGCCCAC (SEQ ID NO: 4) |
| 3 | 5 | R23_F | GACACGACGCTCTTCCGATCTNNNNNNNN<u>GGTACTGACAGGT</u> (SEQ ID NO: 5) |
|  | 6 | R23_R | <u>CCTGTCAGTACCC</u>TGTCTCTTATACACATCTCCGAGCCCAC (SEQ ID NO: 6) |
| 4 | 7 | R24_F | GACACGACGCTCTTCCGATCTNNNNNNNN<u>CCTAGTACAGCCT</u> (SEQ ID NO: 7) |
|  | 8 | R24_R | <u>GGCTGTACTAGG</u>CTGTCTCTTATACACATCTCCGAGCCCAC (SEQ ID NO: 8) |
| 5 | 9 | R25_F | GACACGACGCTCTTCCGATCTNNNNNNNN<u>GGTAGTCAGAGGT</u> (SEQ ID NO: 9) |
|  | 10 | R25_R | <u>CCTCTGACTACCC</u>TGTCTCTTATACACATCTCCGAGCCCAC (SEQ ID NO: 10) |
| 6 | 11 | R26_F | GACACGACGCTCTTCCGATCTNNNNNNNN<u>TTCTCACGTGTTT</u> (SEQ ID NO: 11) |
|  | 12 | R26_R | <u>AACACGTGAGAA</u>CTGTCTCTTATACACATCTCCGAGCCCAC (SEQ ID NO: 12) |
| 7 | 13 | R27_F | GACACGACGCTCTTCCGATCTNNNNNNNN<u>AACTCCACGTAAT</u> (SEQ ID NO: 13) |
|  | 14 | R27_R | <u>TTACGTGGAGTT</u>CTGTCTCTTATACACATCTCCGAGCCCAC (SEQ ID NO: 14) |
| 8 | 15 | R28_F | GACACGACGCTCTTCCGATCTNNNNNNNN<u>TTCTCGAGAATTT</u> (SEQ ID NO: 15) |
|  | 16 | R28_R | <u>AATTCTCGAGAA</u>CTGTCTCTTATACACATCTCCGAGCCCAC (SEQ ID NO: 16) |
| 9 | 17 | R29_F | GACACGACGCTCTTCCGATCTNNNNNNNN<u>AAACTCTTCCAAT</u> (SEQ ID NO: 17) |
|  | 18 | R29_R | <u>TTGGAAGAGTTT</u>CTGTCTCTTATACACATCTCCGAGCCCAC (SEQ ID NO: 18) |
| 10 | 19 | R30_F | GACACGACGCTCTTCCGATCTNNNNNNNN<u>TTGGAACGTCTTT</u> (SEQ ID NO: 19) |
|  | 20 | R30_R | <u>AAGACGTTCCAA</u>CTGTCTCTTATACACATCTCCGAGCCCAC (SEQ ID NO: 20) |
| 11 | 21 | R31_F | GACACGACGCTCTTCCGATCTNNNNNNNN<u>CCGGACTCCTCCT</u> (SEQ ID NO: 21) |
|  | 22 | R31_R | <u>GGAGGAGTCCGG</u>CTGTCTCTTATACACATCTCCGAGCCCAC (SEQ ID NO: 22) |
| 12 | 23 | R32_F | GACACGACGCTCTTCCGATCTNNNNNNNN<u>AAGGAGGAGTAAT</u> (SEQ ID NO: 23) |
|  | 24 | R32_R | <u>TTACTCCTCCTT</u>CTGTCTCTTATACACATCTCCGAGCCCAC (SEQ ID NO: 24) |

In Table 4, 8 Ns represent a random tag of 8 bp. In practical applications, the length of the random tag may be 8-14 bp.

The underlined part indicates an anchor sequence of 12 bp. In the upstream and downstream sequences of each group, the underlined parts are reverse complementary, and the upstream and downstream sequences may be combined together to form an adapter by annealing. At the same time, the anchor sequence may be used as a built-in tag for sequence fixation to label the original template molecule. In practical applications, the length of the anchor sequence may be 12-20 bp, the number of consecutive repeat bases is no more than 3, and cannot interact with other parts of the primer (such as forming a hairpin structure, dimer, etc.). Bases at each position among 12 groups are balanced, and the number of mismatch bases is greater than 3.

The bold T at the end of the upstream sequence is complementary to the "A" added at the end of the original molecule for TA ligation.

In the upstream sequence, positions 1 to 21 from the 5' end (TRUSEQ® Sequencing Kit from Illumina) are the sequencing primer binding sequences, and positions 1 to 19 from the 5' end are the part for library amplification primers.

In the downstream sequence, the non-underlined part (NEXTERA™ sequencing kit from Illumina) is the sequence primer binding sequence, and positions 1 to 22 from the 3' end are the part for designing library amplification primers.

Table 4 contains 12 sets of adapters, which may form 12×12=144 label combinations. Combining the sequence information of the molecule itself, it is enough to distinguish all molecules in the original sample. In practical applications, the number of groups may also be appropriately increased (increased synthesis cost) or decreased (the distinguishing effect is slightly weaker).

The structure of the ligation product is shown in FIG. 1, wherein a is the adapter part, b and f are the library amplification primers, c is the random tag of 8 bp (indicated by 8 Ns in Table 4), d is the anchor sequence of 12 bp (indicated by the underlined part in Table 4), and e is the insert fragment (cfDNA).

III. Purification of the Ligation Products

Add 110 μl AMPure XP magnetic beads (Beckman A63880) to the ligation product obtained in step II, vortex and mix well, place at room temperature for 10 minutes, and absorb on a magnetic stand for 5 minutes; after the solution is clear, discard the supernatant, and then wash twice by adding 200 μl 80% (volume percentage content) ethanol aqueous solution and discard the supernatant; after the ethanol is dried, add 30 μl DNase/RNase-Free Water, vortex to mix, place at room temperature for 10 minutes, absorb on a magnetic stand for 5 minutes, and pipette the supernatant solution into the PCR tube as PCR templates.

IV. Amplification and Purification of the Library

1. Take the PCR template obtained in step III, configure the reaction system according to Table 5, and perform PCR amplification according to Table 6 to obtain PCR amplification products (stored at 4° C.).

TABLE 5

| Reaction system | |
| --- | --- |
| Ingredients | Volume |
| HIFI(KAPA KK8505) | 35 μl |
| MC_F (33 μM) | 2.5 μl |
| MC_R (33 μM) | 2.5 μl |
| Template | 30 μl |
| Total volume | 70 μl |

Information of primers in Table 5 is provided as follows:

```
MC_F (SEQ ID NO: 25):
GACACGACGCTCTTCCGAT (5'-3');

MC_R (SEQ ID NO: 26):
GTGGGCTCGGAGATGTGTATAA (5'-3').
```

TABLE 6

| Reaction Procedure | | |
| --- | --- | --- |
| Temperature | Time | Number of Cycle |
| 98° C. | 45 s | |
| 98° C. | 15 s | 10 cycles |
| 60° C. | 30 s | |
| 72° C. | 30 s | |
| 72° C. | 5 min | |

2. Add 90 μl AMPure XP magnetic beads to the PCR amplification product obtained in step 1, vortex to mix, place at room temperature for 10 minutes, and absorb on the magnetic stand for 5 minutes; after the solution is clear, discard the supernatant, and then wash twice by adding 200 μl 80% (volume percentage content) ethanol aqueous solution, discard the supernatant; after the ethanol is dried, add 100 μl DNase/RNase-Free Water, vortex to mix, place at room temperature for 10 minutes, absorb on a magnetic stand for 5 minutes, absorb the supernatant solution to obtain the product (stored at −20° C.). The product is the MC library that may be stored for a long time and used repeatedly.

After detection, the MC library may support 10-20 follow-up tests, and the result of each test may represent the mutation status of all the original samples without reducing sensitivity and specificity. At the same time, the library construction method is not only suitable for cfDNA samples, but also for genomic DNA or cDNA samples.

Figure 2:
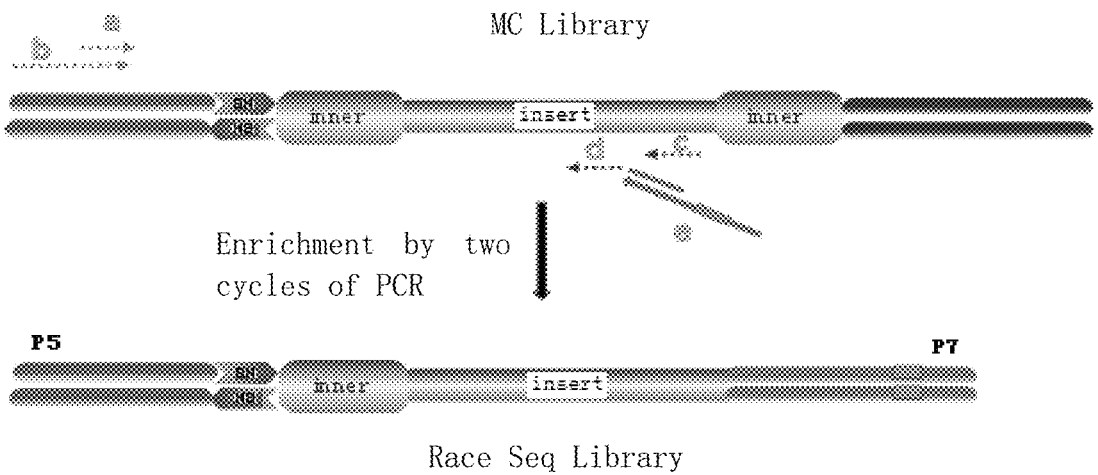
FIG. 2 is a schematic diagram of enrichment of a target region and library construction in Race Seq.

Example 2. RaceSeq Enriches the Target Region and Constructs a Sequencing Library As shown in FIG. 2, two cycles of PCR amplification were performed on the MC library by using the primers designed for the relevant regions of high-frequency mutation genes (TP53, CTNNB1, AXIN1, TERT), the HBV integration hotspot region in the Chinese liver cancer, and the fixed primers. The amplified product is the sequencing library.

In FIG. 2, a is the upstream primer of the first cycle of library amplification, b is the upstream primer of the second cycle of library amplification, c is the downstream primer library of the first cycle of library amplification for the enrichment of specific target sequences, d is the downstream primer library of the second cycle of library amplification for the enrichment of specific target sequences, and e is the index primer for adding index sequence.

1. Take 300 ng of the MC library prepared in Example 1 and divide it into two parts, configure the reaction system in Table 7 (in one part GSP1A mix is added, and in the other part GSP1B mix is added), and perform the first cycle of PCR amplification according to the reaction procedure in Table 9 to obtain products of the first cycle of amplification (totally, two products of the first cycle amplification are obtained, one is the amplification product of GSP1A mix and the other is the amplification product of GSP1B mix).

TABLE 7

| Reaction system | |
| --- | --- |
| Ingredients | Volume |
| Hifi (KAPA KK8505) | 15 μl |
| Upstream primer 1355 | 3 μl |

TABLE 7-continued

Reaction system

| Ingredients | Volume |
| --- | --- |
| GSP1A mix/GSP1B mix | 2 μl |
| MC library | 10 μl |
| Total volume | 30 μl |

In Table 7, the information of primers is as follows:

```
Upstream primer 1355 (SEQ ID NO: 27):
TCTTTCCCTACACGACGCTCTTCCGAT (5'-3').
```

GSP1A mix: Dissolve each primer in the primer pool GSP1A in Table 8 with TE at a concentration of 100 μM, then mix in equal volumes, and dilute with TE to 0.3 μM. The primers in the primer pool GSP1A are used to amplify the positive strand of the template.

GSP1B mix: Dissolve each primer in the primer pool GSP1B in Table 8 with TE at a concentration of 100 μM, then mix in equal volumes and dilute with TE to 0.3 μM. The primers in the primer pool GSP1B are used to amplify the negative strand of the template.

In the primer pool GSP1A and the primer pool GSP1B, the primers with the same number detect the same mutation site from both positive and negative directions, and simultaneous use may maximize the enrichment of the original molecular information.

TABLE 8

Primer information

| Gene Name | Primer Pool | Primer No. | Sequence of Primers (5'-3') |
| --- | --- | --- | --- |
| AXIN1 | GSP1A | HA1009 | TGTATTAGGGTGCAGCGCTC (SEQ ID NO: 28) |
| AXIN1 | GSP1A | HA1010 | CGCTCGGATCTGGACCTG (SEQ ID NO: 29) |
| AXIN1 | GSP1A | HA1011 | TGGAGCCCTGTGACTCGAA (SEQ ID NO: 30) |
| AXIN1 | GSP1A | HA1012 | GTGACCAGGACATGGATGAGG (SEQ ID NO: 31) |
| AXIN1 | GSP1A | HA1013 | TCCTCCAGTAGACGGTACAGC (SEQ ID NO: 32) |
| AXIN1 | GSP1A | HA1014 | TGCTGCTTGTCCCCACAC (SEQ ID NO: 33) |
| AXIN1 | GSP1A | HA1015 | CCGCTTGGCACCACTTCC (SEQ ID NO: 34) |
| AXIN1 | GSP1A | HA1016 | GGCACGGGAAGCACGTAC (SEQ ID NO: 35) |
| AXIN1 | GSP1A | HA1017 | CCTTGCAGTGGGAAGGTG (SEQ ID NO: 36) |
| CTNNB1 | GSP1A | HA1018 | GACAGAAAAGCGGCTGTTAGTCA (SEQ ID NO: 37) |
| TERT | GSP1A | HA1019 | CCGACCTCAGCTACAGCAT (SEQ ID NO: 38) |
| TERT | GSP1A | HA1020 | ACTTGAGCAACCCGGAGTCTG (SEQ ID NO: 39) |
| TERT | GSP1A | HA1021 | CTCCTAGCTCTGCAGTCCGA (SEQ ID NO: 40) |
| TERT | GSP1A | HA1022 | GCGCCTGGCTCCATTTCC (SEQ ID NO: 41) |
| TERT | GSP1A | HA1023 | CGCCTGAGAACCTGCAAAGAG (SEQ ID NO: 42) |
| TERT | GSP1A | HA1024 | GTCCAGGGAGCAATGCGT (SEQ ID NO: 43) |
| TERT | GSP1A | HA1025 | CGGGTTACCCCACAGCCTA (SEQ ID NO: 44) |
| TERT | GSP1A | HA1026 | GGCTCCCAGTGGATTCGC (SEQ ID NO: 45) |
| TERT | GSP1A | HA1027 | GTCCTGCCCCTTCACCTT (SEQ ID NO: 46) |
| HBV-C | GSP1A | HA1028 | CCGACTACTGCCTCACCCATAT (SEQ ID NO: 47) |
| HBV-C | GSP1A | HA1029 | GGGTTTTCTTGTTGACAAGAATCCT (SEQ ID NO: 48) |
| HBV-C | GSP1A | HA1030 | CCAACCTCCAATCACTCACCAA (SEQ ID NO: 49) |
| HBV-C | GSP1A | HA1031 | GGCGTTTTATCATATTCCTCTTCATCCT (SEQ ID NO: 50) |
| HBV-C | GSP1A | HA1032 | CTACTTCCAGGAACATCAACTACCAG (SEQ ID NO: 51) |
| HBV-C | GSP1A | HA1033 | CTGCACTTGTATTCCCATCCCAT (SEQ ID NO: 52) |
| HBV-C | GSP1A | HA1034 | TCAGTTTACTAGTGCCATTTGTTCAGT (SEQ ID NO: 53) |
| HBV-C | GSP1A | HA1035 | TACAACATCTTGAGTCCCTTTTTACCTC (SEQ ID NO: 54) |
| HBV-C | GSP1A | HA1036 | AGAATTGTGGGTCTTTTGGGCTT (SEQ ID NO: 55) |

TABLE 8-continued

Primer information

| Gene Name | Primer Pool | Primer No. | Sequence of Primers (5'-3') |
|---|---|---|---|
| HBV-C | GSP1A | HA1037 | TGTAAACAATATCTGAACCTTTACCCTGTT (SEQ ID NO: 56) |
| HBV-C | GSP1A | HA1038 | GCATGCGTGGAACCTTTGTG (SEQ ID NO: 57) |
| HBV-C | GSP1A | HA1039 | AACTCTGTTGTCCTCTCTCGGAA (SEQ ID NO: 58) |
| HBV-C | GSP1A | HA1040 | CTGAATCCCGCGGACGAC (SEQ ID NO: 59) |
| HBV-C | GSP1A | HA1041 | CCGTCTGTGCCTTCTCATCTG (SEQ ID NO: 60) |
| HBV-C | GSP1A | HA1042 | GAACGCCCACCAGGTCTTG (SEQ ID NO: 61) |
| HBV-C | GSP1A | HA1043 | CCTTGAGGCGTACTTCAAAGACTG (SEQ ID NO: 62) |
| HBV-C | GSP1A | HA1044 | GGAGGCTGTAGGCATAAATTGGT (SEQ ID NO: 63) |
| HBV-C | GSP1A | HA1045 | GTCCTACTGTTCAAGCCTCCAA (SEQ ID NO: 64) |
| HBV-C | GSP1A | HA1046 | GGGCTTCTGTGGAGTTACTCTC (SEQ ID NO: 65) |
| HBV-C | GSP1A | HA1047 | TTGTATCGGGAGGCCTTAGAGT (SEQ ID NO: 66) |
| HBV-C | GSP1A | HA1048 | TTCTGTGTTGGGGTGAGTTGA (SEQ ID NO: 67) |
| HBV-C | GSP1A | HA1049 | CCAGCATCCAGGGAATTAGTAGTCA (SEQ ID NO: 68) |
| HBV-C | GSP1A | HA1050 | TTCCTGTCTTACCTTTGGAAGAGAAAC (SEQ ID NO: 69) |
| HBV-C | GSP1A | HA1051 | CCGGAAACTACTGTTGTTAGACGTA (SEQ ID NO: 70) |
| HBV-C | GSP1A | HA1052 | CGTCGCAGAAGATCTCAATCTCG (SEQ ID NO: 71) |
| HBV-C | GSP1A | HA1053 | AAACTCCCTCCTTTCCTAACATTCATTT (SEQ ID NO: 72) |
| HBV-C | GSP1A | HA1054 | TATGCCTGCTAGGTTCTATCCTAACC (SEQ ID NO: 73) |
| HBV-C | GSP1A | HA1055 | GGCATTATTTACATACTCTGTGGAAGG (SEQ ID NO: 74) |
| HBV-C | GSP1A | HA1056 | GTTGGTCTTCCAAACCTCGACA (SEQ ID NO: 75) |
| HBV-C | GSP1A | HA1057 | TTCAACCCCAACAAGGATCACT (SEQ ID NO: 76) |
| HBV-C | GSP1A | HA1058 | TTCCACCAATCGGCAGTCAG (SEQ ID NO: 77) |
| HBV-B | GSP1A | HA1059 | GCCCTGCTCAGAATACTGTCT (SEQ ID NO: 78) |
| HBV-B | GSP1A | HA1060 | ATTCGCAGTCCCAAATCTCC (SEQ ID NO: 79) |
| HBV-B | GSP1A | HA1061 | CATCTTCCTCTGCATCCTGCT (SEQ ID NO: 80) |
| HBV-B | GSP1A | HA1062 | TTCCAGGATCATCAACCACCAG (SEQ ID NO: 81) |
| HBV-B | GSP1A | HA1063 | GTCCCTTTATGCCGCTGT (SEQ ID NO: 82) |
| HBV-B | GSP1A | HA1064 | ACCCTTATAAAGAATTTGGAGCTACTGTG (SEQ ID NO: 83) |
| HBV-B | GSP1A | HA1065 | CTCCTGAACATTGCTCACCTCA (SEQ ID NO: 84) |
| TP53 | GSP1A | HA1071 | AGACTGCCTTCCGGGTCA (SEQ ID NO: 85) |
| TP53 | GSP1A | HA1072 | CCTGTGGGAAGCGAAAATTCCA (SEQ ID NO: 86) |
| TP53 | GSP1A | HA1073 | ACCTGGTCCTCTGACTGCT (SEQ ID NO: 87) |
| TP53 | GSP1A | HA1074 | AAGCAATGGATGATTTGATGCTGT (SEQ ID NO: 88) |
| TP53 | GSP1A | HA1075 | GACCCAGGTCCAGATGAAGC (SEQ ID NO: 89) |
| TP53 | GSP1A | HA1076 | TCCTGGCCCCTGTCATCT (SEQ ID NO: 90) |
| TP53 | GSP1A | HA1077 | GTGCCCTGACTTTCAACTCTGT (SEQ ID NO: 91) |
| TP53 | GSP1A | HA1078 | CAACTGGCCAAGACCTGC (SEQ ID NO: 92) |

TABLE 8-continued

Primer information

| Gene Name | Primer Pool | Primer No. | Sequence of Primers (5'-3') |
|---|---|---|---|
| TP53 | GSP1A | HA1079 | CGCCATGGCCATCTACAAGC (SEQ ID NO: 93) |
| TP53 | GSP1A | HA1080 | GGTCCCCAGGCCTCTGAT (SEQ ID NO: 94) |
| TP53 | GSP1A | HA1081 | GAGTGGAAGGAAATTTGCGTGT (SEQ ID NO: 95) |
| TP53 | GSP1A | HA1082 | GCACTGGCCTCATCTTGGG (SEQ ID NO: 96) |
| TP53 | GSP1A | HA1083 | CCATCCACTACAACTACATGTGTAAC (SEQ ID NO: 97) |
| TP53 | GSP1A | HA1084 | TTTCCTTACTGCCTCTTGCTTCTC (SEQ ID NO: 98) |
| TP53 | GSP1A | HA1085 | GGGACGGAACAGCTTTGAGG (SEQ ID NO: 99) |
| TP53 | GSP1A | HA1086 | CACAGAGGAAGAGAATCTCCGCA (SEQ ID NO: 100) |
| TP53 | GSP1A | HA1087 | TGCCTCAGATTCACTTTTATCACCTT (SEQ ID NO: 101) |
| TP53 | GSP1A | HA1088 | CTCAGGTACTGTGTATATACTTACTTCTCC (SEQ ID NO: 102) |
| TP53 | GSP1A | HA1089 | CGTGAGCGCTTCGAGATGT (SEQ ID NO: 103) |
| TP53 | GSP1A | HA1090 | GTGATGTCATCTCTCCTCCCTG (SEQ ID NO: 104) |
| TP53 | GSP1A | HA1091 | TGAAGTCCAAAAAGGGTCAGTCTAC (SEQ ID NO: 105) |
| AXIN1 | GSP1B | HB1009 | GGGAGCATCTTCGGTGAAAC (SEQ ID NO: 106) |
| AXIN1 | GSP1B | HB1010 | CAGGCTTATCCCATCTTGGTCA (SEQ ID NO: 107) |
| AXIN1 | GSP1B | HB1011 | TTGGTGGCTGGCTTGGTC (SEQ ID NO: 108) |
| AXIN1 | GSP1B | HB1012 | GCTGTACCGTCTACTGGAGGA (SEQ ID NO: 109) |
| AXIN1 | GSP1B | HB1013 | GCTTGTTCTCCAGCTCTCGGA (SEQ ID NO: 110) |
| AXIN1 | GSP1B | HB1014 | GGGAAGTGGTGCCAAGCG (SEQ ID NO: 111) |
| AXIN1 | GSP1B | HB1015 | GCACACGCTGTACGTGCT (SEQ ID NO: 112) |
| AXIN1 | GSP1B | HB1016 | GCCTCCACCTGCTCCTTG (SEQ ID NO: 113) |
| AXIN1 | GSP1B | HB1017 | CCCTCAATGATCCACTGCATGA (SEQ ID NO: 114) |
| CTNNB1 | GSP1B | HB1018 | CTCATACAGGACTTGGGAGGTATC (SEQ ID NO: 115) |
| TERT | GSP1B | HB1019 | CACAACCGCAGGACAGCT (SEQ ID NO: 116) |
| TERT | GSP1B | HB1020 | CTCCAAGCCTCGGACTGC (SEQ ID NO: 117) |
| TERT | GSP1B | HB1021 | GCCTCACACCAGCCACAAC (SEQ ID NO: 118) |
| TERT | GSP1B | HB1022 | TCCCCACCATGAGCAAACCA (SEQ ID NO: 119) |
| TERT | GSP1B | HB1023 | GTGCCTCCCTGCAACACT (SEQ ID NO: 120) |
| TERT | GSP1B | HB1024 | GCACCACGAATGCCGGAC (SEQ ID NO: 121) |
| TERT | GSP1B | HB1025 | GTGGGGTAACCCGAGGGA (SEQ ID NO: 122) |
| TERT | GSP1B | HB1026 | GAGGAGGCGGAGCTGGAA (SEQ ID NO: 123) |
| TERT | GSP1B | HB1027 | AGCGCTGCCTGAAACTCG (SEQ ID NO: 124) |
| TERT | GSP1B | HB1028 | CGCACGAACGTGGCCAG (SEQ ID NO: 125) |
| HBV-C | GSP1B | HB1029 | GAGCCACCAGCAGGAAAGT (SEQ ID NO: 126) |
| HBV-C | GSP1B | HB1030 | CTAGGAATCCTGATGTTGTGCTCT (SEQ ID NO: 127) |
| HBV-C | GSP1B | HB1031 | CGCGAGTCTAGACTCTGTGGTA (SEQ ID NO: 128) |
| HBV-C | GSP1B | HB1032 | ATAGCCAGGACAAATTGGAGGACA (SEQ ID NO: 129) |
| HBV-C | GSP1B | HB1033 | GACAAACGGGCAACATACCTT (SEQ ID NO: 130) |

TABLE 8-continued

Primer information

| Gene Name | Primer Pool | Primer No. | Sequence of Primers (5'-3') |
|---|---|---|---|
| HBV-C | GSP1B | HB1034 | CCGAAGGTTTTGTACAGCAACAA (SEQ ID NO: 131) |
| HBV-C | GSP1B | HB1035 | CTGAGCCAGGAGAAACGGACTGA (SEQ ID NO: 132) |
| HBV-C | GSP1B | HB1036 | GGGACTCAAGATGTTGTACAGACTTG (SEQ ID NO: 133) |
| HBV-C | GSP1B | HB1037 | GTTAAGGGAGTAGCCCCAACG (SEQ ID NO: 134) |
| HBV-C | GSP1B | HB1038 | CAGGCAGTTTTCGAAAACATTGCTT (SEQ ID NO: 135) |
| HBV-C | GSP1B | HB1039 | TTAAAGCAGGATAGCCACATTGTGTAA (SEQ ID NO: 136) |
| HBV-C | GSP1B | HB1040 | GGCAACAGGGTAAAGGTTCAGATAT (SEQ ID NO: 137) |
| HBV-C | GSP1B | HB1041 | CCACAAAGGTTCCACGCAT (SEQ ID NO: 138) |
| HBV-C | GSP1B | HB1042 | TGGAAAGGAAGTGTACTTCCGAGA (SEQ ID NO: 139) |
| HBV-C | GSP1B | HB1043 | GTCGTCCGCGGGATTCAG (SEQ ID NO: 140) |
| HBV-C | GSP1B | HB1044 | AAGGCACAGACGGGGAGA (SEQ ID NO: 141) |
| HBV-C | GSP1B | HB1045 | TCACGGTGGTCTCCATGC (SEQ ID NO: 142) |
| HBV-C | GSP1B | HB1046 | GGTCGTTGACATTGCTGAGAGT (SEQ ID NO: 143) |
| HBV-C | GSP1B | HB1047 | AACCTAATCTCCTCCCCCAACT (SEQ ID NO: 144) |
| HBV-C | GSP1B | HB1048 | GCAGAGGTGAAAAAGTTGCATGG (SEQ ID NO: 145) |
| HBV-C | GSP1B | HB1049 | CCACCCAAGGCACAGCTT (SEQ ID NO: 146) |
| HBV-C | GSP1B | HB1050 | ACTCCACAGAAGCCCCAA (SEQ ID NO: 147) |
| HBV-C | GSP1B | HB1051 | GCCTCCCGATACAAAGCAGA (SEQ ID NO: 148) |
| HBV-C | GSP1B | HB1052 | GATTCATCAACTCACCCCAACACA (SEQ ID NO: 149) |
| HBV-C | GSP1B | HB1053 | ACATAGCTGACTACTAATTCCCTGGAT (SEQ ID NO: 150) |
| HBV-C | GSP1B | HB1054 | ATCCACACTCCAAAAGACACCAAAT (SEQ ID NO: 151) |
| HBV-C | GSP1B | HB1055 | GCGAGGGAGTTCTTCTTCTAGG (SEQ ID NO: 152) |
| HBV-C | GSP1B | HB1056 | CAGTAAAGTTTCCCACCTTGTGAGT (SEQ ID NO: 153) |
| HBV-C | GSP1B | HB1057 | CCTCCTGTAAATGAATGTTAGGAAAGG (SEQ ID NO: 154) |
| HBV-C | GSP1B | HB1058 | GTTTAATGCCTTTATCCAAGGGCAAA (SEQ ID NO: 155) |
| HBV-C | GSP1B | HB1059 | CTCTTATATAGAATCCCAGCCTTCCAC (SEQ ID NO: 156) |
| HBV-C | GSP1B | HB1060 | CTTGTCGAGGTTTGGAAGACCA (SEQ ID NO: 157) |
| HBV-C | GSP1B | HB1061 | GTTTGAGTTGGCTCCGAACG (SEQ ID NO: 158) |
| HBV-C | GSP1B | HB1062 | CTGAGGGCTCCACCCCAA (SEQ ID NO: 159) |
| HBV-C | GSP1B | HB1063 | GTGAAGAGATGGGAGTAGGCTGT (SEQ ID NO: 160) |
| HBV-B | GSP1B | HB1064 | CCCATCTTTTTGTTTTGTGAGGGTTT (SEQ ID NO: 161) |
| HBV-B | GSP1B | HB1065 | TTAAAGCAGGATATCCACATTGCGTA (SEQ ID NO: 162) |
| HBV-B | GSP1B | HB1066 | TTGCTGAAAGTCCAAGAGTCCT (SEQ ID NO: 163) |
| HBV-B | GSP1B | HB1067 | GGTGAGCAATGTTCAGGAGATTC (SEQ ID NO: 164) |
| HBV-B | GSP1B | HB1068 | ACTACTAGATCCCTGGACGCTG (SEQ ID NO: 165) |
| HBV-B | GSP1B | HB1069 | GGTGGAGATAAGGGAGTAGGCTG (SEQ ID NO: 166) |
| TP53 | GSP1B | HB1071 | TGCCCTTCCAATGGATCCAC (SEQ ID NO: 167) |

TABLE 8-continued

Primer information

| Gene Name | Primer Pool | Primer No. | Sequence of Primers (5'-3') |
|---|---|---|---|
| TP53 | GSP1B | HB1072 | GTCCCCAGCCCAACCCTT (SEQ ID NO: 168) |
| TP53 | GSP1B | HB1073 | CTCTGGCATTCTGGGAGCTT (SEQ ID NO: 169) |
| TP53 | GSP1B | HB1074 | TGGTAGGTTTTCTGGGAAGGGA (SEQ ID NO: 170) |
| TP53 | GSP1B | HB1075 | TGTCCCAGAATGCAAGAAGCC (SEQ ID NO: 171) |
| TP53 | GSP1B | HB1076 | GGCATTGAAGTCTCATGGAAGCCA (SEQ ID NO: 172) |
| TP53 | GSP1B | HB1077 | ACCTCCGTCATGTGCTGTGA (SEQ ID NO: 173) |
| TP53 | GSP1B | HB1078 | CTCACCATCGCTATCTGAGCA (SEQ ID NO: 174) |
| TP53 | GSP1B | HB1079 | GCAACCAGCCCTGTCGTC (SEQ ID NO: 175) |
| TP53 | GSP1B | HB1080 | GCACCACCACACTATGTCGAA (SEQ ID NO: 176) |
| TP53 | GSP1B | HB1081 | TTAACCCCTCCTCCCAGAGAC (SEQ ID NO: 177) |
| TP53 | GSP1B | HB1082 | TTCCAGTGTGATGATGGTGAGGAT (SEQ ID NO: 178) |
| TP53 | GSP1B | HB1083 | CAGCAGGCCAGTGTGCAG (SEQ ID NO: 179) |
| TP53 | GSP1B | HB1084 | CCGGTCTCTCCCAGGACA (SEQ ID NO: 180) |
| TP53 | GSP1B | HB1085 | GTGAGGCTCCCCTTTCTTGC (SEQ ID NO: 181) |
| TP53 | GSP1B | HB1086 | TGGTCTCCTCCACCGCTTC (SEQ ID NO: 182) |
| TP53 | GSP1B | HB1087 | GAAACTTTCCACTTGATAAGAGGTCC (SEQ ID NO: 183) |
| TP53 | GSP1B | HB1088 | CTCCCCCCTGGCTCCTTC (SEQ ID NO: 184) |
| TP53 | GSP1B | HB1089 | GGGGAGTAGGGCCAGGAAG (SEQ ID NO: 185) |
| TP53 | GSP1B | HB1090 | GCCCTTCTGTCTTGAACATGAGT (SEQ ID NO: 186) |
| TP53 | GSP1B | HB1091 | GTGGGAGGCTGTCAGTGG (SEQ ID NO: 187) |

TABLE 9

Reaction Procedure

| Temperature | Time | Number of Cycle |
|---|---|---|
| 98° C. | 3 min | |
| 98° C. | 15 s | 9 cycles |
| 60° C. | 90 s | |
| 72° C. | 120 s | |
| 72° C. | 10 min | |

TABLE 10

Reaction system

| Ingredients | Volume |
|---|---|
| KapaHifi | 15 µl |
| Upstream primer 3355 | 2 µl |
| GSP2Amix/GSP2B mix | 1 µl |
| Index Primers (10 µM) | 2 µl |
| Template (GSP1A mix/GSP1Bmix) | 10 µl |
| Total volume | 30 µl |

2. The two amplified products of the first cycle amplification obtained in step 1 are purified using AMPure XP magnetic beads at a ratio of 1:1.3, and elute with 25 µl DNase/RNase-Free Water to obtain two purified products of the first cycle amplification.

3. Using the two purified products of the first cycle amplification obtained in step 2 as templates, configure the reaction system in Table 10 (when using GSP1A mix amplification product as templates, GSP2A mix is used for amplification; when using GSP1B mix amplification product as templates, GSP2B mix is used for amplification), perform the second cycle of PCR amplification according to the reaction procedure in Table 12 to obtain amplified products of the second cycle of amplification (stored at 4° C.).

In Table 10, information of the primer is as follows:
Upstream primer 3355 (SEQ ID NO: 188): AATGA-TACGGCGACCACCGAGATCTACACTCTTTCCCTA-CACGACGCTCT (5'-3'); the underlined part is the same part as that of the first cycle of upstream primer 1355. Both 3355 and 1355 are fixed sequences for sequencing in the Illumina sequencing platform (can also be replaced with sequences for sequencing in other sequencing platforms).

GSP2A mix: Dissolve each primer in the primer pool GSP2A in Table 11 with TE at a concentration of 100 µM, then mix in equal volumes and dilute with TE to 0.3 µM. The primers in the primer pool GSP2A are used to amplify the positive strand of the template.

GSP2B mix: Dissolve each primer in the primer pool GSP2B in Table 11 with TE at a concentration of 100 µM, then mix in equal volumes and dilute with TE to 0.3 µM. The primers in the primer pool GSP2B are used to amplify the negative strand of the template.

In Table 11, positions 1 to 20 from the 5' end are the part that binds to the Index primer.

The primers with the same primer number in GSP2A mix and GSP1A mix are designed for the same mutation site, and the two primers form a nested relationship.

The primers with the same primer number in GSP2B mix and GSP1B mix are designed for the same mutation site, and the two primers form a nested relationship.

Index primer: CAAGCAGAAGACGGCATACGAGAT (SEQ ID NO: 189)******GTGACTGGAGTTCCTTGGCACCCGAGAATTCCA (SEQ ID NO: 190); the underlined part is the part that binds to GSP2 mix. ****** is the position of the index sequence. The length of the index is 6-8 bp, which is used to distinguish the sequence between samples and facilitate the mixed sequencing of multiple samples. Except for the index sequence, the remaining parts are fixed sequences from Illumina's small RNA sequencing kit.

TABLE 11

Primer information

| Gene name | Primer pool | Primer No. | Sequences of Primers (5'-3') |
|---|---|---|---|
| AXIN1 | GSP2A | HA2009 | CTTGGCACCCGAGAATTCCATTGTTCCTTGACGCAGAG (SEQ ID NO: 191) |
| AXIN1 | GSP2A | HA2010 | CTTGGCACCCGAGAATTCCAGACCTGGGGTATGAGCCTGA (SEQ ID NO: 192) |
| AXIN1 | GSP2A | HA2011 | CTTGGCACCCGAGAATTCCAAGGCTGAAGCTGGCGAGA (SEQ ID NO: 193) |
| AXIN1 | GSP2A | HA2012 | CTTGGCACCCGAGAATTCCATGAGGACGATGGCAGAGACG (SEQ ID NO: 194) |
| AXIN1 | GSP2A | HA2013 | CTTGGCACCCGAGAATTCCAGTACAGCGAAGGCAGAGAGT (SEQ ID NO: 195) |
| AXIN1 | GSP2A | HA2014 | CTTGGCACCCGAGAATTCCACACACAGGAGGAGGAAGGTGA (SEQ ID NO: 196) |
| AXIN1 | GSP2A | HA2015 | CTTGGCACCCGAGAATTCCATGTGTGGACATGGGCTGTG (SEQ ID NO: 197) |
| AXIN1 | GSP2A | HA2016 | CTTGGCACCCGAGAATTCCAACCCAAGTCAGGGCGAA (SEQ ID NO: 198) |
| AXIN1 | GSP2A | HA2017 | CTTGGCACCCGAGAATTCCAGCGTGCAAAAGAAATGCCAAGAAG (SEQ ID NO: 199) |
| CTNNB1 | GSP2A | HA2018 | CTTGGCACCCGAGAATTCCATAGTCACTGGCAGCAACAGTC (SEQ ID NO: 200) |
| TERT | GSP2A | HA2019 | CTTGGCACCCGAGAATTCCACTGCAAGGCCTCGGGAGA (SEQ ID NO: 201) |
| TERT | GSP2A | HA2020 | CTTGGCACCCGAGAATTCCAATTCCTGGGAAGTCCTCAGCT (SEQ ID NO: 202) |
| TERT | GSP2A | HA2021 | CTTGGCACCCGAGAATTCCAGCTTGGAGCCAGGTGCCT (SEQ ID NO: 203) |
| TERT | GSP2A | HA2022 | CTTGGCACCCGAGAATTCCACATTTCCCACCCTTTCTCGACGG (SEQ ID NO: 204) |
| TERT | GSP2A | HA2023 | CTTGGCACCCGAGAATTCCAACGGGCCTGTGTCAAGGA (SEQ ID NO: 205) |
| TERT | GSP2A | HA2024 | CTTGGCACCCGAGAATTCCAATGCGTCCTCGGGTTCGT (SEQ ID NO: 206) |
| TERT | GSP2A | HA2025 | CTTGGCACCCGAGAATTCCAAGCCTAGGCCGATTCGAC (SEQ ID NO: 207) |
| TERT | GSP2A | HA2026 | CTTGGCACCCGAGAATTCCAGATTCGCGGGCACAGACG (SEQ ID NO: 208) |
| TERT | GSP2A | HA2027 | CTTGGCACCCGAGAATTCCATTCCAGCTCCGCCTCCTC (SEQ ID NO: 209) |
| HBV-C | GSP2A | HA2028 | CTTGGCACCCGAGAATTCCACCCATATCGTCAATCTTCTCGAGG (SEQ ID NO: 210) |
| HBV-C | GSP2A | HA2029 | CTTGGCACCCGAGAATTCCATCACAGTACCACAGAGTCTAGACTC (SEQ ID NO: 211) |
| HBV-C | GSP2A | HA2030 | CTTGGCACCCGAGAATTCCAAACCTCTTGTCCTCCAATTTGTCC (SEQ ID NO: 212) |
| HBV-C | GSP2A | HA2031 | CTTGGCACCCGAGAATTCCACCTGCTGCTATGCCTCATCTTC (SEQ ID NO: 213) |
| HBV-C | GSP2A | HA2032 | CTTGGCACCCGAGAATTCCACACGGGACCATGCAAGACC (SEQ ID NO: 214) |
| HBV-C | GSP2A | HA2033 | CTTGGCACCCGAGAATTCCATGGGCTTTCGCAAGATTCCTAT (SEQ ID NO: 215) |
| HBV-C | GSP2A | HA2034 | CTTGGCACCCGAGAATTCCACGTAGGGCTTTCCCCCACT (SEQ ID NO: 216) |
| HBV-C | GSP2A | HA2035 | CTTGGCACCCGAGAATTCCACCTCTATTACCAATTTTCTTTTGTCTTTGGG (SEQ ID NO: 217) |
| HBV-C | GSP2A | HA2036 | CTTGGCACCCGAGAATTCCAACACAATGTGGCTATCCTGCTT (SEQ ID NO: 218) |
| HBV-C | GSP2A | HA2037 | CTTGGCACCCGAGAATTCCAGGCAACGGTCAGGTCTCT (SEQ ID NO: 219) |
| HBV-C | GSP2A | HA2038 | CTTGGCACCCGAGAATTCCACTCTGCCGATCCATACTGCGGAA (SEQ ID NO: 220) |
| HBV-C | GSP2A | HA2039 | CTTGGCACCCGAGAATTCCACACTTCCTTTCCATGGCTGCTA (SEQ ID NO: 221) |

TABLE 11-continued

Primer information

| Gene name | Primer pool | Primer No. | Sequences of Primers (5'-3') |
|---|---|---|---|
| HBV-C | GSP2A | HA2040 | CTTGGCACCCGAGAATTCCACCGTTTGGGACTCTACCGT (SEQ ID NO: 222) |
| HBV-C | GSP2A | HA2041 | CTTGGCACCCGAGAATTCCACGTGTGCACTTCGCTTCA (SEQ ID NO: 223) |
| HBV-C | GSP2A | HA2042 | CTTGGCACCCGAGAATTCCATTGCCCAAGGTCTTACATAAGAGG (SEQ ID NO: 224) |
| HBV-C | GSP2A | HA2043 | CTTGGCACCCGAGAATTCCAGTTTGTTTAAGGACTGGGAGGAGTT (SEQ ID NO: 225) |
| HBV-C | GSP2A | HA2044 | CTTGGCACCCGAGAATTCCAGGTCTGTTCACCAGCACCATG (SEQ ID NO: 226) |
| HBV-C | GSP2A | HA2045 | CTTGGCACCCGAGAATTCCACTGTGCCTTGGGTGGCTT (SEQ ID NO: 227) |
| HBV-C | GSP2A | HA2046 | CTTGGCACCCGAGAATTCCATTGCCTTCTGATTTCTTTCCTTCTATT (SEQ ID NO: 228) |
| HBV-C | GSP2A | HA2047 | CTTGGCACCCGAGAATTCCAGAGTCTCCGGAACATTGTTCACC (SEQ ID NO: 229) |
| HBV-C | GSP2A | HA2048 | CTTGGCACCCGAGAATTCCAAGTTGATGAATCTGGCCACCT (SEQ ID NO: 230) |
| HBV-C | GSP2A | HA2049 | CTTGGCACCCGAGAATTCCACAGCTATGTTAATGTTAATATGGGCCTA (SEQ ID NO: 231) |
| HBV-C | GSP2A | HA2050 | CTTGGCACCCGAGAATTCCATATTTGGTGTCTTTTGGAGTGTGGAT (SEQ ID NO: 232) |
| HBV-C | GSP2A | HA2051 | CTTGGCACCCGAGAATTCCATAGAGGCAGGTCCCCTAGAAG (SEQ ID NO: 233) |
| HBV-C | GSP2A | HA2052 | CTTGGCACCCGAGAATTCCACAATGTTAGTATCCCTTGGACTCACA (SEQ ID NO: 234) |
| HBV-C | GSP2A | HA2053 | CTTGGCACCCGAGAATTCCAACAGGAGGACATTATTGATAGATGTCA (SEQ ID NO: 235) |
| HBV-C | GSP2A | HA2054 | CTTGGCACCCGAGAATTCCAAACCTTACCAAGTATTTGCCCTT (SEQ ID NO: 236) |
| HBV-C | GSP2A | HA2055 | CTTGGCACCCGAGAATTCCATCTGTGGAAGGCTGGGATTCTATAT (SEQ ID NO: 237) |
| HBV-C | GSP2A | HA2056 | CTTGGCACCCGAGAATTCCAGGGACAAATCTTTCTGTTCCCA (SEQ ID NO: 238) |
| HBV-C | GSP2A | HA2057 | CTTGGCACCCGAGAATTCCAGGCCAGAGGCAAATCAGGT (SEQ ID NO: 239) |
| HBV-C | GSP2A | HA2058 | CTTGGCACCCGAGAATTCCACAGTCAGGAAGACAGCCTACTC (SEQ ID NO: 240) |
| HBV-B | GSP2A | HA2059 | CTTGGCACCCGAGAATTCCAAATACTGTCTCTGCCATATCGTCA (SEQ ID NO: 241) |
| HBV-B | GSP2A | HA2060 | CTTGGCACCCGAGAATTCCAGTGTGTTTCATGAGTGGGAGGA (SEQ ID NO: 242) |
| HBV-B | GSP2A | HA2061 | NA |
| HBV-B | GSP2A | HA2062 | NA |
| HBV-B | GSP2A | HA2063 | NA |
| HBV-B | GSP2A | HA2064 | CTTGGCACCCGAGAATTCCATTTGCCTTCTGACTTCTTTCCGTC (SEQ ID NO: 243) |
| HBV-B | GSP2A | HA2065 | CTTGGCACCCGAGAATTCCACACAGCACTCAGGCAAGCTA (SEQ ID NO: 244) |
| TP53 | GSP2A | HA2071 | CTTGGCACCCGAGAATTCCAGTCACTGCCATGGAGGAGC (SEQ ID NO: 245) |
| TP53 | GSP2A | HA2072 | CTTGGCACCCGAGAATTCCACCATGGGACTGACTTTCTGC (SEQ ID NO: 246) |
| TP53 | GSP2A | HA2073 | CTTGGCACCCGAGAATTCCAACTGCTCTTTTCACCCATCTACA (SEQ ID NO: 247) |
| TP53 | GSP2A | HA2074 | CTTGGCACCCGAGAATTCCATGTCCCCGGACGATATTGAAC (SEQ ID NO: 248) |
| TP53 | GSP2A | HA2075 | CTTGGCACCCGAGAATTCCACAGATGAAGCTCCCAGAATGCC (SEQ ID NO: 249) |
| TP53 | GSP2A | HA2076 | CTTGGCACCCGAGAATTCCATGTCATCTTCTGTCCCTTCCCA (SEQ ID NO: 250) |
| TP53 | GSP2A | HA2077 | CTTGGCACCCGAGAATTCCACAACTCTGTCTCCTTCCTCTTCCT (SEQ ID NO: 251) |
| TP53 | GSP2A | HA2078 | CTTGGCACCCGAGAATTCCATGTGCAGCTGTGGGTTGAT (SEQ ID NO: 252) |

TABLE 11-continued

Primer information

| Gene name | Primer pool | Primer No. | Sequences of Primers (5'-3') |
|---|---|---|---|
| TP53 | GSP2A | HA2079 | CTTGGCACCCGAGAATTCCACAAGCAGTCACAGCACATGACG (SEQ ID NO: 253) |
| TP53 | GSP2A | HA2080 | CTTGGCACCCGAGAATTCCACCTCTGATTCCTCACTGATTGCT (SEQ ID NO: 254) |
| TP53 | GSP2A | HA2081 | CTTGGCACCCGAGAATTCCATTGCGTGTGGAGTATTTGGATG (SEQ ID NO: 255) |
| TP53 | GSP2A | HA2082 | CTTGGCACCCGAGAATTCCATCTTGGGCCTGTGTTATCTCCT (SEQ ID NO: 256) |
| TP53 | GSP2A | HA2083 | CTTGGCACCCGAGAATTCCAACATGTGTAACAGTTCCTGCATGG (SEQ ID NO: 257) |
| TP53 | GSP2A | HA2084 | CTTGGCACCCGAGAATTCCACTTGCTTCTCTTTTCCTATCCTGAGT (SEQ ID NO: 258) |
| TP53 | GSP2A | HA2085 | CTTGGCACCCGAGAATTCCACTTTGAGGTGCGTGTTTGTGC (SEQ ID NO: 259) |
| TP53 | GSP2A | HA2086 | CTTGGCACCCGAGAATTCCAGCAAGAAAGGGGAGCCTCA (SEQ ID NO: 260) |
| TP53 | GSP2A | HA2087 | CTTGGCACCCGAGAATTCCAATCACCTTTCCTTGCCTCTTTCC (SEQ ID NO: 261) |
| TP53 | GSP2A | HA2088 | CTTGGCACCCGAGAATTCCATTCTCCCCCTCCTCTGTTGC (SEQ ID NO: 262) |
| TP53 | GSP2A | HA2089 | CTTGGCACCCGAGAATTCCACTTCGAGATGTTCCGAGAGCT (SEQ ID NO: 263) |
| TP53 | GSP2A | HA2090 | CTTGGCACCCGAGAATTCCACCTCCCTGCTTCTGTCTCCTA (SEQ ID NO: 264) |
| TP53 | GSP2A | HA2091 | CTTGGCACCCGAGAATTCCATCAGTCTACCTCCCGCCATA (SEQ ID NO: 265) |
| AXIN1 | GSP2B | HB2009 | CTTGGCACCCGAGAATTCCAGAAACTTGCTCCGAGGTCCA (SEQ ID NO: 266) |
| AXIN1 | GSP2B | HB2010 | CTTGGCACCCGAGAATTCCACATCCAGCAGGGAATGCAGT (SEQ ID NO: 267) |
| AXIN1 | GSP2B | HB2011 | CTTGGCACCCGAGAATTCCAGACACGATGCCATTGTTATCAAGA (SEQ ID NO: 268) |
| AXIN1 | GSP2B | HB2012 | CTTGGCACCCGAGAATTCCACTGTCTCCAGGAGCAGCTTC (SEQ ID NO: 269) |
| AXIN1 | GSP2B | HB2013 | CTTGGCACCCGAGAATTCCACGGAGGTGAGTACAGAAAGTGG (SEQ ID NO: 270) |
| AXIN1 | GSP2B | HB2014 | CTTGGCACCCGAGAATTCCAGGAGGCAGCTTGTGACACG (SEQ ID NO: 271) |
| AXIN1 | GSP2B | HB2015 | CTTGGCACCCGAGAATTCCACTCGTCCAGGATGCTCTCAG (SEQ ID NO: 272) |
| AXIN1 | GSP2B | HB2016 | CTTGGCACCCGAGAATTCCAGTGGTGGACGTGGTGGTG (SEQ ID NO: 273) |
| AXIN1 | GSP2B | HB2017 | CTTGGCACCCGAGAATTCCATGATTTTCTGGTTCTTCTCCGCAT (SEQ ID NO: 274) |
| CTNNB1 | GSP2B | HB2018 | CTTGGCACCCGAGAATTCCAGAGGTATCCACATCCTCTTCCTCA (SEQ ID NO: 275) |
| TERT | GSP2B | HB2019 | CTTGGCACCCGAGAATTCCAAGGACTTCCCAGGAATCCAG (SEQ ID NO: 276) |
| TERT | GSP2B | HB2020 | CTTGGCACCCGAGAATTCCAAGCTAGGAGGCCCGACTT (SEQ ID NO: 277) |
| TERT | GSP2B | HB2021 | CTTGGCACCCGAGAATTCCAACAACGGCCTTGACCCTG (SEQ ID NO: 278) |
| TERT | GSP2B | HB2022 | CTTGGCACCCGAGAATTCCACCACCCCAAATCTGTTAATCACC (SEQ ID NO: 279) |
| TERT | GSP2B | HB2023 | CTTGGCACCCGAGAATTCCAAACACTTCCCCGCGACTTGG (SEQ ID NO: 280) |
| TERT | GSP2B | HB2024 | CTTGGCACCCGAGAATTCCACGTGAAGGGGAGGACGGA (SEQ ID NO: 281) |
| TERT | GSP2B | HB2025 | CTTGGCACCCGAGAATTCCAGGGGCCATGATGTGGAGG (SEQ ID NO: 282) |
| TERT | GSP2B | HB2026 | CTTGGCACCCGAGAATTCCAAAGGTGAAGGGGCAGGAC (SEQ ID NO: 283) |
| TERT | GSP2B | HB2027 | CTTGGCACCCGAGAATTCCAGCGGAAAGGAAGGGGAGG (SEQ ID NO: 284) |
| TERT | GSP2B | HB2028 | CTTGGCACCCGAGAATTCCAGCAGCACCTCGCGGTAG (SEQ ID NO: 285) |
| HBV-C | GSP2B | HB2029 | CTTGGCACCCGAGAATTCCAGGAAAGTATAGGCCCCTCACTC (SEQ ID NO: 286) |
| HBV-C | GSP2B | HB2030 | CTTGGCACCCGAGAATTCCACTCTCCATGTTCGGGCA (SEQ ID NO: 287) |
| HBV-C | GSP2B | HB2031 | CTTGGCACCCGAGAATTCCAGAGGATTCTTGTCAACAAGAAAACCC (SEQ ID NO: 288) |
| HBV-C | GSP2B | HB2032 | CTTGGCACCCGAGAATTCCAACAAGAGGTTGGTGAGTGATTGG (SEQ ID NO: 289) |

TABLE 11-continued

Primer information

| Gene name | Primer pool | Primer No. | Sequences of Primers (5'-3') |
|---|---|---|---|
| HBV-C | GSP2B | HB2033 | CTTGGCACCCGAGAATTCCAGTCCAGAAGAACCAACAAGAAGATGA (SEQ ID NO: 290) |
| HBV-C | GSP2B | HB2034 | CTTGGCACCCGAGAATTCCACATAGAGGTTCCTTGAGCAGGAATC (SEQ ID NO: 291) |
| HBV-C | GSP2B | HB2035 | CTTGGCACCCGAGAATTCCACACTCCCATAGGAATCTTGCGAA (SEQ ID NO: 292) |
| HBV-C | GSP2B | HB2036 | CTTGGCACCCGAGAATTCCACCCCCAATACCACATCATCCATA (SEQ ID NO: 293) |
| HBV-C | GSP2B | HB2037 | CTTGGCACCCGAGAATTCCAAGGGTTCAAATGTATACCCAAAGACAA (SEQ ID NO: 294) |
| HBV-C | GSP2B | HB2038 | CTTGGCACCCGAGAATTCCAAGTTTTAGTACAATATGTTCTTGCGGTA (SEQ ID NO: 295) |
| HBV-C | GSP2B | HB2039 | CTTGGCACCCGAGAATTCCACATTGTGTAAAAGGGGCAGCA (SEQ ID NO: 296) |
| HBV-C | GSP2B | HB2040 | CTTGGCACCCGAGAATTCCATGTTTACACAGAAAGGCCTTGTAAGT (SEQ ID NO: 297) |
| HBV-C | GSP2B | HB2041 | CTTGGCACCCGAGAATTCCACATGCGGCGATGGCCAATA (SEQ ID NO: 298) |
| HBV-C | GSP2B | HB2042 | CTTGGCACCCGAGAATTCCATTCCGAGAGAGGACAACAGAGTTGT (SEQ ID NO: 299) |
| HBV-C | GSP2B | HB2043 | CTTGGCACCCGAGAATTCCAGACGGGACGTAAACAAAGGAC (SEQ ID NO: 300) |
| HBV-C | GSP2B | HB2044 | CTTGGCACCCGAGAATTCCAGGAGACCGCGTAAAGAGAGG (SEQ ID NO: 301) |
| HBV-C | GSP2B | HB2045 | CTTGGCACCCGAGAATTCCAGTGCAGAGGTGAAGCGAAGT (SEQ ID NO: 302) |
| HBV-C | GSP2B | HB2046 | CTTGGCACCCGAGAATTCCATCCAAGAGTCCTCTTATGTAAGACC (SEQ ID NO: 303) |
| HBV-C | GSP2B | HB2047 | CTTGGCACCCGAGAATTCCACAACTCCTCCCAGTCCTTAAACA (SEQ ID NO: 304) |
| HBV-C | GSP2B | HB2048 | CTTGGCACCCGAGAATTCCAGGTGCTGGTGAACAGACCAA (SEQ ID NO: 305) |
| HBV-C | GSP2B | HB2049 | CTTGGCACCCGAGAATTCCACTTGGAGGCTTGAACAGTAGGA (SEQ ID NO: 306) |
| HBV-C | GSP2B | HB2050 | CTTGGCACCCGAGAATTCCAAATTCTTTATACGGGTCAATGTCCA (SEQ ID NO: 307) |
| HBV-C | GSP2B | HB2051 | CTTGGCACCCGAGAATTCCACAGAGGCGGTGTCGAGGA (SEQ ID NO: 308) |
| HBV-C | GSP2B | HB2052 | CTTGGCACCCGAGAATTCCAACACAGAACAGCTTGCCTGA (SEQ ID NO: 309) |
| HBV-C | GSP2B | HB2053 | CTTGGCACCCGAGAATTCCACTGGGTCTTCCAAATTACTTCCCA (SEQ ID NO: 310) |
| HBV-C | GSP2B | HB2054 | CTTGGCACCCGAGAATTCCAGTTTCTCTTCCAAAGGTAAGACAGGA (SEQ ID NO: 311) |
| HBV-C | GSP2B | HB2055 | CTTGGCACCCGAGAATTCCAACCTGCCTCTACGTCTAACAACA (SEQ ID NO: 312) |
| HBV-C | GSP2B | HB2056 | CTTGGCACCCGAGAATTCCATTGTGAGTCCAAGGGATACTAACATTG (SEQ ID NO: 313) |
| HBV-C | GSP2B | HB2057 | CTTGGCACCCGAGAATTCCAGGGAGTTTGCCACTCAGGATTAAA (SEQ ID NO: 314) |
| HBV-C | GSP2B | HB2058 | CTTGGCACCCGAGAATTCCAGGGCAAATACTTGGTAAGGTTAGGATA (SEQ ID NO: 315) |
| HBV-C | GSP2B | HB2059 | CTTGGCACCCGAGAATTCCACCTTCCACAGAGTATGTAAATAATGCCTA (SEQ ID NO: 316) |
| HBV-C | GSP2B | HB2060 | CTTGGCACCCGAGAATTCCACTCCCATGCTGTAGCTCTTGTT (SEQ ID NO: 317) |
| HBV-C | GSP2B | HB2061 | CTTGGCACCCGAGAATTCCAGCTGGGTCCAACTGGTGATC (SEQ ID NO: 318) |
| HBV-C | GSP2B | HB2062 | CTTGGCACCCGAGAATTCCACCCCAAAAGACCACCGTGTG (SEQ ID NO: 319) |
| HBV-C | GSP2B | HB2063 | CTTGGCACCCGAGAATTCCATCTTCCTGACTGCCGATTGGT (SEQ ID NO: 320) |
| HBV-B | GSP2B | HB2064 | NA |
| HBV-B | GSP2B | HB2065 | NA |
| HBV-B | GSP2B | HB2066 | CTTGGCACCCGAGAATTCCACAAGACCTTGGGCAGGTTCC (SEQ ID NO: 321) |
| HBV-B | GSP2B | HB2067 | CTTGGCACCCGAGAATTCCAATTCTAAGGCTTCCCGATACAGA (SEQ ID NO: 322) |
| HBV-B | GSP2B | HB2068 | CTTGGCACCCGAGAATTCCAACGCTGGATCTTCTAAATTATTACCC (SEQ ID NO: 323) |

TABLE 11-continued

Primer information

| Gene name | Primer pool | Primer No. | Sequences of Primers (5'-3') |
|---|---|---|---|
| HBV-B | GSP2B | HB2069 | NA |
| TP53 | GSP2B | HB2071 | CTTGGCACCCGAGAATTCCAGATCCACTCACAGTTTCCATAGG (SEQ ID NO: 324) |
| TP53 | GSP2B | HB2072 | CTTGGCACCCGAGAATTCCACAGCCCAACCCTTGTCCTTA (SEQ ID NO: 325) |
| TP53 | GSP2B | HB2073 | CTTGGCACCCGAGAATTCCATGGGAGCTTCATCTGGACCTG (SEQ ID NO: 326) |
| TP53 | GSP2B | HB2074 | CTTGGCACCCGAGAATTCCAGAAGGGACAGAAGATGACAGG (SEQ ID NO: 327) |
| TP53 | GSP2B | HB2075 | CTTGGCACCCGAGAATTCCACAAGAAGCCCAGACGGAAACC (SEQ ID NO: 328) |
| TP53 | GSP2B | HB2076 | CTTGGCACCCGAGAATTCCACCCCTCAGGGCAACTGAC (SEQ ID NO: 329) |
| TP53 | GSP2B | HB2077 | CTTGGCACCCGAGAATTCCAGTGCTGTGACTGCTTGTAGATGGC (SEQ ID NO: 330) |
| TP53 | GSP2B | HB2078 | CTTGGCACCCGAGAATTCCAATCTGAGCAGCGCTCATGGTG (SEQ ID NO: 331) |
| TP53 | GSP2B | HB2079 | CTTGGCACCCGAGAATTCCACCCTGTCGTCTCTCCAGC (SEQ ID NO: 332) |
| TP53 | GSP2B | HB2080 | CTTGGCACCCGAGAATTCCACTATGTCGAAAAGTGTTTCTGTCATCC (SEQ ID NO: 333) |
| TP53 | GSP2B | HB2081 | CTTGGCACCCGAGAATTCCAGAGACCCCAGTTGCAAACCAG (SEQ ID NO: 334) |
| TP53 | GSP2B | HB2082 | CTTGGCACCCGAGAATTCCATGGGCCTCCGGTTCATGC (SEQ ID NO: 335) |
| TP53 | GSP2B | HB2083 | CTTGGCACCCGAGAATTCCAGTGCAGGGTGGCAAGTGG (SEQ ID NO: 336) |
| TP53 | GSP2B | HB2084 | CTTGGCACCCGAGAATTCCAGACAGGCACAAACACGCAC (SEQ ID NO: 337) |
| TP53 | GSP2B | HB2085 | CTTGGCACCCGAGAATTCCATTCTTGCGGAGATTCTCTTCCTCT (SEQ ID NO: 338) |
| TP53 | GSP2B | HB2086 | CTTGGCACCCGAGAATTCCACGCTTCTTGTCCTGCTTGCT (SEQ ID NO: 339) |
| TP53 | GSP2B | HB2087 | CTTGGCACCCGAGAATTCCAACTTGATAAGAGGTCCCAAGACTTAG (SEQ ID NO: 340) |
| TP53 | GSP2B | HB2088 | CTTGGCACCCGAGAATTCCAAGCCTGGGCATCCTTGAG (SEQ ID NO: 341) |
| TP53 | GSP2B | HB2089 | CTTGGCACCCGAGAATTCCACAGGAAGGGGCTGAGGTC (SEQ ID NO: 342) |
| TP53 | GSP2B | HB2090 | CTTGGCACCCGAGAATTCCACATGAGTTTTTTATGGCGGGAGGT (SEQ ID NO: 343) |
| TP53 | GSP2B | HB2091 | CTTGGCACCCGAGAATTCCACAGTGGGGAACAAGAAGTGGA (SEQ ID NO: 344) |

Wherein NA means no primer.

TABLE 12

Reaction procedures

| Temperature | Time | Number of cycles |
|---|---|---|
| 98° C. | 3 min | |
| 98° C. | 15 s | 9 cycles |
| 60° C. | 90 s | |
| 72° C. | 90 s | |
| 98° C. | 15 s | 8 cycles |
| 60° C. | 30 s | |
| 72° C. | 30 s | |
| 72° C. | 10 min | |

4. The product obtained in step 3 for the second cycle of amplification using GSP2A mix and the product of the second cycle of amplification using GSP1B mix are mixed in equal volumes, and purified with AMPure XP magnetic beads at a ratio of 1:1.3, eluted with 50 μl DNase/RNase-Free Water to obtain the second cycle of purified products, which are sequencing libraries that may be sequenced on the Illumina Hiseq X platform. The amount of sequencing data of each library is 2G, and the average sequencing depth is greater than 60000×.

The DNA random tag of the MC library is added to the downstream of the Read1 sequence of the sequencing library together with the cfDNA sequence. In sequencing, a DNA random tag sequence, an anchor sequence, a cfDNA sequence (c, d, e sequence in FIG. 1) are obtained sequentially. During data analysis, backtrack the sequencing data of DNA molecules with the same random tag sequence, the same length of the DNA insert, and the same breakpoints at both ends of the DNA insert to a molecular cluster. If the number of molecules in the cluster is greater than 5 and the consistency rate of molecular mutations in the cluster is greater than 80% and the number of clusters is greater than or equal to 5, the mutation is a true mutation from the original DNA sample.

Sequencing experiments with 30 ng liver cancer patients' cfDNA show that this method only takes about 6 hours in total (about 1.5 h manual operation), and the target rate of the RaceSeq library generated reaches 80%. With 2 Gb data, the sequencing depth reaches 60,000×, the number of molecular clusters is 5000, and the average number of sequenced molecules per cluster reaches 12, see Table 13 for details.

TABLE 13

Sequencing data display

| Target Region: 20031 bp | Sample No. | | | |
|---|---|---|---|---|
| | RG773 | RG774 | RG776 | RG777 |
| Start amount of Sample (ng) | 30 | 30 | 30 | 30 |
| MC library production (ng) | 6800 | 7300 | 7200 | 6500 |
| Amount sequenced (bp) | 2002633889 | 1733018642 | 1725428157 | 1790632086 |
| Genomic alignment rate | 0.9888 | 0.9896 | 0.9907 | 0.9896 |
| Target rate | 0.8015 | 0.8057 | 0.8295 | 0.7877 |
| Sequencing depth | 80130.55 | 69705.42 | 71452.26 | 70411.13 |

Example 3. Capture and Sequencing of MC Library

Figure 3:
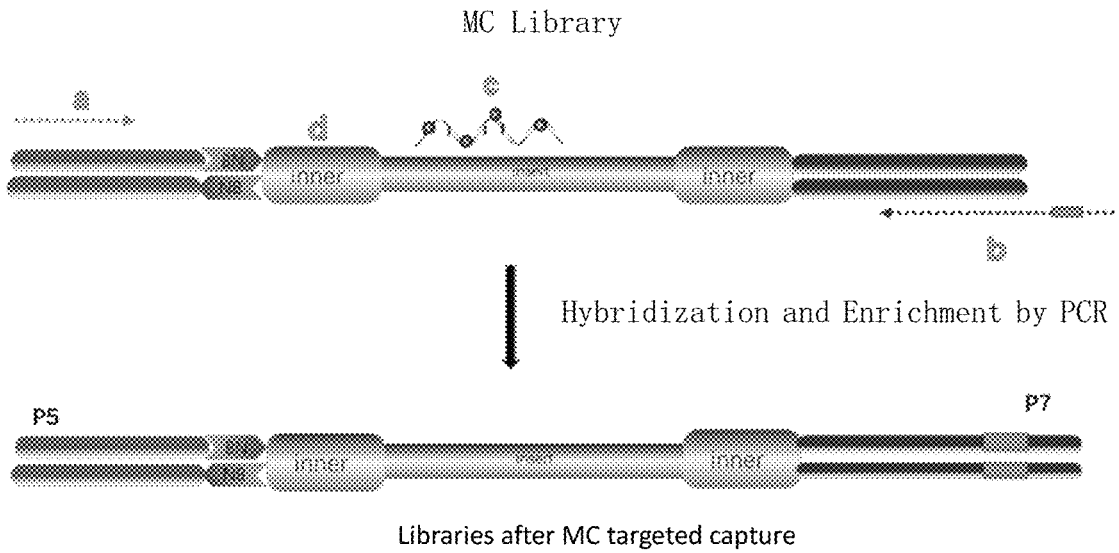
FIG. 3 is a schematic diagram of capture and duplex sequencing by MC library.

As shown in FIG. 3, the Agilent sureselect XT target capture kit (Agilent5190-8646) may be used to capture the MC library in Example 1 (refer to the kit instructions, and compatible with other brands of capture reagents), replace the primers in the last step of PCR amplification with the following primers:
Upstream primer (5'-3'): AATGATACGGCGAC-CACCGAGATCTACACTCTTTCCCTA-CACGACGCTCTTCC GATCT (SEQ ID NO: 345) ("a" in FIG. 3), the underlined part is the same as the primer MC_F, which is used to amplify the library, and the remaining parts are the fixed sequences required for sequencing on the Illumina sequencing platform.
Downstream primer (5'-3'): CAAGCAGAAGACGG-CATACGAGAT (SEQ ID NO: 346) ******GTCTCGTGGGCTCGGAGATGTGTATAA (SEQ ID NO: 347) ("b" in FIG. 3), the underlined part is the same as the primer MC_R, which is used for amplification library. ****** is the position of the index sequence, the length of the index is 6-8 bp, which is used to distinguish the sequence between samples and facilitate the mixed sequencing of multiple samples. The remaining parts are the fixed sequences required for sequencing on the Illumina sequencing platform.

The captured library and MC library have the same DNA random tag sequence, anchor sequence and cfDNA sequence, which are located downstream of Read1 sequentially. Backtrack the sequencing data of the starting single-stranded DNA with the same length of the DNA insert, the same breakpoints at both ends of the DNA insert, and the same anchor sequence at both ends to a molecular cluster. At the same time, a starting double-stranded DNA molecular cluster, which has the same length of the DNA insert, the same sequence except for the mutation point, the same anchor sequence at both ends of the molecular cluster except for the opposite position, is labeled as a pair of duplex molecular clusters. For a certain mutation, if there is at least one pair of duplex molecular cluster supported, it may be judged as true. If there is no duplex molecular cluster supported, it may be judged as true if there are at least 4 molecular clusters supported. The reliability of mutations supported by a pair of duplex molecular clusters is higher and may reduce 90% of false positive mutations.

Example 4. Method Comparison

Collect 5 cases of liver cancer cfDNA specimens, construct the MC library according to the method in Example 1 firstly, and then perform the RaceSeq an enrichment of a target region according to the method in Example 2 and region enrichment, sequencing according to the conventional Agilent sureselect XT target in Example 3, and mutation detection results are shown in Table 13 and Table 14.

TABLE 13

Comparison of two methods of snv detection

| Detection results | Specimen No. | Mutation Frequency | Genes | Positions of Bases | Reference Type | Mutant Type |
|---|---|---|---|---|---|---|
| consistent | RG773 | 0.0013 | TERT | 1295073 | C | T |
| consistent | RG773 | 0.0009 | AXIN1 | 396583 | T | A |
| consistent | RG773 | 0.0025 | TP53 | 7577539 | G | A |
| consistent | RG775 | 0.0800 | TP53 | 7577534 | C | A |
| consistent | RG776 | 0.0010 | AXIN1 | 347927 | C | T |
| consistent | RG776 | 0.0024 | TP53 | 7577534 | C | A |

TABLE 14

Comparison of HBV fusion detection between two methods

| Detection Method | Specimen No. | Gene (Human) | The chromosome number_ Breakpoint on the right side | Position of bases_ Breakpoint on the right side | Subtypes of Virus | Position of bases _ Breakpoint on the left side | Fusion Frequency | Results |
|---|---|---|---|---|---|---|---|---|
| Capture | RG774 | PKDCC (dist = 5233), LOC102723824(dist = 78674) | 2 | 42290901 | HBV_C | 851 | 0.08 | consistent |

TABLE 14-continued

Comparison of HBV fusion detection between two methods

| Detection Method | Specimen No. | Gene (Human) | The chromosome number_ Breakpoint on the right side | Position of bases_ Breakpoint on the right side | Subtypes of Virus | Position of bases _ Breakpoint on the left side | Fusion Frequency | Results |
|---|---|---|---|---|---|---|---|---|
| Race-seq | RG774 | PKDCC (dist = 5233), LOC102723824(dist = 78674) | 2 | 42290906 | HBV_C | 851 | 0.11 | |
| Capture | RG774 | SNTG1 (dist = 351419), PXDNL (dist = 174040) | 8 | 52058097 | HBV_C | 1811 | 0.15 | consistent |
| Race-seq | RG774 | SNTG1 (dist = 351419), PXDNL (dist = 174040) | 8 | 52058096 | HBV_C | 1811 | 0.06 | |

It may be seen that the Agilent sureselect XT target region enrichment method and the RaceSeq method have basically the same detection results for single-base mutation and HBV insertion.

INDUSTRIAL APPLICATION

The inventors of the present invention have obtained a primer combination for detecting mutations in liver cancer from a DNA sample through a large number of experiments. The primer combination consists of a primer set I, a primer set II, a primer set III and a primer set IV. The primer set I consists of the single-stranded DNA shown as SEQ ID NO: 28 to SEQ ID NO: 105 in the sequence listing. The primer set II consists of the single-stranded DNA shown as SEQ ID NO: 106 to SEQ ID NO: 187 in the sequence listing. The primer set III consists of the single-stranded DNA shown as SEQ ID NO: 191 to the SEQ ID NO: 265 in the sequence listing. The primer set IV consists of the single-stranded DNA shown as SEQ ID NO: 266 to SEQ ID NO: 344 in the sequence listing. Experiments have proved that the above-mentioned primer combination may simultaneously detect multiple mutation forms such as point mutations, insert and indel mutations, and HBV integration in liver cancer ctDNA without capturing. As there is no need for expensive capture probes and hybridization reagents, the cost is greatly reduced, and the operation process is simple, and the detection time is only 8 hours. The invention has important clinical significance for early screening, disease tracking, efficacy evaluation, prognosis prediction and the like of liver cancer.

What is claimed:

1. A method for constructing a sequencing library, including the following steps sequentially:
   (1) perform an end repairing and 3' end treatment of adding a base A in a DNA sample sequentially;
   (2) ligate the DNA sample treated in step (1) to an adapter mixture, and obtain a library after PCR amplification;
   the adapter mixture consists of 12 adapters;
   each adapter is obtained by forming a partially double-stranded structure from an upstream primer A and a downstream primer A; the upstream primer A has a sequencing adapter, a random tag, an anchor sequence A and a base T at the 3' end from 5' to 3' order; the downstream primer A has an anchor sequence B and a sequencing adapter B from 5' to 3' order; the partially double-stranded structure is formed by the reverse complementation of the anchor sequence A in the upstream primer and the anchor sequence B in the downstream primer;
   the sequencing adapter A and the sequencing adapter B are corresponding adapters selected according to different sequencing platforms;
   the random tag is random bases of 8-14 bp;
   the length of the anchor sequence A is 14-20 bp, and the number of consecutive repeated bases is less than or equal to 3;
   the 12 adapters use 12 different anchor sequences, the bases at the same position are balanced, and the number of mismatched bases is greater than 3; and
   wherein the nucleotide sequence of the anchor sequence A is specifically shown as positions 30-41 of SEQ ID NO: 1 from the 5' end in the sequence listing, positions 30-41 of SEQ ID NO: 3 from the 5' end in the sequence listing, positions 30-41 of SEQ ID NO: 5 from the 5' end in the sequence listing, positions 30-41 of SEQ ID NO: 7 from the 5' end in the sequence listing, positions 30-41 of SEQ ID NO: 9 from the 5' end in the sequence listing, positions 30-41 of SEQ ID NO: 11 from the 5' end in the sequence listing, positions 30-41 of SEQ ID NO: 13 from the 5' end in the sequence listing, positions 30-41 of SEQ ID NO: 15 from the 5' end in the sequence listing, positions 30-41 of SEQ ID NO: 17 from the 5' end in the sequence listing, positions 30-41 of SEQ ID NO: 19 from the 5' end in the sequence listing, positions 30-41 of SEQ ID NO: 21 from the 5' end in the sequence listing, positions 30-41 of SEQ ID NO: 23 from the 5' end, respectively;
   the adapter 1 is obtained from a partially double-stranded structure formed by a single-stranded DNA molecule shown as SEQ ID NO: 1 and a single-stranded DNA molecule shown as SEQ ID NO: 2 in the sequence listing;
   the adapter 2 is obtained from a partially double-stranded structure formed by a single-stranded DNA molecule shown as SEQ ID NO: 3 in the sequence listing and a single-stranded DNA molecule shown as SEQ ID NO: 4 in the sequence listing;
   the adapter 3 is obtained from a partially double-stranded structure formed by a single-stranded DNA molecule shown as SEQ ID NO: 5 in the sequence listing and a single-stranded DNA molecule shown as SEQ ID NO: 6 in the sequence listing;

the adapter 4 is obtained from a partially double-stranded structure formed by a single-stranded DNA molecule shown as SEQ ID NO: 7 in the sequence listing and a single-stranded DNA molecule shown as SEQ ID NO: 8 in the sequence listing;

the adapter 5 is obtained from a partially double-stranded structure formed by a single-stranded DNA molecule shown as SEQ ID NO: 9 in the sequence listing and a single-stranded DNA molecule shown as SEQ ID NO: 10 in the sequence listing;

the adapter 6 is obtained from a partially double-stranded structure formed by a single-stranded DNA molecule shown as SEQ ID NO: 11 in the sequence listing and a single-stranded DNA molecule shown as SEQ ID NO: 12 in the sequence listing;

the adapter 7 is obtained from a partially double-stranded structure formed by a single-stranded DNA molecule shown as SEQ ID NO: 13 in the sequence listing and a single-stranded DNA molecule shown as SEQ ID NO: 14 in the sequence listing;

the adapter 8 is obtained from a partially double-stranded structure formed by a single-stranded DNA molecule shown as SEQ ID NO: 15 in the sequence listing and a single-stranded DNA molecule shown as SEQ ID NO: 16 in the sequence listing;

the adapter 9 is obtained from a partially double-stranded structure formed by a single-stranded DNA molecule shown as SEQ ID NO: 17 in the sequence listing and a single-stranded DNA molecule shown as SEQ ID NO: 18 in the sequence listing;

the adapter 10 is obtained from a partially double-stranded structure formed by a single-stranded DNA molecule shown as SEQ ID NO: 19 in the sequence listing and a single-stranded DNA molecule shown as SEQ ID NO: 20 in the sequence listing;

the adapter 11 is obtained from a partially double-stranded structure formed by a single-stranded DNA molecule shown as SEQ ID NO: 21 in the sequence listing and a single-stranded DNA molecule shown as SEQ ID NO: 22 in the sequence listing; and the adapter 12 is obtained from a partially double-stranded structure formed by a single-stranded DNA molecule shown as SEQ ID NO: 23 in the sequence listing and a single-stranded DNA molecule shown as SEQ ID NO: 24 in the sequence listing.

2. The method of claim 1, wherein the method further comprises a step of amplifying the library obtained in step (2).

3. Method of claim 2, wherein the primer pair used in the amplification consists of two single-stranded DNA molecules shown as SEQ ID NO: 25 and SEQ ID NO: 26 in the sequence listing.

4. A kit for constructing a sequencing library, comprising the adapter mixture defined in claim 1.

5. A kit for detecting mutations in liver cancer from a DNA sample, comprising the adapter mixture defined in claim 1 and a primer combination; the primer combination comprises a primer set I, a primer set II, a primer set III and a primers set IV;

each primer in the primer set I and the primer set II is a specific primer designed according to a region related to liver cancer, and its role is to locate at a specific position in the genome to achieve enrichment of the target region by PCR;

the nucleotide sequence of each primer in the primer set III and the primer set IV consists of "an adapter sequence+a specific sequence", the specific sequence is used for further enrichment of the target region, and the adapter sequence is used to form a complete library molecules that may be sequenced;

the primer set III and the primer set I may be in a "nested" relationship; the primer set IV and the primer set II may be in a "nested" relationship.

6. The kit of claim 5, wherein:

the primer set I consists of a single-stranded DNA shown as SEQ ID NO: 28 to SEQ ID NO: 105 in the sequence listing;

the primer set II consists of a single-stranded DNA shown as SEQ ID NO: 106 to SEQ ID NO: 187 in the sequence listing;

the primer set III consists of a single-stranded DNA shown as SEQ ID NO: 191 to SEQ ID NO: 265 in the sequence listing;

the primer set IV consists of a single-stranded DNA shown as SEQ ID NO: 266 to SEQ ID NO: 344 in the sequence listing.

7. A method for detecting a target mutation in a DNA sample, including the following steps:

(1) construct a library according to the method of claim 1;

(2) perform two cycles of nested PCR amplification on the library obtained in step (1), sequence the products, and analyze the occurrence of the target mutation in the DNA sample according to the sequencing results;

in step (2), the first cycle of PCR amplification is performed by using a primer combination A;

the primer combination A consists of an upstream primer A and a downstream primer combination A;

the upstream primer A is a library amplification primer used for the library amplification in step (1);

the downstream primer combination A is a combination of M primers designed according to M target points;

using the product of the first cycle of PCR as a template, perform the second cycle of PCR amplification with a primer combination B;

the primer combination B consists of an upstream primer B, a downstream primer combination B and an index primer;

the upstream primer B is a library amplification primer used for the amplification of the product of the first cycle of PCR;

the primers in the downstream primer combination B and the primers in the downstream primer combination A for detecting the same target form a nested relationship, and each upstream primer B and each downstream primer combination B has a segment that binds to the index primer;

the index primer contains a segment that binds to each primer in the downstream primer combination B and the index sequence;

wherein the nucleotide sequence of the upstream primer A is shown as SEQ ID NO: 27 in the sequence listing;

the nucleotide sequence of the upstream primer B is shown as SEQ ID NO: 188 in the sequence listing;

the index primer comprises a segment A, an index sequence and a segment B from the 5' end; the nucleotide sequence of segment A is shown as SEQ ID NO: 189 in the sequence listing, and the nucleotide sequence of segment B is shown as SEQ ID NO: 190 in the sequence listing.

8. The method of claim 7, wherein:

when the target mutation is a mutation in liver cancer, the primer combination A consists of a primer set I and a primer set II; the primer combination B consists of a primer set III and a primer set IV;

the primer set I and the primer set II are used to perform the first cycle of PCR amplification on the template respectively, the amplified product by the primer set I is used as a template for the second cycle of amplification by the primer set III, the amplified product by the primer set II is used as a template for the second cycle of amplification by the primer set IV, and then the amplified products are mixed in equal volumes.

9. The method according to claim 7, wherein the analysis process of the sequencing result is: backtrack the sequencing data with the same random tag sequence to a molecular cluster; if the number of molecules in the cluster is greater than 5 and the consistency rate of molecular mutations in the cluster is greater than 80% and the number of clusters is greater than or equal to 5, the mutation is a true mutation from the original DNA sample.

10. A method for detecting multiple target mutations in a DNA sample, including the following steps:
   (1) construct a library according to the method of claim 1;
   (2) perform an enrichment of a target region on the library of step (1) and sequence and analyze the occurrence of target mutations in the DNA sample according to the sequencing results.

11. The method according to claim 10, wherein the analysis process of the sequencing result is: backtrack the sequencing data of the starting single-stranded DNA with the same length of the DNA insert, the same breakpoints at both ends of the DNA insert, and the same anchor sequence at both ends to a molecular cluster; a starting double-stranded DNA molecular cluster, which has the same length of the DNA insert, the same sequence except for the mutation point, the same anchor sequence at both ends of the molecular cluster except for the opposite position, is labeled as a pair of duplex molecular clusters; for a certain mutation, if there is at least one pair of duplex molecular cluster supported, it may be judged as true; if there is no duplex molecular cluster supported, it may be judged as true if there are at least 4 molecular clusters supported.

* * * * *

SEQUENCE LISTING

```
<160> NUMBER OF SEQ ID NOS: 347

<210> SEQ ID NO 1
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 1
gacacgacgc tcttccgatc tnnnnnnnnc cactagtagc ct                    42

<210> SEQ ID NO 2
<211> LENGTH: 41
<212> TYPE: DNA
<213> ORGANISM: Artificial Sequence
<220> FEATURE:
<223> OTHER INFORMATION: Synthesized

<400> SEQUENCE: 2
ggctactagt ggctgtctct tatacacatc tccgagccca c                     41

<210> SEQ ID NO 3
<211> LENGTH: 42
<212> TYPE: DNA
<213> ORGANISM: Artificial Sequence
<220> FEATURE:
<221> NAME/KEY: misc_feature
<222> LOCATION: (22)..(29)
```

```
<223> OTHER INFORMATION: n is a, c, g, or t
<220> FEATURE:
<223> OTHER INFORMATION: Synthesized

<400> SEQUENCE: 3
gacacgacgc tcttccgatc tnnnnnnnng gactgtgtcg gt        42

<210> SEQ ID NO 4
<211> LENGTH: 41
<212> TYPE: DNA
<213> ORGANISM: Artificial Sequence
<220> FEATURE:
<223> OTHER INFORMATION: Synthesized

<400> SEQUENCE: 4
ccgacacagt ccctgtctct tatacacatc tccgagccca c         41

<210> SEQ ID NO 5
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 5
gacacgacgc tcttccgatc tnnnnnnnng gtactgacag gt        42

<210> SEQ ID NO 6
<211> LENGTH: 41
<212> TYPE: DNA
<213> ORGANISM: Artificial Sequence
<220> FEATURE:
<223> OTHER INFORMATION: Synthesized

<400> SEQUENCE: 6
cctgtcagta ccctgtctct tatacacatc tccgagccca c         41

<210> SEQ ID NO 7
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 7
gacacgacgc tcttccgatc tnnnnnnnnc ctagtacagc ct        42

<210> SEQ ID NO 8
<211> LENGTH: 41
<212> TYPE: DNA
<213> ORGANISM: Artificial Sequence
<220> FEATURE:
<223> OTHER INFORMATION: Synthesized

<400> SEQUENCE: 8
ggctgtacta ggctgtctct tatacacatc tccgagccca c         41

<210> SEQ ID NO 9
<211> LENGTH: 42
```

```
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 9
gacacgacgc tcttccgatc tnnnnnnnng gtagtcagag gt                          42

<210> SEQ ID NO 10
<211> LENGTH: 41
<212> TYPE: DNA
<213> ORGANISM: Artificial Sequence
<220> FEATURE:
<223> OTHER INFORMATION: Synthesized

<400> SEQUENCE: 10
cctctgacta ccctgtctct tatacacatc tccgagccca c                          41

<210> SEQ ID NO 11
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 11
gacacgacgc tcttccgatc tnnnnnnnnt tctcacgtgt tt                          42

<210> SEQ ID NO 12
<211> LENGTH: 41
<212> TYPE: DNA
<213> ORGANISM: Artificial Sequence
<220> FEATURE:
<223> OTHER INFORMATION: Synthesized

<400> SEQUENCE: 12
aacacgtgag aactgtctct tatacacatc tccgagccca c                          41

<210> SEQ ID NO 13
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 13
gacacgacgc tcttccgatc tnnnnnnnna actccacgta at                          42

<210> SEQ ID NO 14
<211> LENGTH: 41
<212> TYPE: DNA
<213> ORGANISM: Artificial Sequence
<220> FEATURE:
<223> OTHER INFORMATION: Synthesized
```

-continued

<400> SEQUENCE: 14
ttacgtggag ttctgtctct tatacacatc tccgagccca c          41

<210> SEQ ID NO 15
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 15
gacacgacgc tcttccgatc tnnnnnnnnt tctcgagaat tt          42

<210> SEQ ID NO 16
<211> LENGTH: 41
<212> TYPE: DNA
<213> ORGANISM: Artificial Sequence
<220> FEATURE:
<223> OTHER INFORMATION: Synthesized

<400> SEQUENCE: 16
aattctcgag aactgtctct tatacacatc tccgagccca c          41

<210> SEQ ID NO 17
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 17
gacacgacgc tcttccgatc tnnnnnnnna aactcttcca at          42

<210> SEQ ID NO 18
<211> LENGTH: 41
<212> TYPE: DNA
<213> ORGANISM: Artificial Sequence
<220> FEATURE:
<223> OTHER INFORMATION: Synthesized

<400> SEQUENCE: 18
ttggaagagt ttctgtctct tatacacatc tccgagccca c          41

<210> SEQ ID NO 19
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 19
gacacgacgc tcttccgatc tnnnnnnnnt tggaacgtct tt          42

<210> SEQ ID NO 20

```
<211> LENGTH: 41
<212> TYPE: DNA
<213> ORGANISM: Artificial Sequence
<220> FEATURE:
<223> OTHER INFORMATION: Synthesized

<400> SEQUENCE: 20
aagacgttcc aactgtctct tatacacatc tccgagccca c                        41

<210> SEQ ID NO 21
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 21
gacacgacgc tcttccgatc tnnnnnnnnc cggactcctc ct                       42

<210> SEQ ID NO 22
<211> LENGTH: 41
<212> TYPE: DNA
<213> ORGANISM: Artificial Sequence
<220> FEATURE:
<223> OTHER INFORMATION: Synthesized

<400> SEQUENCE: 22
ggaggagtcc ggctgtctct tatacacatc tccgagccca c                        41

<210> SEQ ID NO 23
<211> LENGTH: 42
<212> TYPE: DNA
<213> ORGANISM: Artificial Sequence
<220> FEATURE:
<221> NAME/KEY: misc_feature
<222> LOCATION: (22)..(29)
<223> OTHER INFORMATION: n is a, c, g, or t
<220> FEATURE:
<223> OTHER INFORMATION: Synthesized

<400> SEQUENCE: 23
gacacgacgc tcttccgatc tnnnnnnnna aggaggagta at                       42

<210> SEQ ID NO 24
<211> LENGTH: 41
<212> TYPE: DNA
<213> ORGANISM: Artificial Sequence
<220> FEATURE:
<223> OTHER INFORMATION: Synthesized

<400> SEQUENCE: 24
ttactcctcc ttctgtctct tatacacatc tccgagccca c                        41

<210> SEQ ID NO 25
<211> LENGTH: 19
<212> TYPE: DNA
<213> ORGANISM: Artificial Sequence
<220> FEATURE:
<223> OTHER INFORMATION: Synthesized

<400> SEQUENCE: 25
gacacgacgc tcttccgat                                                 19
```

```
<210> SEQ ID NO 26
<211> LENGTH: 22
<212> TYPE: DNA
<213> ORGANISM: Artificial Sequence
<220> FEATURE:
<223> OTHER INFORMATION: Synthesized

<400> SEQUENCE: 26
gtgggctcgg agatgtgtat aa                                              22

<210> SEQ ID NO 27
<211> LENGTH: 27
<212> TYPE: DNA
<213> ORGANISM: Artificial Sequence
<220> FEATURE:
<223> OTHER INFORMATION: Synthesized

<400> SEQUENCE: 27
tctttcccta cacgacgctc ttccgat                                         27

<210> SEQ ID NO 28
<211> LENGTH: 20
<212> TYPE: DNA
<213> ORGANISM: Artificial Sequence
<220> FEATURE:
<223> OTHER INFORMATION: Synthesized

<400> SEQUENCE: 28
tgtattaggg tgcagcgctc                                                 20

<210> SEQ ID NO 29
<211> LENGTH: 18
<212> TYPE: DNA
<213> ORGANISM: Artificial Sequence
<220> FEATURE:
<223> OTHER INFORMATION: Synthesized

<400> SEQUENCE: 29
cgctcggatc tggacctg                                                   18

<210> SEQ ID NO 30
<211> LENGTH: 19
<212> TYPE: DNA
<213> ORGANISM: Artificial Sequence
<220> FEATURE:
<223> OTHER INFORMATION: Synthesized

<400> SEQUENCE: 30
tggagccctg tgactcgaa                                                  19

<210> SEQ ID NO 31
<211> LENGTH: 21
<212> TYPE: DNA
<213> ORGANISM: Artificial Sequence
<220> FEATURE:
<223> OTHER INFORMATION: Synthesized

<400> SEQUENCE: 31
gtgaccagga catggatgag g                                               21

<210> SEQ ID NO 32
<211> LENGTH: 21
<212> TYPE: DNA
<213> ORGANISM: Artificial Sequence
<220> FEATURE:
<223> OTHER INFORMATION: Synthesized
```

-continued

<400> SEQUENCE: 32
tcctccagta gacggtacag c                                      21

<210> SEQ ID NO 33
<211> LENGTH: 18
<212> TYPE: DNA
<213> ORGANISM: Artificial Sequence
<220> FEATURE:
<223> OTHER INFORMATION: Synthesized

<400> SEQUENCE: 33
tgctgcttgt ccccacac                                          18

<210> SEQ ID NO 34
<211> LENGTH: 18
<212> TYPE: DNA
<213> ORGANISM: Artificial Sequence
<220> FEATURE:
<223> OTHER INFORMATION: Synthesized

<400> SEQUENCE: 34
ccgcttggca ccacttcc                                          18

<210> SEQ ID NO 35
<211> LENGTH: 18
<212> TYPE: DNA
<213> ORGANISM: Artificial Sequence
<220> FEATURE:
<223> OTHER INFORMATION: Synthesized

<400> SEQUENCE: 35
ggcacgggaa gcacgtac                                          18

<210> SEQ ID NO 36
<211> LENGTH: 18
<212> TYPE: DNA
<213> ORGANISM: Artificial Sequence
<220> FEATURE:
<223> OTHER INFORMATION: Synthesized

<400> SEQUENCE: 36
ccttgcagtg ggaaggtg                                          18

<210> SEQ ID NO 37
<211> LENGTH: 23
<212> TYPE: DNA
<213> ORGANISM: Artificial Sequence
<220> FEATURE:
<223> OTHER INFORMATION: Synthesized

<400> SEQUENCE: 37
gacagaaaag cggctgttag tca                                    23

<210> SEQ ID NO 38
<211> LENGTH: 19
<212> TYPE: DNA
<213> ORGANISM: Artificial Sequence
<220> FEATURE:
<223> OTHER INFORMATION: Synthesized

<400> SEQUENCE: 38
ccgacctcag ctacagcat                                         19

<210> SEQ ID NO 39
<211> LENGTH: 21

```
<212> TYPE: DNA
<213> ORGANISM: Artificial Sequence
<220> FEATURE:
<223> OTHER INFORMATION: Synthesized

<400> SEQUENCE: 39
acttgagcaa cccggagtct g                                              21

<210> SEQ ID NO 40
<211> LENGTH: 20
<212> TYPE: DNA
<213> ORGANISM: Artificial Sequence
<220> FEATURE:
<223> OTHER INFORMATION: Synthesized

<400> SEQUENCE: 40
ctcctagctc tgcagtccga                                                20

<210> SEQ ID NO 41
<211> LENGTH: 18
<212> TYPE: DNA
<213> ORGANISM: Artificial Sequence
<220> FEATURE:
<223> OTHER INFORMATION: Synthesized

<400> SEQUENCE: 41
gcgcctggct ccatttcc                                                  18

<210> SEQ ID NO 42
<211> LENGTH: 21
<212> TYPE: DNA
<213> ORGANISM: Artificial Sequence
<220> FEATURE:
<223> OTHER INFORMATION: Synthesized

<400> SEQUENCE: 42
cgcctgagaa cctgcaaaga g                                              21

<210> SEQ ID NO 43
<211> LENGTH: 18
<212> TYPE: DNA
<213> ORGANISM: Artificial Sequence
<220> FEATURE:
<223> OTHER INFORMATION: Synthesized

<400> SEQUENCE: 43
gtccagggag caatgcgt                                                  18

<210> SEQ ID NO 44
<211> LENGTH: 19
<212> TYPE: DNA
<213> ORGANISM: Artificial Sequence
<220> FEATURE:
<223> OTHER INFORMATION: Synthesized

<400> SEQUENCE: 44
cgggttaccc cacagccta                                                 19

<210> SEQ ID NO 45
<211> LENGTH: 18
<212> TYPE: DNA
<213> ORGANISM: Artificial Sequence
<220> FEATURE:
<223> OTHER INFORMATION: Synthesized
```

<400> SEQUENCE: 45
ggctcccagt ggattcgc                                             18

<210> SEQ ID NO 46
<211> LENGTH: 18
<212> TYPE: DNA
<213> ORGANISM: Artificial Sequence
<220> FEATURE:
<223> OTHER INFORMATION: Synthesized

<400> SEQUENCE: 46
gtcctgcccc ttcacctt                                             18

<210> SEQ ID NO 47
<211> LENGTH: 22
<212> TYPE: DNA
<213> ORGANISM: Artificial Sequence
<220> FEATURE:
<223> OTHER INFORMATION: Synthesized

<400> SEQUENCE: 47
ccgactactg cctcacccat at                                        22

<210> SEQ ID NO 48
<211> LENGTH: 26
<212> TYPE: DNA
<213> ORGANISM: Artificial Sequence
<220> FEATURE:
<223> OTHER INFORMATION: Synthesized

<400> SEQUENCE: 48
gggtttttct tgttgacaag aatcct                                    26

<210> SEQ ID NO 49
<211> LENGTH: 22
<212> TYPE: DNA
<213> ORGANISM: Artificial Sequence
<220> FEATURE:
<223> OTHER INFORMATION: Synthesized

<400> SEQUENCE: 49
ccaacctcca atcactcacc aa                                        22

<210> SEQ ID NO 50
<211> LENGTH: 28
<212> TYPE: DNA
<213> ORGANISM: Artificial Sequence
<220> FEATURE:
<223> OTHER INFORMATION: Synthesized

<400> SEQUENCE: 50
ggcgttttat catattcctc ttcatcct                                  28

<210> SEQ ID NO 51
<211> LENGTH: 26
<212> TYPE: DNA
<213> ORGANISM: Artificial Sequence
<220> FEATURE:
<223> OTHER INFORMATION: Synthesized

<400> SEQUENCE: 51
ctacttccag gaacatcaac taccag                                    26

<210> SEQ ID NO 52

<211> LENGTH: 23
<212> TYPE: DNA
<213> ORGANISM: Artificial Sequence
<220> FEATURE:
<223> OTHER INFORMATION: Synthesized

<400> SEQUENCE: 52
ctgcacttgt attcccatcc cat                                            23

<210> SEQ ID NO 53
<211> LENGTH: 27
<212> TYPE: DNA
<213> ORGANISM: Artificial Sequence
<220> FEATURE:
<223> OTHER INFORMATION: Synthesized

<400> SEQUENCE: 53
tcagtttact agtgccattt gttcagt                                        27

<210> SEQ ID NO 54
<211> LENGTH: 28
<212> TYPE: DNA
<213> ORGANISM: Artificial Sequence
<220> FEATURE:
<223> OTHER INFORMATION: Synthesized

<400> SEQUENCE: 54
tacaacatct tgagtccctt tttacctc                                       28

<210> SEQ ID NO 55
<211> LENGTH: 23
<212> TYPE: DNA
<213> ORGANISM: Artificial Sequence
<220> FEATURE:
<223> OTHER INFORMATION: Synthesized

<400> SEQUENCE: 55
agaattgtgg gtcttttggg ctt                                            23

<210> SEQ ID NO 56
<211> LENGTH: 30
<212> TYPE: DNA
<213> ORGANISM: Artificial Sequence
<220> FEATURE:
<223> OTHER INFORMATION: Synthesized

<400> SEQUENCE: 56
tgtaaacaat atctgaacct ttaccctgtt                                     30

<210> SEQ ID NO 57
<211> LENGTH: 20
<212> TYPE: DNA
<213> ORGANISM: Artificial Sequence
<220> FEATURE:
<223> OTHER INFORMATION: Synthesized

<400> SEQUENCE: 57
gcatgcgtgg aacctttgtg                                                20

<210> SEQ ID NO 58
<211> LENGTH: 23
<212> TYPE: DNA
<213> ORGANISM: Artificial Sequence
<220> FEATURE:
<223> OTHER INFORMATION: Synthesized

<400> SEQUENCE: 58
aactctgttg tcctctctcg gaa                                           23

<210> SEQ ID NO 59
<211> LENGTH: 18
<212> TYPE: DNA
<213> ORGANISM: Artificial Sequence
<220> FEATURE:
<223> OTHER INFORMATION: Synthesized

<400> SEQUENCE: 59
ctgaatcccg cggacgac                                                 18

<210> SEQ ID NO 60
<211> LENGTH: 21
<212> TYPE: DNA
<213> ORGANISM: Artificial Sequence
<220> FEATURE:
<223> OTHER INFORMATION: Synthesized

<400> SEQUENCE: 60
ccgtctgtgc cttctcatct g                                             21

<210> SEQ ID NO 61
<211> LENGTH: 19
<212> TYPE: DNA
<213> ORGANISM: Artificial Sequence
<220> FEATURE:
<223> OTHER INFORMATION: Synthesized

<400> SEQUENCE: 61
gaacgcccac caggtcttg                                                19

<210> SEQ ID NO 62
<211> LENGTH: 24
<212> TYPE: DNA
<213> ORGANISM: Artificial Sequence
<220> FEATURE:
<223> OTHER INFORMATION: Synthesized

<400> SEQUENCE: 62
ccttgaggcg tacttcaaag actg                                          24

<210> SEQ ID NO 63
<211> LENGTH: 23
<212> TYPE: DNA
<213> ORGANISM: Artificial Sequence
<220> FEATURE:
<223> OTHER INFORMATION: Synthesized

<400> SEQUENCE: 63
ggaggctgta ggcataaatt ggt                                           23

<210> SEQ ID NO 64
<211> LENGTH: 22
<212> TYPE: DNA
<213> ORGANISM: Artificial Sequence
<220> FEATURE:
<223> OTHER INFORMATION: Synthesized

<400> SEQUENCE: 64
gtcctactgt tcaagcctcc aa                                            22

<210> SEQ ID NO 65

<211> LENGTH: 22
<212> TYPE: DNA
<213> ORGANISM: Artificial Sequence
<220> FEATURE:
<223> OTHER INFORMATION: Synthesized

<400> SEQUENCE: 65
gggcttctgt ggagttactc tc                                             22

<210> SEQ ID NO 66
<211> LENGTH: 22
<212> TYPE: DNA
<213> ORGANISM: Artificial Sequence
<220> FEATURE:
<223> OTHER INFORMATION: Synthesized

<400> SEQUENCE: 66
ttgtatcggg aggccttaga gt                                             22

<210> SEQ ID NO 67
<211> LENGTH: 21
<212> TYPE: DNA
<213> ORGANISM: Artificial Sequence
<220> FEATURE:
<223> OTHER INFORMATION: Synthesized

<400> SEQUENCE: 67
ttctgtgttg gggtgagttg a                                              21

<210> SEQ ID NO 68
<211> LENGTH: 25
<212> TYPE: DNA
<213> ORGANISM: Artificial Sequence
<220> FEATURE:
<223> OTHER INFORMATION: Synthesized

<400> SEQUENCE: 68
ccagcatcca gggaattagt agtca                                          25

<210> SEQ ID NO 69
<211> LENGTH: 27
<212> TYPE: DNA
<213> ORGANISM: Artificial Sequence
<220> FEATURE:
<223> OTHER INFORMATION: Synthesized

<400> SEQUENCE: 69
ttcctgtctt acctttggaa gagaaac                                        27

<210> SEQ ID NO 70
<211> LENGTH: 25
<212> TYPE: DNA
<213> ORGANISM: Artificial Sequence
<220> FEATURE:
<223> OTHER INFORMATION: Synthesized

<400> SEQUENCE: 70
ccggaaacta ctgttgttag acgta                                          25

<210> SEQ ID NO 71
<211> LENGTH: 23
<212> TYPE: DNA
<213> ORGANISM: Artificial Sequence
<220> FEATURE:
<223> OTHER INFORMATION: Synthesized

<400> SEQUENCE: 71
cgtcgcagaa gatctcaatc tcg                                    23

<210> SEQ ID NO 72
<211> LENGTH: 28
<212> TYPE: DNA
<213> ORGANISM: Artificial Sequence
<220> FEATURE:
<223> OTHER INFORMATION: Synthesized

<400> SEQUENCE: 72
aaactccctc ctttcctaac attcattt                               28

<210> SEQ ID NO 73
<211> LENGTH: 26
<212> TYPE: DNA
<213> ORGANISM: Artificial Sequence
<220> FEATURE:
<223> OTHER INFORMATION: Synthesized

<400> SEQUENCE: 73
tatgcctgct aggttctatc ctaacc                                 26

<210> SEQ ID NO 74
<211> LENGTH: 27
<212> TYPE: DNA
<213> ORGANISM: Artificial Sequence
<220> FEATURE:
<223> OTHER INFORMATION: Synthesized

<400> SEQUENCE: 74
ggcattattt acatactctg tggaagg                                27

<210> SEQ ID NO 75
<211> LENGTH: 22
<212> TYPE: DNA
<213> ORGANISM: Artificial Sequence
<220> FEATURE:
<223> OTHER INFORMATION: Synthesized

<400> SEQUENCE: 75
gttggtcttc caaacctcga ca                                     22

<210> SEQ ID NO 76
<211> LENGTH: 22
<212> TYPE: DNA
<213> ORGANISM: Artificial Sequence
<220> FEATURE:
<223> OTHER INFORMATION: Synthesized

<400> SEQUENCE: 76
ttcaacccca acaaggatca ct                                     22

<210> SEQ ID NO 77
<211> LENGTH: 20
<212> TYPE: DNA
<213> ORGANISM: Artificial Sequence
<220> FEATURE:
<223> OTHER INFORMATION: Synthesized

<400> SEQUENCE: 77
ttccaccaat cggcagtcag                                        20

<210> SEQ ID NO 78

```
<211> LENGTH: 21
<212> TYPE: DNA
<213> ORGANISM: Artificial Sequence
<220> FEATURE:
<223> OTHER INFORMATION: Synthesized

<400> SEQUENCE: 78
gccctgctca gaatactgtc t                                                 21

<210> SEQ ID NO 79
<211> LENGTH: 20
<212> TYPE: DNA
<213> ORGANISM: Artificial Sequence
<220> FEATURE:
<223> OTHER INFORMATION: Synthesized

<400> SEQUENCE: 79
attcgcagtc ccaaatctcc                                                   20

<210> SEQ ID NO 80
<211> LENGTH: 21
<212> TYPE: DNA
<213> ORGANISM: Artificial Sequence
<220> FEATURE:
<223> OTHER INFORMATION: Synthesized

<400> SEQUENCE: 80
catcttcctc tgcatcctgc t                                                 21

<210> SEQ ID NO 81
<211> LENGTH: 22
<212> TYPE: DNA
<213> ORGANISM: Artificial Sequence
<220> FEATURE:
<223> OTHER INFORMATION: Synthesized

<400> SEQUENCE: 81
ttccaggatc atcaaccacc ag                                                22

<210> SEQ ID NO 82
<211> LENGTH: 18
<212> TYPE: DNA
<213> ORGANISM: Artificial Sequence
<220> FEATURE:
<223> OTHER INFORMATION: Synthesized

<400> SEQUENCE: 82
gtccctttat gccgctgt                                                     18

<210> SEQ ID NO 83
<211> LENGTH: 29
<212> TYPE: DNA
<213> ORGANISM: Artificial Sequence
<220> FEATURE:
<223> OTHER INFORMATION: Synthesized

<400> SEQUENCE: 83
acccttataa agaatttgga gctactgtg                                         29

<210> SEQ ID NO 84
<211> LENGTH: 22
<212> TYPE: DNA
<213> ORGANISM: Artificial Sequence
<220> FEATURE:
<223> OTHER INFORMATION: Synthesized
```

<400> SEQUENCE: 84
ctcctgaaca ttgctcacct ca                                          22

<210> SEQ ID NO 85
<211> LENGTH: 18
<212> TYPE: DNA
<213> ORGANISM: Artificial Sequence
<220> FEATURE:
<223> OTHER INFORMATION: Synthesized

<400> SEQUENCE: 85
agactgcctt ccgggtca                                               18

<210> SEQ ID NO 86
<211> LENGTH: 22
<212> TYPE: DNA
<213> ORGANISM: Artificial Sequence
<220> FEATURE:
<223> OTHER INFORMATION: Synthesized

<400> SEQUENCE: 86
cctgtgggaa gcgaaaattc ca                                          22

<210> SEQ ID NO 87
<211> LENGTH: 19
<212> TYPE: DNA
<213> ORGANISM: Artificial Sequence
<220> FEATURE:
<223> OTHER INFORMATION: Synthesized

<400> SEQUENCE: 87
acctggtcct ctgactgct                                              19

<210> SEQ ID NO 88
<211> LENGTH: 24
<212> TYPE: DNA
<213> ORGANISM: Artificial Sequence
<220> FEATURE:
<223> OTHER INFORMATION: Synthesized

<400> SEQUENCE: 88
aagcaatgga tgatttgatg ctgt                                        24

<210> SEQ ID NO 89
<211> LENGTH: 20
<212> TYPE: DNA
<213> ORGANISM: Artificial Sequence
<220> FEATURE:
<223> OTHER INFORMATION: Synthesized

<400> SEQUENCE: 89
gacccaggtc cagatgaagc                                             20

<210> SEQ ID NO 90
<211> LENGTH: 18
<212> TYPE: DNA
<213> ORGANISM: Artificial Sequence
<220> FEATURE:
<223> OTHER INFORMATION: Synthesized

<400> SEQUENCE: 90
tcctggcccc tgtcatct                                               18

<210> SEQ ID NO 91

```
<211> LENGTH: 22
<212> TYPE: DNA
<213> ORGANISM: Artificial Sequence
<220> FEATURE:
<223> OTHER INFORMATION: Synthesized

<400> SEQUENCE: 91
gtgccctgac tttcaactct gt                                    22

<210> SEQ ID NO 92
<211> LENGTH: 18
<212> TYPE: DNA
<213> ORGANISM: Artificial Sequence
<220> FEATURE:
<223> OTHER INFORMATION: Synthesized

<400> SEQUENCE: 92
caactggcca agacctgc                                         18

<210> SEQ ID NO 93
<211> LENGTH: 20
<212> TYPE: DNA
<213> ORGANISM: Artificial Sequence
<220> FEATURE:
<223> OTHER INFORMATION: Synthesized

<400> SEQUENCE: 93
cgccatggcc atctacaagc                                       20

<210> SEQ ID NO 94
<211> LENGTH: 18
<212> TYPE: DNA
<213> ORGANISM: Artificial Sequence
<220> FEATURE:
<223> OTHER INFORMATION: Synthesized

<400> SEQUENCE: 94
ggtccccagg cctctgat                                         18

<210> SEQ ID NO 95
<211> LENGTH: 22
<212> TYPE: DNA
<213> ORGANISM: Artificial Sequence
<220> FEATURE:
<223> OTHER INFORMATION: Synthesized

<400> SEQUENCE: 95
gagtggaagg aaatttgcgt gt                                    22

<210> SEQ ID NO 96
<211> LENGTH: 19
<212> TYPE: DNA
<213> ORGANISM: Artificial Sequence
<220> FEATURE:
<223> OTHER INFORMATION: Synthesized

<400> SEQUENCE: 96
gcactggcct catcttggg                                        19

<210> SEQ ID NO 97
<211> LENGTH: 26
<212> TYPE: DNA
<213> ORGANISM: Artificial Sequence
<220> FEATURE:
<223> OTHER INFORMATION: Synthesized
```

-continued

<400> SEQUENCE: 97
ccatccacta caactacatg tgtaac                                          26

<210> SEQ ID NO 98
<211> LENGTH: 24
<212> TYPE: DNA
<213> ORGANISM: Artificial Sequence
<220> FEATURE:
<223> OTHER INFORMATION: Synthesized

<400> SEQUENCE: 98
tttccttact gcctcttgct tctc                                            24

<210> SEQ ID NO 99
<211> LENGTH: 20
<212> TYPE: DNA
<213> ORGANISM: Artificial Sequence
<220> FEATURE:
<223> OTHER INFORMATION: Synthesized

<400> SEQUENCE: 99
gggacggaac agctttgagg                                                 20

<210> SEQ ID NO 100
<211> LENGTH: 23
<212> TYPE: DNA
<213> ORGANISM: Artificial Sequence
<220> FEATURE:
<223> OTHER INFORMATION: Synthesized

<400> SEQUENCE: 100
cacagaggaa gagaatctcc gca                                             23

<210> SEQ ID NO 101
<211> LENGTH: 26
<212> TYPE: DNA
<213> ORGANISM: Artificial Sequence
<220> FEATURE:
<223> OTHER INFORMATION: Synthesized

<400> SEQUENCE: 101
tgcctcagat tcacttttat cacctt                                          26

<210> SEQ ID NO 102
<211> LENGTH: 30
<212> TYPE: DNA
<213> ORGANISM: Artificial Sequence
<220> FEATURE:
<223> OTHER INFORMATION: Synthesized

<400> SEQUENCE: 102
ctcaggtact gtgtatatac ttacttctcc                                      30

<210> SEQ ID NO 103
<211> LENGTH: 19
<212> TYPE: DNA
<213> ORGANISM: Artificial Sequence
<220> FEATURE:
<223> OTHER INFORMATION: Synthesized

<400> SEQUENCE: 103
cgtgagcgct tcgagatgt                                                  19

<210> SEQ ID NO 104

```
<211> LENGTH: 22
<212> TYPE: DNA
<213> ORGANISM: Artificial Sequence
<220> FEATURE:
<223> OTHER INFORMATION: Synthesized

<400> SEQUENCE: 104
gtgatgtcat ctctcctccc tg                                              22

<210> SEQ ID NO 105
<211> LENGTH: 25
<212> TYPE: DNA
<213> ORGANISM: Artificial Sequence
<220> FEATURE:
<223> OTHER INFORMATION: Synthesized

<400> SEQUENCE: 105
tgaagtccaa aaagggtcag tctac                                           25

<210> SEQ ID NO 106
<211> LENGTH: 20
<212> TYPE: DNA
<213> ORGANISM: Artificial Sequence
<220> FEATURE:
<223> OTHER INFORMATION: Synthesized

<400> SEQUENCE: 106
gggagcatct tcggtgaaac                                                 20

<210> SEQ ID NO 107
<211> LENGTH: 22
<212> TYPE: DNA
<213> ORGANISM: Artificial Sequence
<220> FEATURE:
<223> OTHER INFORMATION: Synthesized

<400> SEQUENCE: 107
caggcttatc ccatcttggt ca                                              22

<210> SEQ ID NO 108
<211> LENGTH: 18
<212> TYPE: DNA
<213> ORGANISM: Artificial Sequence
<220> FEATURE:
<223> OTHER INFORMATION: Synthesized

<400> SEQUENCE: 108
ttggtggctg gcttggtc                                                   18

<210> SEQ ID NO 109
<211> LENGTH: 21
<212> TYPE: DNA
<213> ORGANISM: Artificial Sequence
<220> FEATURE:
<223> OTHER INFORMATION: Synthesized

<400> SEQUENCE: 109
gctgtaccgt ctactggagg a                                               21

<210> SEQ ID NO 110
<211> LENGTH: 21
<212> TYPE: DNA
<213> ORGANISM: Artificial Sequence
<220> FEATURE:
<223> OTHER INFORMATION: Synthesized
```

<400> SEQUENCE: 110
gcttgttctc cagctctcgg a                                        21

<210> SEQ ID NO 111
<211> LENGTH: 18
<212> TYPE: DNA
<213> ORGANISM: Artificial Sequence
<220> FEATURE:
<223> OTHER INFORMATION: Synthesized

<400> SEQUENCE: 111
gggaagtggt gccaagcg                                            18

<210> SEQ ID NO 112
<211> LENGTH: 18
<212> TYPE: DNA
<213> ORGANISM: Artificial Sequence
<220> FEATURE:
<223> OTHER INFORMATION: Synthesized

<400> SEQUENCE: 112
gcacacgctg tacgtgct                                            18

<210> SEQ ID NO 113
<211> LENGTH: 18
<212> TYPE: DNA
<213> ORGANISM: Artificial Sequence
<220> FEATURE:
<223> OTHER INFORMATION: Synthesized

<400> SEQUENCE: 113
gcctccacct gctccttg                                            18

<210> SEQ ID NO 114
<211> LENGTH: 22
<212> TYPE: DNA
<213> ORGANISM: Artificial Sequence
<220> FEATURE:
<223> OTHER INFORMATION: Synthesized

<400> SEQUENCE: 114
ccctcaatga tccactgcat ga                                       22

<210> SEQ ID NO 115
<211> LENGTH: 24
<212> TYPE: DNA
<213> ORGANISM: Artificial Sequence
<220> FEATURE:
<223> OTHER INFORMATION: Synthesized

<400> SEQUENCE: 115
ctcatacagg acttgggagg tatc                                     24

<210> SEQ ID NO 116
<211> LENGTH: 18
<212> TYPE: DNA
<213> ORGANISM: Artificial Sequence
<220> FEATURE:
<223> OTHER INFORMATION: Synthesized

<400> SEQUENCE: 116
cacaaccgca ggacagct                                            18

<210> SEQ ID NO 117

```
<211> LENGTH: 18
<212> TYPE: DNA
<213> ORGANISM: Artificial Sequence
<220> FEATURE:
<223> OTHER INFORMATION: Synthesized

<400> SEQUENCE: 117
ctccaagcct cggactgc                                                 18

<210> SEQ ID NO 118
<211> LENGTH: 19
<212> TYPE: DNA
<213> ORGANISM: Artificial Sequence
<220> FEATURE:
<223> OTHER INFORMATION: Synthesized

<400> SEQUENCE: 118
gcctcacacc agccacaac                                                19

<210> SEQ ID NO 119
<211> LENGTH: 20
<212> TYPE: DNA
<213> ORGANISM: Artificial Sequence
<220> FEATURE:
<223> OTHER INFORMATION: Synthesized

<400> SEQUENCE: 119
tccccaccat gagcaaacca                                               20

<210> SEQ ID NO 120
<211> LENGTH: 18
<212> TYPE: DNA
<213> ORGANISM: Artificial Sequence
<220> FEATURE:
<223> OTHER INFORMATION: Synthesized

<400> SEQUENCE: 120
gtgcctccct gcaacact                                                 18

<210> SEQ ID NO 121
<211> LENGTH: 18
<212> TYPE: DNA
<213> ORGANISM: Artificial Sequence
<220> FEATURE:
<223> OTHER INFORMATION: Synthesized

<400> SEQUENCE: 121
gcaccacgaa tgccggac                                                 18

<210> SEQ ID NO 122
<211> LENGTH: 18
<212> TYPE: DNA
<213> ORGANISM: Artificial Sequence
<220> FEATURE:
<223> OTHER INFORMATION: Synthesized

<400> SEQUENCE: 122
gtggggtaac ccgaggga                                                 18

<210> SEQ ID NO 123
<211> LENGTH: 18
<212> TYPE: DNA
<213> ORGANISM: Artificial Sequence
<220> FEATURE:
<223> OTHER INFORMATION: Synthesized
```

```
<400> SEQUENCE: 123
gaggaggcgg agctggaa                                          18

<210> SEQ ID NO 124
<211> LENGTH: 18
<212> TYPE: DNA
<213> ORGANISM: Artificial Sequence
<220> FEATURE:
<223> OTHER INFORMATION: Synthesized

<400> SEQUENCE: 124
agcgctgcct gaaactcg                                          18

<210> SEQ ID NO 125
<211> LENGTH: 17
<212> TYPE: DNA
<213> ORGANISM: Artificial Sequence
<220> FEATURE:
<223> OTHER INFORMATION: Synthesized

<400> SEQUENCE: 125
cgcacgaacg tggccag                                           17

<210> SEQ ID NO 126
<211> LENGTH: 19
<212> TYPE: DNA
<213> ORGANISM: Artificial Sequence
<220> FEATURE:
<223> OTHER INFORMATION: Synthesized

<400> SEQUENCE: 126
gagccaccag caggaaagt                                         19

<210> SEQ ID NO 127
<211> LENGTH: 24
<212> TYPE: DNA
<213> ORGANISM: Artificial Sequence
<220> FEATURE:
<223> OTHER INFORMATION: Synthesized

<400> SEQUENCE: 127
ctaggaatcc tgatgttgtg ctct                                   24

<210> SEQ ID NO 128
<211> LENGTH: 22
<212> TYPE: DNA
<213> ORGANISM: Artificial Sequence
<220> FEATURE:
<223> OTHER INFORMATION: Synthesized

<400> SEQUENCE: 128
cgcgagtcta gactctgtgg ta                                     22

<210> SEQ ID NO 129
<211> LENGTH: 24
<212> TYPE: DNA
<213> ORGANISM: Artificial Sequence
<220> FEATURE:
<223> OTHER INFORMATION: Synthesized

<400> SEQUENCE: 129
atagccagga caaattggag gaca                                   24

<210> SEQ ID NO 130
```

<211> LENGTH: 21
<212> TYPE: DNA
<213> ORGANISM: Artificial Sequence
<220> FEATURE:
<223> OTHER INFORMATION: Synthesized

<400> SEQUENCE: 130
gacaaacggg caacatacct t                                              21

<210> SEQ ID NO 131
<211> LENGTH: 23
<212> TYPE: DNA
<213> ORGANISM: Artificial Sequence
<220> FEATURE:
<223> OTHER INFORMATION: Synthesized

<400> SEQUENCE: 131
ccgaaggttt tgtacagcaa caa                                            23

<210> SEQ ID NO 132
<211> LENGTH: 23
<212> TYPE: DNA
<213> ORGANISM: Artificial Sequence
<220> FEATURE:
<223> OTHER INFORMATION: Synthesized

<400> SEQUENCE: 132
ctgagccagg agaaacggac tga                                            23

<210> SEQ ID NO 133
<211> LENGTH: 26
<212> TYPE: DNA
<213> ORGANISM: Artificial Sequence
<220> FEATURE:
<223> OTHER INFORMATION: Synthesized

<400> SEQUENCE: 133
gggactcaag atgttgtaca gacttg                                         26

<210> SEQ ID NO 134
<211> LENGTH: 21
<212> TYPE: DNA
<213> ORGANISM: Artificial Sequence
<220> FEATURE:
<223> OTHER INFORMATION: Synthesized

<400> SEQUENCE: 134
gttaagggag tagccccaac g                                              21

<210> SEQ ID NO 135
<211> LENGTH: 25
<212> TYPE: DNA
<213> ORGANISM: Artificial Sequence
<220> FEATURE:
<223> OTHER INFORMATION: Synthesized

<400> SEQUENCE: 135
caggcagttt tcgaaaacat tgctt                                          25

<210> SEQ ID NO 136
<211> LENGTH: 27
<212> TYPE: DNA
<213> ORGANISM: Artificial Sequence
<220> FEATURE:
<223> OTHER INFORMATION: Synthesized

```
<400> SEQUENCE: 136
ttaaagcagg atagccacat tgtgtaa                                          27

<210> SEQ ID NO 137
<211> LENGTH: 25
<212> TYPE: DNA
<213> ORGANISM: Artificial Sequence
<220> FEATURE:
<223> OTHER INFORMATION: Synthesized

<400> SEQUENCE: 137
ggcaacaggg taaaggttca gatat                                            25

<210> SEQ ID NO 138
<211> LENGTH: 19
<212> TYPE: DNA
<213> ORGANISM: Artificial Sequence
<220> FEATURE:
<223> OTHER INFORMATION: Synthesized

<400> SEQUENCE: 138
ccacaaaggt tccacgcat                                                   19

<210> SEQ ID NO 139
<211> LENGTH: 24
<212> TYPE: DNA
<213> ORGANISM: Artificial Sequence
<220> FEATURE:
<223> OTHER INFORMATION: Synthesized

<400> SEQUENCE: 139
tggaaaggaa gtgtacttcc gaga                                             24

<210> SEQ ID NO 140
<211> LENGTH: 18
<212> TYPE: DNA
<213> ORGANISM: Artificial Sequence
<220> FEATURE:
<223> OTHER INFORMATION: Synthesized

<400> SEQUENCE: 140
gtcgtccgcg ggattcag                                                    18

<210> SEQ ID NO 141
<211> LENGTH: 18
<212> TYPE: DNA
<213> ORGANISM: Artificial Sequence
<220> FEATURE:
<223> OTHER INFORMATION: Synthesized

<400> SEQUENCE: 141
aaggcacaga cggggaga                                                    18

<210> SEQ ID NO 142
<211> LENGTH: 18
<212> TYPE: DNA
<213> ORGANISM: Artificial Sequence
<220> FEATURE:
<223> OTHER INFORMATION: Synthesized

<400> SEQUENCE: 142
tcacggtggt ctccatgc                                                    18

<210> SEQ ID NO 143
```

```
<211> LENGTH: 22
<212> TYPE: DNA
<213> ORGANISM: Artificial Sequence
<220> FEATURE:
<223> OTHER INFORMATION: Synthesized

<400> SEQUENCE: 143
ggtcgttgac attgctgaga gt                                            22

<210> SEQ ID NO 144
<211> LENGTH: 22
<212> TYPE: DNA
<213> ORGANISM: Artificial Sequence
<220> FEATURE:
<223> OTHER INFORMATION: Synthesized

<400> SEQUENCE: 144
aacctaatct cctcccccaa ct                                            22

<210> SEQ ID NO 145
<211> LENGTH: 23
<212> TYPE: DNA
<213> ORGANISM: Artificial Sequence
<220> FEATURE:
<223> OTHER INFORMATION: Synthesized

<400> SEQUENCE: 145
gcagaggtga aaagttgca tgg                                            23

<210> SEQ ID NO 146
<211> LENGTH: 18
<212> TYPE: DNA
<213> ORGANISM: Artificial Sequence
<220> FEATURE:
<223> OTHER INFORMATION: Synthesized

<400> SEQUENCE: 146
ccacccaagg cacagctt                                                 18

<210> SEQ ID NO 147
<211> LENGTH: 18
<212> TYPE: DNA
<213> ORGANISM: Artificial Sequence
<220> FEATURE:
<223> OTHER INFORMATION: Synthesized

<400> SEQUENCE: 147
actccacaga agccccaa                                                 18

<210> SEQ ID NO 148
<211> LENGTH: 20
<212> TYPE: DNA
<213> ORGANISM: Artificial Sequence
<220> FEATURE:
<223> OTHER INFORMATION: Synthesized

<400> SEQUENCE: 148
gcctcccgat acaaagcaga                                               20

<210> SEQ ID NO 149
<211> LENGTH: 24
<212> TYPE: DNA
<213> ORGANISM: Artificial Sequence
<220> FEATURE:
<223> OTHER INFORMATION: Synthesized
```

<400> SEQUENCE: 149
gattcatcaa ctcaccccaa caca                                              24

<210> SEQ ID NO 150
<211> LENGTH: 27
<212> TYPE: DNA
<213> ORGANISM: Artificial Sequence
<220> FEATURE:
<223> OTHER INFORMATION: Synthesized

<400> SEQUENCE: 150
acatagctga ctactaattc cctggat                                           27

<210> SEQ ID NO 151
<211> LENGTH: 25
<212> TYPE: DNA
<213> ORGANISM: Artificial Sequence
<220> FEATURE:
<223> OTHER INFORMATION: Synthesized

<400> SEQUENCE: 151
atccacactc caaaagacac caaat                                             25

<210> SEQ ID NO 152
<211> LENGTH: 22
<212> TYPE: DNA
<213> ORGANISM: Artificial Sequence
<220> FEATURE:
<223> OTHER INFORMATION: Synthesized

<400> SEQUENCE: 152
gcgagggagt tcttcttcta gg                                                22

<210> SEQ ID NO 153
<211> LENGTH: 25
<212> TYPE: DNA
<213> ORGANISM: Artificial Sequence
<220> FEATURE:
<223> OTHER INFORMATION: Synthesized

<400> SEQUENCE: 153
cagtaaagtt tcccaccttg tgagt                                             25

<210> SEQ ID NO 154
<211> LENGTH: 27
<212> TYPE: DNA
<213> ORGANISM: Artificial Sequence
<220> FEATURE:
<223> OTHER INFORMATION: Synthesized

<400> SEQUENCE: 154
cctcctgtaa atgaatgtta ggaaagg                                           27

<210> SEQ ID NO 155
<211> LENGTH: 26
<212> TYPE: DNA
<213> ORGANISM: Artificial Sequence
<220> FEATURE:
<223> OTHER INFORMATION: Synthesized

<400> SEQUENCE: 155
gtttaatgcc tttatccaag ggcaaa                                            26

<210> SEQ ID NO 156

<211> LENGTH: 27
<212> TYPE: DNA
<213> ORGANISM: Artificial Sequence
<220> FEATURE:
<223> OTHER INFORMATION: Synthesized

<400> SEQUENCE: 156
ctcttatata gaatcccagc cttccac                                         27

<210> SEQ ID NO 157
<211> LENGTH: 22
<212> TYPE: DNA
<213> ORGANISM: Artificial Sequence
<220> FEATURE:
<223> OTHER INFORMATION: Synthesized

<400> SEQUENCE: 157
cttgtcgagg tttggaagac ca                                              22

<210> SEQ ID NO 158
<211> LENGTH: 20
<212> TYPE: DNA
<213> ORGANISM: Artificial Sequence
<220> FEATURE:
<223> OTHER INFORMATION: Synthesized

<400> SEQUENCE: 158
gtttgagttg gctccgaacg                                                 20

<210> SEQ ID NO 159
<211> LENGTH: 18
<212> TYPE: DNA
<213> ORGANISM: Artificial Sequence
<220> FEATURE:
<223> OTHER INFORMATION: Synthesized

<400> SEQUENCE: 159
ctgagggctc caccccaa                                                   18

<210> SEQ ID NO 160
<211> LENGTH: 23
<212> TYPE: DNA
<213> ORGANISM: Artificial Sequence
<220> FEATURE:
<223> OTHER INFORMATION: Synthesized

<400> SEQUENCE: 160
gtgaagagat gggagtaggc tgt                                             23

<210> SEQ ID NO 161
<211> LENGTH: 26
<212> TYPE: DNA
<213> ORGANISM: Artificial Sequence
<220> FEATURE:
<223> OTHER INFORMATION: Synthesized

<400> SEQUENCE: 161
cccatctttt tgttttgtga gggttt                                          26

<210> SEQ ID NO 162
<211> LENGTH: 26
<212> TYPE: DNA
<213> ORGANISM: Artificial Sequence
<220> FEATURE:
<223> OTHER INFORMATION: Synthesized

```
<400> SEQUENCE: 162
ttaaagcagg atatccacat tgcgta                                          26

<210> SEQ ID NO 163
<211> LENGTH: 22
<212> TYPE: DNA
<213> ORGANISM: Artificial Sequence
<220> FEATURE:
<223> OTHER INFORMATION: Synthesized

<400> SEQUENCE: 163
ttgctgaaag tccaagagtc ct                                              22

<210> SEQ ID NO 164
<211> LENGTH: 23
<212> TYPE: DNA
<213> ORGANISM: Artificial Sequence
<220> FEATURE:
<223> OTHER INFORMATION: Synthesized

<400> SEQUENCE: 164
ggtgagcaat gttcaggaga ttc                                             23

<210> SEQ ID NO 165
<211> LENGTH: 22
<212> TYPE: DNA
<213> ORGANISM: Artificial Sequence
<220> FEATURE:
<223> OTHER INFORMATION: Synthesized

<400> SEQUENCE: 165
actactagat ccctggacgc tg                                              22

<210> SEQ ID NO 166
<211> LENGTH: 23
<212> TYPE: DNA
<213> ORGANISM: Artificial Sequence
<220> FEATURE:
<223> OTHER INFORMATION: Synthesized

<400> SEQUENCE: 166
ggtggagata agggagtagg ctg                                             23

<210> SEQ ID NO 167
<211> LENGTH: 20
<212> TYPE: DNA
<213> ORGANISM: Artificial Sequence
<220> FEATURE:
<223> OTHER INFORMATION: Synthesized

<400> SEQUENCE: 167
tgcccttcca atggatccac                                                 20

<210> SEQ ID NO 168
<211> LENGTH: 18
<212> TYPE: DNA
<213> ORGANISM: Artificial Sequence
<220> FEATURE:
<223> OTHER INFORMATION: Synthesized

<400> SEQUENCE: 168
gtccccagcc caaccctt                                                   18

<210> SEQ ID NO 169
```

```
<211> LENGTH: 20
<212> TYPE: DNA
<213> ORGANISM: Artificial Sequence
<220> FEATURE:
<223> OTHER INFORMATION: Synthesized

<400> SEQUENCE: 169
ctctggcatt ctgggagctt                                              20

<210> SEQ ID NO 170
<211> LENGTH: 22
<212> TYPE: DNA
<213> ORGANISM: Artificial Sequence
<220> FEATURE:
<223> OTHER INFORMATION: Synthesized

<400> SEQUENCE: 170
tggtaggttt tctgggaagg ga                                           22

<210> SEQ ID NO 171
<211> LENGTH: 21
<212> TYPE: DNA
<213> ORGANISM: Artificial Sequence
<220> FEATURE:
<223> OTHER INFORMATION: Synthesized

<400> SEQUENCE: 171
tgtcccagaa tgcaagaagc c                                            21

<210> SEQ ID NO 172
<211> LENGTH: 24
<212> TYPE: DNA
<213> ORGANISM: Artificial Sequence
<220> FEATURE:
<223> OTHER INFORMATION: Synthesized

<400> SEQUENCE: 172
ggcattgaag tctcatggaa gcca                                         24

<210> SEQ ID NO 173
<211> LENGTH: 20
<212> TYPE: DNA
<213> ORGANISM: Artificial Sequence
<220> FEATURE:
<223> OTHER INFORMATION: Synthesized

<400> SEQUENCE: 173
acctccgtca tgtgctgtga                                              20

<210> SEQ ID NO 174
<211> LENGTH: 21
<212> TYPE: DNA
<213> ORGANISM: Artificial Sequence
<220> FEATURE:
<223> OTHER INFORMATION: Synthesized

<400> SEQUENCE: 174
ctcaccatcg ctatctgagc a                                            21

<210> SEQ ID NO 175
<211> LENGTH: 18
<212> TYPE: DNA
<213> ORGANISM: Artificial Sequence
<220> FEATURE:
<223> OTHER INFORMATION: Synthesized
```

<400> SEQUENCE: 175
gcaaccagcc ctgtcgtc                                                    18

<210> SEQ ID NO 176
<211> LENGTH: 21
<212> TYPE: DNA
<213> ORGANISM: Artificial Sequence
<220> FEATURE:
<223> OTHER INFORMATION: Synthesized

<400> SEQUENCE: 176
gcaccaccac actatgtcga a                                                21

<210> SEQ ID NO 177
<211> LENGTH: 21
<212> TYPE: DNA
<213> ORGANISM: Artificial Sequence
<220> FEATURE:
<223> OTHER INFORMATION: Synthesized

<400> SEQUENCE: 177
ttaacccctc ctcccagaga c                                                21

<210> SEQ ID NO 178
<211> LENGTH: 24
<212> TYPE: DNA
<213> ORGANISM: Artificial Sequence
<220> FEATURE:
<223> OTHER INFORMATION: Synthesized

<400> SEQUENCE: 178
ttccagtgtg atgatggtga ggat                                             24

<210> SEQ ID NO 179
<211> LENGTH: 18
<212> TYPE: DNA
<213> ORGANISM: Artificial Sequence
<220> FEATURE:
<223> OTHER INFORMATION: Synthesized

<400> SEQUENCE: 179
cagcaggcca gtgtgcag                                                    18

<210> SEQ ID NO 180
<211> LENGTH: 18
<212> TYPE: DNA
<213> ORGANISM: Artificial Sequence
<220> FEATURE:
<223> OTHER INFORMATION: Synthesized

<400> SEQUENCE: 180
ccggtctctc ccaggaca                                                    18

<210> SEQ ID NO 181
<211> LENGTH: 20
<212> TYPE: DNA
<213> ORGANISM: Artificial Sequence
<220> FEATURE:
<223> OTHER INFORMATION: Synthesized

<400> SEQUENCE: 181
gtgaggctcc cctttcttgc                                                  20

<210> SEQ ID NO 182

<211> LENGTH: 19
<212> TYPE: DNA
<213> ORGANISM: Artificial Sequence
<220> FEATURE:
<223> OTHER INFORMATION: Synthesized

<400> SEQUENCE: 182
tggtctcctc caccgcttc                                          19

<210> SEQ ID NO 183
<211> LENGTH: 26
<212> TYPE: DNA
<213> ORGANISM: Artificial Sequence
<220> FEATURE:
<223> OTHER INFORMATION: Synthesized

<400> SEQUENCE: 183
gaaactttcc acttgataag aggtcc                                  26

<210> SEQ ID NO 184
<211> LENGTH: 18
<212> TYPE: DNA
<213> ORGANISM: Artificial Sequence
<220> FEATURE:
<223> OTHER INFORMATION: Synthesized

<400> SEQUENCE: 184
ctcccccctg gctccttc                                           18

<210> SEQ ID NO 185
<211> LENGTH: 19
<212> TYPE: DNA
<213> ORGANISM: Artificial Sequence
<220> FEATURE:
<223> OTHER INFORMATION: Synthesized

<400> SEQUENCE: 185
ggggagtagg gccaggaag                                          19

<210> SEQ ID NO 186
<211> LENGTH: 23
<212> TYPE: DNA
<213> ORGANISM: Artificial Sequence
<220> FEATURE:
<223> OTHER INFORMATION: Synthesized

<400> SEQUENCE: 186
gcccttctgt cttgaacatg agt                                     23

<210> SEQ ID NO 187
<211> LENGTH: 18
<212> TYPE: DNA
<213> ORGANISM: Artificial Sequence
<220> FEATURE:
<223> OTHER INFORMATION: Synthesized

<400> SEQUENCE: 187
gtgggaggct gtcagtgg                                           18

<210> SEQ ID NO 188
<211> LENGTH: 50
<212> TYPE: DNA
<213> ORGANISM: Artificial Sequence
<220> FEATURE:
<223> OTHER INFORMATION: Synthesized

<400> SEQUENCE: 188
aatgatacgg cgaccaccga gatctacact ctttccctac acgacgctct            50

<210> SEQ ID NO 189
<211> LENGTH: 24
<212> TYPE: DNA
<213> ORGANISM: Artificial Sequence
<220> FEATURE:
<223> OTHER INFORMATION: Synthesized

<400> SEQUENCE: 189
caagcagaag acggcatacg agat                                        24

<210> SEQ ID NO 190
<211> LENGTH: 33
<212> TYPE: DNA
<213> ORGANISM: Artificial Sequence
<220> FEATURE:
<223> OTHER INFORMATION: Synthesized

<400> SEQUENCE: 190
gtgactggag ttccttggca cccgagaatt cca                              33

<210> SEQ ID NO 191
<211> LENGTH: 38
<212> TYPE: DNA
<213> ORGANISM: Artificial Sequence
<220> FEATURE:
<223> OTHER INFORMATION: Synthesized

<400> SEQUENCE: 191
cttggcaccc gagaattcca ttgttccttg acgcagag                         38

<210> SEQ ID NO 192
<211> LENGTH: 40
<212> TYPE: DNA
<213> ORGANISM: Artificial Sequence
<220> FEATURE:
<223> OTHER INFORMATION: Synthesized

<400> SEQUENCE: 192
cttggcaccc gagaattcca gacctggggt atgagcctga                       40

<210> SEQ ID NO 193
<211> LENGTH: 38
<212> TYPE: DNA
<213> ORGANISM: Artificial Sequence
<220> FEATURE:
<223> OTHER INFORMATION: Synthesized

<400> SEQUENCE: 193
cttggcaccc gagaattcca aggctgaagc tggcgaga                         38

<210> SEQ ID NO 194
<211> LENGTH: 40
<212> TYPE: DNA
<213> ORGANISM: Artificial Sequence
<220> FEATURE:
<223> OTHER INFORMATION: Synthesized

<400> SEQUENCE: 194
cttggcaccc gagaattcca tgaggacgat ggcagagacg                       40

<210> SEQ ID NO 195

```
<211> LENGTH: 40
<212> TYPE: DNA
<213> ORGANISM: Artificial Sequence
<220> FEATURE:
<223> OTHER INFORMATION: Synthesized

<400> SEQUENCE: 195
cttggcaccc gagaattcca gtacagcgaa ggcagagagt                    40

<210> SEQ ID NO 196
<211> LENGTH: 41
<212> TYPE: DNA
<213> ORGANISM: Artificial Sequence
<220> FEATURE:
<223> OTHER INFORMATION: Synthesized

<400> SEQUENCE: 196
cttggcaccc gagaattcca cacacaggag gaggaaggtg a                  41

<210> SEQ ID NO 197
<211> LENGTH: 39
<212> TYPE: DNA
<213> ORGANISM: Artificial Sequence
<220> FEATURE:
<223> OTHER INFORMATION: Synthesized

<400> SEQUENCE: 197
cttggcaccc gagaattcca tgtgtggaca tgggctgtg                     39

<210> SEQ ID NO 198
<211> LENGTH: 38
<212> TYPE: DNA
<213> ORGANISM: Artificial Sequence
<220> FEATURE:
<223> OTHER INFORMATION: Synthesized

<400> SEQUENCE: 198
cttggcaccc gagaattcca acccaagtca ggggcgaa                      38

<210> SEQ ID NO 199
<211> LENGTH: 44
<212> TYPE: DNA
<213> ORGANISM: Artificial Sequence
<220> FEATURE:
<223> OTHER INFORMATION: Synthesized

<400> SEQUENCE: 199
cttggcaccc gagaattcca gcgtgcaaaa gaaatgccaa gaag               44

<210> SEQ ID NO 200
<211> LENGTH: 41
<212> TYPE: DNA
<213> ORGANISM: Artificial Sequence
<220> FEATURE:
<223> OTHER INFORMATION: Synthesized

<400> SEQUENCE: 200
cttggcaccc gagaattcca tagtcactgg cagcaacagt c                  41

<210> SEQ ID NO 201
<211> LENGTH: 38
<212> TYPE: DNA
<213> ORGANISM: Artificial Sequence
<220> FEATURE:
<223> OTHER INFORMATION: Synthesized
```

```
<400> SEQUENCE: 201
cttggcaccc gagaattcca ctgcaaggcc tcgggaga                              38

<210> SEQ ID NO 202
<211> LENGTH: 41
<212> TYPE: DNA
<213> ORGANISM: Artificial Sequence
<220> FEATURE:
<223> OTHER INFORMATION: Synthesized

<400> SEQUENCE: 202
cttggcaccc gagaattcca attcctggga agtcctcagc t                         41

<210> SEQ ID NO 203
<211> LENGTH: 38
<212> TYPE: DNA
<213> ORGANISM: Artificial Sequence
<220> FEATURE:
<223> OTHER INFORMATION: Synthesized

<400> SEQUENCE: 203
cttggcaccc gagaattcca gcttggagcc aggtgcct                             38

<210> SEQ ID NO 204
<211> LENGTH: 43
<212> TYPE: DNA
<213> ORGANISM: Artificial Sequence
<220> FEATURE:
<223> OTHER INFORMATION: Synthesized

<400> SEQUENCE: 204
cttggcaccc gagaattcca catttcccac cctttctcga cgg                       43

<210> SEQ ID NO 205
<211> LENGTH: 38
<212> TYPE: DNA
<213> ORGANISM: Artificial Sequence
<220> FEATURE:
<223> OTHER INFORMATION: Synthesized

<400> SEQUENCE: 205
cttggcaccc gagaattcca acgggcctgt gtcaagga                             38

<210> SEQ ID NO 206
<211> LENGTH: 38
<212> TYPE: DNA
<213> ORGANISM: Artificial Sequence
<220> FEATURE:
<223> OTHER INFORMATION: Synthesized

<400> SEQUENCE: 206
cttggcaccc gagaattcca atgcgtcctc gggttcgt                             38

<210> SEQ ID NO 207
<211> LENGTH: 38
<212> TYPE: DNA
<213> ORGANISM: Artificial Sequence
<220> FEATURE:
<223> OTHER INFORMATION: Synthesized

<400> SEQUENCE: 207
cttggcaccc gagaattcca agcctaggcc gattcgac                             38

<210> SEQ ID NO 208
```

```
<211> LENGTH: 38
<212> TYPE: DNA
<213> ORGANISM: Artificial Sequence
<220> FEATURE:
<223> OTHER INFORMATION: Synthesized

<400> SEQUENCE: 208
cttggcaccc gagaattcca gattcgcggg cacagacg                             38

<210> SEQ ID NO 209
<211> LENGTH: 38
<212> TYPE: DNA
<213> ORGANISM: Artificial Sequence
<220> FEATURE:
<223> OTHER INFORMATION: Synthesized

<400> SEQUENCE: 209
cttggcaccc gagaattcca ttccagctcc gcctcctc                             38

<210> SEQ ID NO 210
<211> LENGTH: 44
<212> TYPE: DNA
<213> ORGANISM: Artificial Sequence
<220> FEATURE:
<223> OTHER INFORMATION: Synthesized

<400> SEQUENCE: 210
cttggcaccc gagaattcca cccatatcgt caatcttctc gagg                      44

<210> SEQ ID NO 211
<211> LENGTH: 45
<212> TYPE: DNA
<213> ORGANISM: Artificial Sequence
<220> FEATURE:
<223> OTHER INFORMATION: Synthesized

<400> SEQUENCE: 211
cttggcaccc gagaattcca tcacagtacc acagagtcta gactc                     45

<210> SEQ ID NO 212
<211> LENGTH: 44
<212> TYPE: DNA
<213> ORGANISM: Artificial Sequence
<220> FEATURE:
<223> OTHER INFORMATION: Synthesized

<400> SEQUENCE: 212
cttggcaccc gagaattcca aacctcttgt cctccaattt gtcc                      44

<210> SEQ ID NO 213
<211> LENGTH: 42
<212> TYPE: DNA
<213> ORGANISM: Artificial Sequence
<220> FEATURE:
<223> OTHER INFORMATION: Synthesized

<400> SEQUENCE: 213
cttggcaccc gagaattcca cctgctgcta tgcctcatct tc                        42

<210> SEQ ID NO 214
<211> LENGTH: 39
<212> TYPE: DNA
<213> ORGANISM: Artificial Sequence
<220> FEATURE:
<223> OTHER INFORMATION: Synthesized
```

-continued

<400> SEQUENCE: 214
cttggcaccc gagaattcca cacgggacca tgcaagacc                         39

<210> SEQ ID NO 215
<211> LENGTH: 42
<212> TYPE: DNA
<213> ORGANISM: Artificial Sequence
<220> FEATURE:
<223> OTHER INFORMATION: Synthesized

<400> SEQUENCE: 215
cttggcaccc gagaattcca tgggctttcg caagattcct at                     42

<210> SEQ ID NO 216
<211> LENGTH: 39
<212> TYPE: DNA
<213> ORGANISM: Artificial Sequence
<220> FEATURE:
<223> OTHER INFORMATION: Synthesized

<400> SEQUENCE: 216
cttggcaccc gagaattcca cgtagggctt tcccccact                         39

<210> SEQ ID NO 217
<211> LENGTH: 51
<212> TYPE: DNA
<213> ORGANISM: Artificial Sequence
<220> FEATURE:
<223> OTHER INFORMATION: Synthesized

<400> SEQUENCE: 217
cttggcaccc gagaattcca cctctattac caattttctt ttgtctttgg g           51

<210> SEQ ID NO 218
<211> LENGTH: 42
<212> TYPE: DNA
<213> ORGANISM: Artificial Sequence
<220> FEATURE:
<223> OTHER INFORMATION: Synthesized

<400> SEQUENCE: 218
cttggcaccc gagaattcca acacaatgtg gctatcctgc tt                     42

<210> SEQ ID NO 219
<211> LENGTH: 38
<212> TYPE: DNA
<213> ORGANISM: Artificial Sequence
<220> FEATURE:
<223> OTHER INFORMATION: Synthesized

<400> SEQUENCE: 219
cttggcaccc gagaattcca ggcaacggtc aggtctct                          38

<210> SEQ ID NO 220
<211> LENGTH: 43
<212> TYPE: DNA
<213> ORGANISM: Artificial Sequence
<220> FEATURE:
<223> OTHER INFORMATION: Synthesized

<400> SEQUENCE: 220
cttggcaccc gagaattcca ctctgccgat ccatactgcg gaa                    43

<210> SEQ ID NO 221

-continued

```
<211> LENGTH: 42
<212> TYPE: DNA
<213> ORGANISM: Artificial Sequence
<220> FEATURE:
<223> OTHER INFORMATION: Synthesized

<400> SEQUENCE: 221
cttggcaccc gagaattcca cacttccttt ccatggctgc ta                    42

<210> SEQ ID NO 222
<211> LENGTH: 39
<212> TYPE: DNA
<213> ORGANISM: Artificial Sequence
<220> FEATURE:
<223> OTHER INFORMATION: Synthesized

<400> SEQUENCE: 222
cttggcaccc gagaattcca ccgtttggga ctctaccgt                        39

<210> SEQ ID NO 223
<211> LENGTH: 38
<212> TYPE: DNA
<213> ORGANISM: Artificial Sequence
<220> FEATURE:
<223> OTHER INFORMATION: Synthesized

<400> SEQUENCE: 223
cttggcaccc gagaattcca cgtgtgcact tcgcttca                         38

<210> SEQ ID NO 224
<211> LENGTH: 44
<212> TYPE: DNA
<213> ORGANISM: Artificial Sequence
<220> FEATURE:
<223> OTHER INFORMATION: Synthesized

<400> SEQUENCE: 224
cttggcaccc gagaattcca ttgcccaagg tcttacataa gagg                  44

<210> SEQ ID NO 225
<211> LENGTH: 45
<212> TYPE: DNA
<213> ORGANISM: Artificial Sequence
<220> FEATURE:
<223> OTHER INFORMATION: Synthesized

<400> SEQUENCE: 225
cttggcaccc gagaattcca gtttgtttaa ggactgggag gagtt                 45

<210> SEQ ID NO 226
<211> LENGTH: 41
<212> TYPE: DNA
<213> ORGANISM: Artificial Sequence
<220> FEATURE:
<223> OTHER INFORMATION: Synthesized

<400> SEQUENCE: 226
cttggcaccc gagaattcca ggtctgttca ccagcaccat g                     41

<210> SEQ ID NO 227
<211> LENGTH: 38
<212> TYPE: DNA
<213> ORGANISM: Artificial Sequence
<220> FEATURE:
<223> OTHER INFORMATION: Synthesized
```

<400> SEQUENCE: 227
cttggcaccc gagaattcca ctgtgccttg ggtggctt                                    38

<210> SEQ ID NO 228
<211> LENGTH: 47
<212> TYPE: DNA
<213> ORGANISM: Artificial Sequence
<220> FEATURE:
<223> OTHER INFORMATION: Synthesized

<400> SEQUENCE: 228
cttggcaccc gagaattcca ttgccttctg atttctttcc ttctatt                         47

<210> SEQ ID NO 229
<211> LENGTH: 43
<212> TYPE: DNA
<213> ORGANISM: Artificial Sequence
<220> FEATURE:
<223> OTHER INFORMATION: Synthesized

<400> SEQUENCE: 229
cttggcaccc gagaattcca gagtctccgg aacattgttc acc                             43

<210> SEQ ID NO 230
<211> LENGTH: 41
<212> TYPE: DNA
<213> ORGANISM: Artificial Sequence
<220> FEATURE:
<223> OTHER INFORMATION: Synthesized

<400> SEQUENCE: 230
cttggcaccc gagaattcca agttgatgaa tctggccacc t                               41

<210> SEQ ID NO 231
<211> LENGTH: 48
<212> TYPE: DNA
<213> ORGANISM: Artificial Sequence
<220> FEATURE:
<223> OTHER INFORMATION: Synthesized

<400> SEQUENCE: 231
cttggcaccc gagaattcca cagctatgtt aatgttaata tgggccta                        48

<210> SEQ ID NO 232
<211> LENGTH: 46
<212> TYPE: DNA
<213> ORGANISM: Artificial Sequence
<220> FEATURE:
<223> OTHER INFORMATION: Synthesized

<400> SEQUENCE: 232
cttggcaccc gagaattcca tatttggtgt cttttggagt gtggat                          46

<210> SEQ ID NO 233
<211> LENGTH: 41
<212> TYPE: DNA
<213> ORGANISM: Artificial Sequence
<220> FEATURE:
<223> OTHER INFORMATION: Synthesized

<400> SEQUENCE: 233
cttggcaccc gagaattcca tagaggcagg tcccctagaa g                               41

<210> SEQ ID NO 234

```
<211> LENGTH: 46
<212> TYPE: DNA
<213> ORGANISM: Artificial Sequence
<220> FEATURE:
<223> OTHER INFORMATION: Synthesized

<400> SEQUENCE: 234
cttggcaccc gagaattcca caatgttagt atcccttgga ctcaca          46

<210> SEQ ID NO 235
<211> LENGTH: 47
<212> TYPE: DNA
<213> ORGANISM: Artificial Sequence
<220> FEATURE:
<223> OTHER INFORMATION: Synthesized

<400> SEQUENCE: 235
cttggcaccc gagaattcca acaggaggac attattgata gatgtca         47

<210> SEQ ID NO 236
<211> LENGTH: 43
<212> TYPE: DNA
<213> ORGANISM: Artificial Sequence
<220> FEATURE:
<223> OTHER INFORMATION: Synthesized

<400> SEQUENCE: 236
cttggcaccc gagaattcca aaccttacca agtatttgcc ctt             43

<210> SEQ ID NO 237
<211> LENGTH: 45
<212> TYPE: DNA
<213> ORGANISM: Artificial Sequence
<220> FEATURE:
<223> OTHER INFORMATION: Synthesized

<400> SEQUENCE: 237
cttggcaccc gagaattcca tctgtggaag gctgggattc tatat           45

<210> SEQ ID NO 238
<211> LENGTH: 42
<212> TYPE: DNA
<213> ORGANISM: Artificial Sequence
<220> FEATURE:
<223> OTHER INFORMATION: Synthesized

<400> SEQUENCE: 238
cttggcaccc gagaattcca gggacaaatc tttctgttcc ca              42

<210> SEQ ID NO 239
<211> LENGTH: 39
<212> TYPE: DNA
<213> ORGANISM: Artificial Sequence
<220> FEATURE:
<223> OTHER INFORMATION: Synthesized

<400> SEQUENCE: 239
cttggcaccc gagaattcca ggccagaggc aaatcaggt                  39

<210> SEQ ID NO 240
<211> LENGTH: 42
<212> TYPE: DNA
<213> ORGANISM: Artificial Sequence
<220> FEATURE:
<223> OTHER INFORMATION: Synthesized
```

```
<400> SEQUENCE: 240
cttggcaccc gagaattcca cagtcaggaa gacagcctac tc            42

<210> SEQ ID NO 241
<211> LENGTH: 44
<212> TYPE: DNA
<213> ORGANISM: Artificial Sequence
<220> FEATURE:
<223> OTHER INFORMATION: Synthesized

<400> SEQUENCE: 241
cttggcaccc gagaattcca aatactgtct ctgccatatc gtca          44

<210> SEQ ID NO 242
<211> LENGTH: 42
<212> TYPE: DNA
<213> ORGANISM: Artificial Sequence
<220> FEATURE:
<223> OTHER INFORMATION: Synthesized

<400> SEQUENCE: 242
cttggcaccc gagaattcca gtgtgtttca tgagtgggag ga            42

<210> SEQ ID NO 243
<211> LENGTH: 44
<212> TYPE: DNA
<213> ORGANISM: Artificial Sequence
<220> FEATURE:
<223> OTHER INFORMATION: Synthesized

<400> SEQUENCE: 243
cttggcaccc gagaattcca tttgccttct gacttctttc cgtc          44

<210> SEQ ID NO 244
<211> LENGTH: 40
<212> TYPE: DNA
<213> ORGANISM: Artificial Sequence
<220> FEATURE:
<223> OTHER INFORMATION: Synthesized

<400> SEQUENCE: 244
cttggcaccc gagaattcca cacagcactc aggcaagcta               40

<210> SEQ ID NO 245
<211> LENGTH: 39
<212> TYPE: DNA
<213> ORGANISM: Artificial Sequence
<220> FEATURE:
<223> OTHER INFORMATION: Synthesized

<400> SEQUENCE: 245
cttggcaccc gagaattcca gtcactgcca tggaggagc                39

<210> SEQ ID NO 246
<211> LENGTH: 40
<212> TYPE: DNA
<213> ORGANISM: Artificial Sequence
<220> FEATURE:
<223> OTHER INFORMATION: Synthesized

<400> SEQUENCE: 246
cttggcaccc gagaattcca ccatgggact gactttctgc               40

<210> SEQ ID NO 247
```

```
<211> LENGTH: 43
<212> TYPE: DNA
<213> ORGANISM: Artificial Sequence
<220> FEATURE:
<223> OTHER INFORMATION: Synthesized

<400> SEQUENCE: 247
cttggcaccc gagaattcca actgctcttt tcacccatct aca                    43

<210> SEQ ID NO 248
<211> LENGTH: 41
<212> TYPE: DNA
<213> ORGANISM: Artificial Sequence
<220> FEATURE:
<223> OTHER INFORMATION: Synthesized

<400> SEQUENCE: 248
cttggcaccc gagaattcca tgtccccgga cgatattgaa c                      41

<210> SEQ ID NO 249
<211> LENGTH: 42
<212> TYPE: DNA
<213> ORGANISM: Artificial Sequence
<220> FEATURE:
<223> OTHER INFORMATION: Synthesized

<400> SEQUENCE: 249
cttggcaccc gagaattcca cagatgaagc tcccagaatg cc                     42

<210> SEQ ID NO 250
<211> LENGTH: 42
<212> TYPE: DNA
<213> ORGANISM: Artificial Sequence
<220> FEATURE:
<223> OTHER INFORMATION: Synthesized

<400> SEQUENCE: 250
cttggcaccc gagaattcca tgtcatcttc tgtcccttcc ca                     42

<210> SEQ ID NO 251
<211> LENGTH: 44
<212> TYPE: DNA
<213> ORGANISM: Artificial Sequence
<220> FEATURE:
<223> OTHER INFORMATION: Synthesized

<400> SEQUENCE: 251
cttggcaccc gagaattcca caactctgtc tccttcctct tcct                   44

<210> SEQ ID NO 252
<211> LENGTH: 39
<212> TYPE: DNA
<213> ORGANISM: Artificial Sequence
<220> FEATURE:
<223> OTHER INFORMATION: Synthesized

<400> SEQUENCE: 252
cttggcaccc gagaattcca tgtgcagctg tgggttgat                         39

<210> SEQ ID NO 253
<211> LENGTH: 42
<212> TYPE: DNA
<213> ORGANISM: Artificial Sequence
<220> FEATURE:
<223> OTHER INFORMATION: Synthesized
```

<400> SEQUENCE: 253
cttggcaccc gagaattcca caagcagtca cagcacatga cg                              42

<210> SEQ ID NO 254
<211> LENGTH: 43
<212> TYPE: DNA
<213> ORGANISM: Artificial Sequence
<220> FEATURE:
<223> OTHER INFORMATION: Synthesized

<400> SEQUENCE: 254
cttggcaccc gagaattcca cctctgattc ctcactgatt gct                             43

<210> SEQ ID NO 255
<211> LENGTH: 42
<212> TYPE: DNA
<213> ORGANISM: Artificial Sequence
<220> FEATURE:
<223> OTHER INFORMATION: Synthesized

<400> SEQUENCE: 255
cttggcaccc gagaattcca ttgcgtgtgg agtatttgga tg                              42

<210> SEQ ID NO 256
<211> LENGTH: 42
<212> TYPE: DNA
<213> ORGANISM: Artificial Sequence
<220> FEATURE:
<223> OTHER INFORMATION: Synthesized

<400> SEQUENCE: 256
cttggcaccc gagaattcca tcttgggcct gtgttatctc ct                              42

<210> SEQ ID NO 257
<211> LENGTH: 44
<212> TYPE: DNA
<213> ORGANISM: Artificial Sequence
<220> FEATURE:
<223> OTHER INFORMATION: Synthesized

<400> SEQUENCE: 257
cttggcaccc gagaattcca acatgtgtaa cagttcctgc atgg                            44

<210> SEQ ID NO 258
<211> LENGTH: 46
<212> TYPE: DNA
<213> ORGANISM: Artificial Sequence
<220> FEATURE:
<223> OTHER INFORMATION: Synthesized

<400> SEQUENCE: 258
cttggcaccc gagaattcca cttgcttctc ttttcctatc ctgagt                          46

<210> SEQ ID NO 259
<211> LENGTH: 41
<212> TYPE: DNA
<213> ORGANISM: Artificial Sequence
<220> FEATURE:
<223> OTHER INFORMATION: Synthesized

<400> SEQUENCE: 259
cttggcaccc gagaattcca ctttgaggtg cgtgtttgtg c                               41

<210> SEQ ID NO 260

```
<211> LENGTH: 39
<212> TYPE: DNA
<213> ORGANISM: Artificial Sequence
<220> FEATURE:
<223> OTHER INFORMATION: Synthesized

<400> SEQUENCE: 260
cttggcaccc gagaattcca gcaagaaagg ggagcctca                        39

<210> SEQ ID NO 261
<211> LENGTH: 43
<212> TYPE: DNA
<213> ORGANISM: Artificial Sequence
<220> FEATURE:
<223> OTHER INFORMATION: Synthesized

<400> SEQUENCE: 261
cttggcaccc gagaattcca atcacctttc cttgcctctt tcc                   43

<210> SEQ ID NO 262
<211> LENGTH: 40
<212> TYPE: DNA
<213> ORGANISM: Artificial Sequence
<220> FEATURE:
<223> OTHER INFORMATION: Synthesized

<400> SEQUENCE: 262
cttggcaccc gagaattcca ttctccccct cctctgttgc                       40

<210> SEQ ID NO 263
<211> LENGTH: 41
<212> TYPE: DNA
<213> ORGANISM: Artificial Sequence
<220> FEATURE:
<223> OTHER INFORMATION: Synthesized

<400> SEQUENCE: 263
cttggcaccc gagaattcca cttcgagatg ttccgagagc t                     41

<210> SEQ ID NO 264
<211> LENGTH: 41
<212> TYPE: DNA
<213> ORGANISM: Artificial Sequence
<220> FEATURE:
<223> OTHER INFORMATION: Synthesized

<400> SEQUENCE: 264
cttggcaccc gagaattcca cctccctgct tctgtctcct a                     41

<210> SEQ ID NO 265
<211> LENGTH: 40
<212> TYPE: DNA
<213> ORGANISM: Artificial Sequence
<220> FEATURE:
<223> OTHER INFORMATION: Synthesized

<400> SEQUENCE: 265
cttggcaccc gagaattcca tcagtctacc tcccgccata                       40

<210> SEQ ID NO 266
<211> LENGTH: 40
<212> TYPE: DNA
<213> ORGANISM: Artificial Sequence
<220> FEATURE:
<223> OTHER INFORMATION: Synthesized
```

<400> SEQUENCE: 266
cttggcaccc gagaattcca gaaacttgct ccgaggtcca                            40

<210> SEQ ID NO 267
<211> LENGTH: 40
<212> TYPE: DNA
<213> ORGANISM: Artificial Sequence
<220> FEATURE:
<223> OTHER INFORMATION: Synthesized

<400> SEQUENCE: 267
cttggcaccc gagaattcca catccagcag ggaatgcagt                            40

<210> SEQ ID NO 268
<211> LENGTH: 44
<212> TYPE: DNA
<213> ORGANISM: Artificial Sequence
<220> FEATURE:
<223> OTHER INFORMATION: Synthesized

<400> SEQUENCE: 268
cttggcaccc gagaattcca gacacgatgc cattgttatc aaga                       44

<210> SEQ ID NO 269
<211> LENGTH: 40
<212> TYPE: DNA
<213> ORGANISM: Artificial Sequence
<220> FEATURE:
<223> OTHER INFORMATION: Synthesized

<400> SEQUENCE: 269
cttggcaccc gagaattcca ctgtctccag gagcagcttc                            40

<210> SEQ ID NO 270
<211> LENGTH: 42
<212> TYPE: DNA
<213> ORGANISM: Artificial Sequence
<220> FEATURE:
<223> OTHER INFORMATION: Synthesized

<400> SEQUENCE: 270
cttggcaccc gagaattcca cggaggtgag tacagaaagt gg                         42

<210> SEQ ID NO 271
<211> LENGTH: 39
<212> TYPE: DNA
<213> ORGANISM: Artificial Sequence
<220> FEATURE:
<223> OTHER INFORMATION: Synthesized

<400> SEQUENCE: 271
cttggcaccc gagaattcca ggaggcagct tgtgacacg                             39

<210> SEQ ID NO 272
<211> LENGTH: 40
<212> TYPE: DNA
<213> ORGANISM: Artificial Sequence
<220> FEATURE:
<223> OTHER INFORMATION: Synthesized

<400> SEQUENCE: 272
cttggcaccc gagaattcca ctcgtccagg atgctctcag                            40

<210> SEQ ID NO 273

```
<211> LENGTH: 38
<212> TYPE: DNA
<213> ORGANISM: Artificial Sequence
<220> FEATURE:
<223> OTHER INFORMATION: Synthesized

<400> SEQUENCE: 273
cttggcaccc gagaattcca gtggtggacg tggtggtg                              38

<210> SEQ ID NO 274
<211> LENGTH: 44
<212> TYPE: DNA
<213> ORGANISM: Artificial Sequence
<220> FEATURE:
<223> OTHER INFORMATION: Synthesized

<400> SEQUENCE: 274
cttggcaccc gagaattcca tgattttctg gttcttctcc gcat                       44

<210> SEQ ID NO 275
<211> LENGTH: 44
<212> TYPE: DNA
<213> ORGANISM: Artificial Sequence
<220> FEATURE:
<223> OTHER INFORMATION: Synthesized

<400> SEQUENCE: 275
cttggcaccc gagaattcca gaggtatcca catcctcttc ctca                       44

<210> SEQ ID NO 276
<211> LENGTH: 40
<212> TYPE: DNA
<213> ORGANISM: Artificial Sequence
<220> FEATURE:
<223> OTHER INFORMATION: Synthesized

<400> SEQUENCE: 276
cttggcaccc gagaattcca aggacttccc aggaatccag                            40

<210> SEQ ID NO 277
<211> LENGTH: 38
<212> TYPE: DNA
<213> ORGANISM: Artificial Sequence
<220> FEATURE:
<223> OTHER INFORMATION: Synthesized

<400> SEQUENCE: 277
cttggcaccc gagaattcca agctaggagg cccgactt                              38

<210> SEQ ID NO 278
<211> LENGTH: 38
<212> TYPE: DNA
<213> ORGANISM: Artificial Sequence
<220> FEATURE:
<223> OTHER INFORMATION: Synthesized

<400> SEQUENCE: 278
cttggcaccc gagaattcca acaacggcct tgaccctg                              38

<210> SEQ ID NO 279
<211> LENGTH: 43
<212> TYPE: DNA
<213> ORGANISM: Artificial Sequence
<220> FEATURE:
<223> OTHER INFORMATION: Synthesized
```

<400> SEQUENCE: 279
cttggcaccc gagaattcca ccaccccaaa tctgttaatc acc        43

<210> SEQ ID NO 280
<211> LENGTH: 40
<212> TYPE: DNA
<213> ORGANISM: Artificial Sequence
<220> FEATURE:
<223> OTHER INFORMATION: Synthesized

<400> SEQUENCE: 280
cttggcaccc gagaattcca aacacttccc cgcgacttgg          40

<210> SEQ ID NO 281
<211> LENGTH: 38
<212> TYPE: DNA
<213> ORGANISM: Artificial Sequence
<220> FEATURE:
<223> OTHER INFORMATION: Synthesized

<400> SEQUENCE: 281
cttggcaccc gagaattcca cgtgaagggg aggacgga            38

<210> SEQ ID NO 282
<211> LENGTH: 38
<212> TYPE: DNA
<213> ORGANISM: Artificial Sequence
<220> FEATURE:
<223> OTHER INFORMATION: Synthesized

<400> SEQUENCE: 282
cttggcaccc gagaattcca ggggccatga tgtggagg            38

<210> SEQ ID NO 283
<211> LENGTH: 38
<212> TYPE: DNA
<213> ORGANISM: Artificial Sequence
<220> FEATURE:
<223> OTHER INFORMATION: Synthesized

<400> SEQUENCE: 283
cttggcaccc gagaattcca aaggtgaagg ggcaggac            38

<210> SEQ ID NO 284
<211> LENGTH: 38
<212> TYPE: DNA
<213> ORGANISM: Artificial Sequence
<220> FEATURE:
<223> OTHER INFORMATION: Synthesized

<400> SEQUENCE: 284
cttggcaccc gagaattcca gcggaaagga aggggagg            38

<210> SEQ ID NO 285
<211> LENGTH: 37
<212> TYPE: DNA
<213> ORGANISM: Artificial Sequence
<220> FEATURE:
<223> OTHER INFORMATION: Synthesized

<400> SEQUENCE: 285
cttggcaccc gagaattcca gcagcacctc gcggtag             37

<210> SEQ ID NO 286

```
<210> SEQ ID NO 286
<211> LENGTH: 42
<212> TYPE: DNA
<213> ORGANISM: Artificial Sequence
<220> FEATURE:
<223> OTHER INFORMATION: Synthesized

<400> SEQUENCE: 286
cttggcaccc gagaattcca ggaaagtata ggcccctcac tc          42

<210> SEQ ID NO 287
<211> LENGTH: 38
<212> TYPE: DNA
<213> ORGANISM: Artificial Sequence
<220> FEATURE:
<223> OTHER INFORMATION: Synthesized

<400> SEQUENCE: 287
cttggcaccc gagaattcca ctctccatgt tcggggca              38

<210> SEQ ID NO 288
<211> LENGTH: 47
<212> TYPE: DNA
<213> ORGANISM: Artificial Sequence
<220> FEATURE:
<223> OTHER INFORMATION: Synthesized

<400> SEQUENCE: 288
cttggcaccc gagaattcca gaggattctt gtcaacaaga aaaccc      47

<210> SEQ ID NO 289
<211> LENGTH: 43
<212> TYPE: DNA
<213> ORGANISM: Artificial Sequence
<220> FEATURE:
<223> OTHER INFORMATION: Synthesized

<400> SEQUENCE: 289
cttggcaccc gagaattcca acaagaggtt ggtgagtgat tgg         43

<210> SEQ ID NO 290
<211> LENGTH: 46
<212> TYPE: DNA
<213> ORGANISM: Artificial Sequence
<220> FEATURE:
<223> OTHER INFORMATION: Synthesized

<400> SEQUENCE: 290
cttggcaccc gagaattcca gtccagaaga accaacaaga agatga      46

<210> SEQ ID NO 291
<211> LENGTH: 45
<212> TYPE: DNA
<213> ORGANISM: Artificial Sequence
<220> FEATURE:
<223> OTHER INFORMATION: Synthesized

<400> SEQUENCE: 291
cttggcaccc gagaattcca catagaggtt ccttgagcag gaatc       45

<210> SEQ ID NO 292
<211> LENGTH: 43
<212> TYPE: DNA
<213> ORGANISM: Artificial Sequence
<220> FEATURE:
<223> OTHER INFORMATION: Synthesized
```

<400> SEQUENCE: 292
cttggcaccc gagaattcca cactcccata ggaatcttgc gaa        43

<210> SEQ ID NO 293
<211> LENGTH: 43
<212> TYPE: DNA
<213> ORGANISM: Artificial Sequence
<220> FEATURE:
<223> OTHER INFORMATION: Synthesized

<400> SEQUENCE: 293
cttggcaccc gagaattcca cccccaatac cacatcatcc ata        43

<210> SEQ ID NO 294
<211> LENGTH: 47
<212> TYPE: DNA
<213> ORGANISM: Artificial Sequence
<220> FEATURE:
<223> OTHER INFORMATION: Synthesized

<400> SEQUENCE: 294
cttggcaccc gagaattcca agggttcaaa tgtataccca aagacaa        47

<210> SEQ ID NO 295
<211> LENGTH: 48
<212> TYPE: DNA
<213> ORGANISM: Artificial Sequence
<220> FEATURE:
<223> OTHER INFORMATION: Synthesized

<400> SEQUENCE: 295
cttggcaccc gagaattcca agtttagta caatatgttc ttgcggta        48

<210> SEQ ID NO 296
<211> LENGTH: 41
<212> TYPE: DNA
<213> ORGANISM: Artificial Sequence
<220> FEATURE:
<223> OTHER INFORMATION: Synthesized

<400> SEQUENCE: 296
cttggcaccc gagaattcca cattgtgtaa aaggggcagc a        41

<210> SEQ ID NO 297
<211> LENGTH: 46
<212> TYPE: DNA
<213> ORGANISM: Artificial Sequence
<220> FEATURE:
<223> OTHER INFORMATION: Synthesized

<400> SEQUENCE: 297
cttggcaccc gagaattcca tgtttacaca gaaaggcctt gtaagt        46

<210> SEQ ID NO 298
<211> LENGTH: 39
<212> TYPE: DNA
<213> ORGANISM: Artificial Sequence
<220> FEATURE:
<223> OTHER INFORMATION: Synthesized

<400> SEQUENCE: 298
cttggcaccc gagaattcca catgcggcga tggccaata        39

<210> SEQ ID NO 299

```
<211> LENGTH: 45
<212> TYPE: DNA
<213> ORGANISM: Artificial Sequence
<220> FEATURE:
<223> OTHER INFORMATION: Synthesized

<400> SEQUENCE: 299
cttggcaccc gagaattcca ttccgagaga ggacaacaga gttgt            45

<210> SEQ ID NO 300
<211> LENGTH: 41
<212> TYPE: DNA
<213> ORGANISM: Artificial Sequence
<220> FEATURE:
<223> OTHER INFORMATION: Synthesized

<400> SEQUENCE: 300
cttggcaccc gagaattcca gacgggacgt aaacaaagga c                41

<210> SEQ ID NO 301
<211> LENGTH: 40
<212> TYPE: DNA
<213> ORGANISM: Artificial Sequence
<220> FEATURE:
<223> OTHER INFORMATION: Synthesized

<400> SEQUENCE: 301
cttggcaccc gagaattcca ggagaccgcg taaagagagg                 40

<210> SEQ ID NO 302
<211> LENGTH: 40
<212> TYPE: DNA
<213> ORGANISM: Artificial Sequence
<220> FEATURE:
<223> OTHER INFORMATION: Synthesized

<400> SEQUENCE: 302
cttggcaccc gagaattcca gtgcagaggt gaagcgaagt                 40

<210> SEQ ID NO 303
<211> LENGTH: 45
<212> TYPE: DNA
<213> ORGANISM: Artificial Sequence
<220> FEATURE:
<223> OTHER INFORMATION: Synthesized

<400> SEQUENCE: 303
cttggcaccc gagaattcca tccaagagtc ctcttatgta agacc            45

<210> SEQ ID NO 304
<211> LENGTH: 43
<212> TYPE: DNA
<213> ORGANISM: Artificial Sequence
<220> FEATURE:
<223> OTHER INFORMATION: Synthesized

<400> SEQUENCE: 304
cttggcaccc gagaattcca caactcctcc cagtccttaa aca              43

<210> SEQ ID NO 305
<211> LENGTH: 40
<212> TYPE: DNA
<213> ORGANISM: Artificial Sequence
<220> FEATURE:
<223> OTHER INFORMATION: Synthesized
```

<400> SEQUENCE: 305
cttggcaccc gagaattcca ggtgctggtg aacagaccaa    40

<210> SEQ ID NO 306
<211> LENGTH: 42
<212> TYPE: DNA
<213> ORGANISM: Artificial Sequence
<220> FEATURE:
<223> OTHER INFORMATION: Synthesized

<400> SEQUENCE: 306
cttggcaccc gagaattcca cttggaggct tgaacagtag ga    42

<210> SEQ ID NO 307
<211> LENGTH: 45
<212> TYPE: DNA
<213> ORGANISM: Artificial Sequence
<220> FEATURE:
<223> OTHER INFORMATION: Synthesized

<400> SEQUENCE: 307
cttggcaccc gagaattcca aattctttat acgggtcaat gtcca    45

<210> SEQ ID NO 308
<211> LENGTH: 38
<212> TYPE: DNA
<213> ORGANISM: Artificial Sequence
<220> FEATURE:
<223> OTHER INFORMATION: Synthesized

<400> SEQUENCE: 308
cttggcaccc gagaattcca cagaggcggt gtcgagga    38

<210> SEQ ID NO 309
<211> LENGTH: 40
<212> TYPE: DNA
<213> ORGANISM: Artificial Sequence
<220> FEATURE:
<223> OTHER INFORMATION: Synthesized

<400> SEQUENCE: 309
cttggcaccc gagaattcca acacagaaca gcttgcctga    40

<210> SEQ ID NO 310
<211> LENGTH: 44
<212> TYPE: DNA
<213> ORGANISM: Artificial Sequence
<220> FEATURE:
<223> OTHER INFORMATION: Synthesized

<400> SEQUENCE: 310
cttggcaccc gagaattcca ctgggtcttc caaattactt ccca    44

<210> SEQ ID NO 311
<211> LENGTH: 46
<212> TYPE: DNA
<213> ORGANISM: Artificial Sequence
<220> FEATURE:
<223> OTHER INFORMATION: Synthesized

<400> SEQUENCE: 311
cttggcaccc gagaattcca gtttctcttc caaaggtaag acagga    46

<210> SEQ ID NO 312

```
<211> LENGTH: 43
<212> TYPE: DNA
<213> ORGANISM: Artificial Sequence
<220> FEATURE:
<223> OTHER INFORMATION: Synthesized

<400> SEQUENCE: 312
cttggcaccc gagaattcca acctgcctct acgtctaaca aca                    43

<210> SEQ ID NO 313
<211> LENGTH: 47
<212> TYPE: DNA
<213> ORGANISM: Artificial Sequence
<220> FEATURE:
<223> OTHER INFORMATION: Synthesized

<400> SEQUENCE: 313
cttggcaccc gagaattcca ttgtgagtcc aagggatact aacattg                47

<210> SEQ ID NO 314
<211> LENGTH: 44
<212> TYPE: DNA
<213> ORGANISM: Artificial Sequence
<220> FEATURE:
<223> OTHER INFORMATION: Synthesized

<400> SEQUENCE: 314
cttggcaccc gagaattcca gggagtttgc cactcaggat taaa                   44

<210> SEQ ID NO 315
<211> LENGTH: 47
<212> TYPE: DNA
<213> ORGANISM: Artificial Sequence
<220> FEATURE:
<223> OTHER INFORMATION: Synthesized

<400> SEQUENCE: 315
cttggcaccc gagaattcca gggcaaatac ttggtaaggt taggata                47

<210> SEQ ID NO 316
<211> LENGTH: 49
<212> TYPE: DNA
<213> ORGANISM: Artificial Sequence
<220> FEATURE:
<223> OTHER INFORMATION: Synthesized

<400> SEQUENCE: 316
cttggcaccc gagaattcca ccttccacag agtatgtaaa taatgccta              49

<210> SEQ ID NO 317
<211> LENGTH: 42
<212> TYPE: DNA
<213> ORGANISM: Artificial Sequence
<220> FEATURE:
<223> OTHER INFORMATION: Synthesized

<400> SEQUENCE: 317
cttggcaccc gagaattcca ctcccatgct gtagctcttg tt                     42

<210> SEQ ID NO 318
<211> LENGTH: 40
<212> TYPE: DNA
<213> ORGANISM: Artificial Sequence
<220> FEATURE:
<223> OTHER INFORMATION: Synthesized
```

<400> SEQUENCE: 318
cttggcaccc gagaattcca gctgggtcca actggtgatc        40

<210> SEQ ID NO 319
<211> LENGTH: 40
<212> TYPE: DNA
<213> ORGANISM: Artificial Sequence
<220> FEATURE:
<223> OTHER INFORMATION: Synthesized

<400> SEQUENCE: 319
cttggcaccc gagaattcca ccccaaaaga ccaccgtgtg        40

<210> SEQ ID NO 320
<211> LENGTH: 41
<212> TYPE: DNA
<213> ORGANISM: Artificial Sequence
<220> FEATURE:
<223> OTHER INFORMATION: Synthesized

<400> SEQUENCE: 320
cttggcaccc gagaattcca tcttcctgac tgccgattgg t        41

<210> SEQ ID NO 321
<211> LENGTH: 40
<212> TYPE: DNA
<213> ORGANISM: Artificial Sequence
<220> FEATURE:
<223> OTHER INFORMATION: Synthesized

<400> SEQUENCE: 321
cttggcaccc gagaattcca caagaccttg ggcaggttcc        40

<210> SEQ ID NO 322
<211> LENGTH: 43
<212> TYPE: DNA
<213> ORGANISM: Artificial Sequence
<220> FEATURE:
<223> OTHER INFORMATION: Synthesized

<400> SEQUENCE: 322
cttggcaccc gagaattcca attctaaggc ttcccgatac aga        43

<210> SEQ ID NO 323
<211> LENGTH: 46
<212> TYPE: DNA
<213> ORGANISM: Artificial Sequence
<220> FEATURE:
<223> OTHER INFORMATION: Synthesized

<400> SEQUENCE: 323
cttggcaccc gagaattcca acgctggatc ttctaaatta ttaccc        46

<210> SEQ ID NO 324
<211> LENGTH: 43
<212> TYPE: DNA
<213> ORGANISM: Artificial Sequence
<220> FEATURE:
<223> OTHER INFORMATION: Synthesized

<400> SEQUENCE: 324
cttggcaccc gagaattcca gatccactca cagtttccat agg        43

<210> SEQ ID NO 325

<211> LENGTH: 40
<212> TYPE: DNA
<213> ORGANISM: Artificial Sequence
<220> FEATURE:
<223> OTHER INFORMATION: Synthesized

<400> SEQUENCE: 325
cttggcaccc gagaattcca cagcccaacc cttgtcctta                     40

<210> SEQ ID NO 326
<211> LENGTH: 41
<212> TYPE: DNA
<213> ORGANISM: Artificial Sequence
<220> FEATURE:
<223> OTHER INFORMATION: Synthesized

<400> SEQUENCE: 326
cttggcaccc gagaattcca tgggagcttc atctggacct g                   41

<210> SEQ ID NO 327
<211> LENGTH: 41
<212> TYPE: DNA
<213> ORGANISM: Artificial Sequence
<220> FEATURE:
<223> OTHER INFORMATION: Synthesized

<400> SEQUENCE: 327
cttggcaccc gagaattcca gaagggacag aagatgacag g                   41

<210> SEQ ID NO 328
<211> LENGTH: 41
<212> TYPE: DNA
<213> ORGANISM: Artificial Sequence
<220> FEATURE:
<223> OTHER INFORMATION: Synthesized

<400> SEQUENCE: 328
cttggcaccc gagaattcca caagaagccc agacggaaac c                   41

<210> SEQ ID NO 329
<211> LENGTH: 38
<212> TYPE: DNA
<213> ORGANISM: Artificial Sequence
<220> FEATURE:
<223> OTHER INFORMATION: Synthesized

<400> SEQUENCE: 329
cttggcaccc gagaattcca cccctcaggg caactgac                       38

<210> SEQ ID NO 330
<211> LENGTH: 44
<212> TYPE: DNA
<213> ORGANISM: Artificial Sequence
<220> FEATURE:
<223> OTHER INFORMATION: Synthesized

<400> SEQUENCE: 330
cttggcaccc gagaattcca gtgctgtgac tgcttgtaga tggc                44

<210> SEQ ID NO 331
<211> LENGTH: 41
<212> TYPE: DNA
<213> ORGANISM: Artificial Sequence
<220> FEATURE:
<223> OTHER INFORMATION: Synthesized -continued

<400> SEQUENCE: 331
cttggcaccc gagaattcca atctgagcag cgctcatggt g                    41

<210> SEQ ID NO 332
<211> LENGTH: 38
<212> TYPE: DNA
<213> ORGANISM: Artificial Sequence
<220> FEATURE:
<223> OTHER INFORMATION: Synthesized

<400> SEQUENCE: 332
cttggcaccc gagaattcca ccctgtcgtc tctccagc                        38

<210> SEQ ID NO 333
<211> LENGTH: 47
<212> TYPE: DNA
<213> ORGANISM: Artificial Sequence
<220> FEATURE:
<223> OTHER INFORMATION: Synthesized

<400> SEQUENCE: 333
cttggcaccc gagaattcca ctatgtcgaa aagtgtttct gtcatcc              47

<210> SEQ ID NO 334
<211> LENGTH: 41
<212> TYPE: DNA
<213> ORGANISM: Artificial Sequence
<220> FEATURE:
<223> OTHER INFORMATION: Synthesized

<400> SEQUENCE: 334
cttggcaccc gagaattcca gagacccag ttgcaaacca g                     41

<210> SEQ ID NO 335
<211> LENGTH: 38
<212> TYPE: DNA
<213> ORGANISM: Artificial Sequence
<220> FEATURE:
<223> OTHER INFORMATION: Synthesized

<400> SEQUENCE: 335
cttggcaccc gagaattcca tgggcctccg gttcatgc                        38

<210> SEQ ID NO 336
<211> LENGTH: 38
<212> TYPE: DNA
<213> ORGANISM: Artificial Sequence
<220> FEATURE:
<223> OTHER INFORMATION: Synthesized

<400> SEQUENCE: 336
cttggcaccc gagaattcca gtgcagggtg gcaagtgg                        38

<210> SEQ ID NO 337
<211> LENGTH: 39
<212> TYPE: DNA
<213> ORGANISM: Artificial Sequence
<220> FEATURE:
<223> OTHER INFORMATION: Synthesized

<400> SEQUENCE: 337
cttggcaccc gagaattcca gacaggcaca aacacgcac                       39

<210> SEQ ID NO 338

```
<211> LENGTH: 44
<212> TYPE: DNA
<213> ORGANISM: Artificial Sequence
<220> FEATURE:
<223> OTHER INFORMATION: Synthesized

<400> SEQUENCE: 338
cttggcaccc gagaattcca ttcttgcgga gattctcttc ctct                         44

<210> SEQ ID NO 339
<211> LENGTH: 40
<212> TYPE: DNA
<213> ORGANISM: Artificial Sequence
<220> FEATURE:
<223> OTHER INFORMATION: Synthesized

<400> SEQUENCE: 339
cttggcaccc gagaattcca cgcttcttgt cctgcttgct                              40

<210> SEQ ID NO 340
<211> LENGTH: 46
<212> TYPE: DNA
<213> ORGANISM: Artificial Sequence
<220> FEATURE:
<223> OTHER INFORMATION: Synthesized

<400> SEQUENCE: 340
cttggcaccc gagaattcca acttgataag aggtcccaag acttag                       46

<210> SEQ ID NO 341
<211> LENGTH: 38
<212> TYPE: DNA
<213> ORGANISM: Artificial Sequence
<220> FEATURE:
<223> OTHER INFORMATION: Synthesized

<400> SEQUENCE: 341
cttggcaccc gagaattcca agcctgggca tccttgag                                38

<210> SEQ ID NO 342
<211> LENGTH: 38
<212> TYPE: DNA
<213> ORGANISM: Artificial Sequence
<220> FEATURE:
<223> OTHER INFORMATION: Synthesized

<400> SEQUENCE: 342
cttggcaccc gagaattcca caggaagggg ctgaggtc                                38

<210> SEQ ID NO 343
<211> LENGTH: 44
<212> TYPE: DNA
<213> ORGANISM: Artificial Sequence
<220> FEATURE:
<223> OTHER INFORMATION: Synthesized

<400> SEQUENCE: 343
cttggcaccc gagaattcca catgagtttt ttatggcggg aggt                         44

<210> SEQ ID NO 344
<211> LENGTH: 41
<212> TYPE: DNA
<213> ORGANISM: Artificial Sequence
<220> FEATURE:
<223> OTHER INFORMATION: Synthesized
```

```
<400> SEQUENCE: 344
cttggcaccc gagaattcca cagtggggaa caagaagtgg a                          41

<210> SEQ ID NO 345
<211> LENGTH: 58
<212> TYPE: DNA
<213> ORGANISM: Artificial Sequence
<220> FEATURE:
<223> OTHER INFORMATION: Synthesized

<400> SEQUENCE: 345
aatgatacgg cgaccaccga gatctacact ctttccctac acgacgctct tccgatct       58

<210> SEQ ID NO 346
<211> LENGTH: 24
<212> TYPE: DNA
<213> ORGANISM: Artificial Sequence
<220> FEATURE:
<223> OTHER INFORMATION: Synthesized

<400> SEQUENCE: 346
caagcagaag acggcatacg agat                                             24

<210> SEQ ID NO 347
<211> LENGTH: 27
<212> TYPE: DNA
<213> ORGANISM: Artificial Sequence
<220> FEATURE:
<223> OTHER INFORMATION: Synthesized

<400> SEQUENCE: 347
gtctcgtggg ctcggagatg tgtataa                                          27
```